US008900134B2

(12) United States Patent
Fujiyama et al.

(10) Patent No.: US 8,900,134 B2
(45) Date of Patent: Dec. 2, 2014

(54) ENDOSCOPE APPARATUS AND METHOD OF CONTROLLING ENDOSCOPE APPARATUS

(75) Inventors: Tetsuji Fujiyama, Okaya (JP); Tomohisa Furuta, Nagano (JP); Mitsuo Obata, Hino (JP)

(73) Assignee: Olympus Corporation, Tokyo (JP)

( * ) Notice: Subject to any disclaimer, the term of this patent is extended or adjusted under 35 U.S.C. 154(b) by 1588 days.

(21) Appl. No.: 12/069,698

(22) Filed: Feb. 12, 2008

(65) Prior Publication Data

US 2009/0203965 A1 Aug. 13, 2009

(51) Int. Cl.

| | |
|---|---|
| ***A61B 1/06*** | (2006.01) |
| ***A61B 1/00*** | (2006.01) |
| ***A61B 1/04*** | (2006.01) |
| ***A61B 1/045*** | (2006.01) |
| *H04N 5/225* | (2006.01) |

(52) U.S. Cl.

CPC ........ *A61B 1/042* (2013.01); *H04N 2005/2255* (2013.01); *A61B 1/00096* (2013.01); *A61B 1/045* (2013.01); *A61B 1/00101* (2013.01)

USPC .......................................... 600/175; 600/178

(58) Field of Classification Search

CPC .. A61B 1/00101; A61B 1/0676; A61B 1/053; G02B 23/243; G02B 23/2423

USPC ......... 600/112, 118, 129, 136, 172, 174, 175, 600/178, 179, 249, 180; 324/414

See application file for complete search history.

(56) References Cited

U.S. PATENT DOCUMENTS

| | | | | |
|---|---|---|---|---|
| 2003/0139656 | A1 * | 7/2003 | Kiani et al. | 600/322 |
| 2004/0090189 | A1 * | 5/2004 | Yoneda et al. | 315/291 |
| 2006/0020168 | A1 * | 1/2006 | Naruse | 600/179 |
| 2006/0069309 | A1 * | 3/2006 | Ono | 600/134 |
| 2007/0100202 | A1 * | 5/2007 | Murata | 600/109 |
| 2007/0244366 | A1 * | 10/2007 | Murata | 600/175 |

FOREIGN PATENT DOCUMENTS

| | | | | |
|---|---|---|---|---|
| JP | 2001-061777 | A | | 3/2001 |
| JP | 2004-158840 | A | | 6/2004 |
| JP | 2004-313241 | A | | 11/2004 |
| JP | 2006-158516 | A | | 6/2006 |
| JP | 2006158516 | A | * | 6/2006 |

* cited by examiner

*Primary Examiner* — Anhtuan T Nguyen
*Assistant Examiner* — Rynae Boler
(74) *Attorney, Agent, or Firm* — Holtz, Holtz, Goodman & Chick, PC

(57) ABSTRACT

An endoscope apparatus includes an endoscope insertion section and an optical adapter that is detachably attachable to the endoscope insertion section. In the optical adapter, an LED and a resistor for connection detection are connected in parallel to two electric contacts. In the endoscope insertion section, two signal lines are connected to electric contacts, which are connectable to the two electric contacts in the optical adapter. The endoscope apparatus includes an attachment-and-detachment determining power supply that is connected to one of the signal lines through a switching circuit, and an optical-adapter-attachment-and-detachment determining section. When connection of the optical adapter is detected, the switching circuit is switched to supply an electric current for turning on the LED from an LED turn-on power supply to the one of the signal lines.

11 Claims, 27 Drawing Sheets

USER INTERFACE
7
1
SYSTEM CONTROL SECTION
29
IMAGE PROCESSING SECTION
LED DRIVING SECTION
23
24
28
6
POWER SUPPLY FOR DETERMINING ATTACHMENT AND DETACHMENT
POWER SUPPLY FOR TURNING ON LED
OPTICAL-ADAPTER-ATTACHMENT-AND-DETACHMENT DETERMINING SECTION
27
CCD DRIVING SECTION
5
21
22
SWITCH CIRCUIT
18
2
26
16
CCD
10
4
13
RESISTOR
LED
17a
17b
3
15
14
12
11

5
4
13
11
12
14
15
17a
17b
31
32
Vcc
34
33
VOLTAGE DETECTOR
35
24
37
38
23
18a
18
18b
a
b
c
22
POWER SUPPLY FOR TURNING ON LED
21
POWER SUPPLY FOR DETERMINING ATTACHMENT AND DETACHMENT
POWER SUPPLY FOR DRIVING LED

POWER SUPPLY FOR DETERMINING ATTACHMENT AND DETACHMENT
POWER SUPPLY FOR TURNING ON LED
POWER SUPPLY FOR DRIVING LED
VOLTAGE DETECTOR
Vcc

SWITCH INSTRUCTING SECTION
SWITCH CONTROL SECTION
VOLTAGE DETECTOR
Vcc
POWER SUPPLY FOR TURNING ON LED
POWER SUPPLY FOR DETERMINING ATTACHMENT AND DETACHMENT
POWER SUPPLY FOR DRIVING LED
4
5
11
12
13
14
15
17a
17b
18
18a
18b
21
22
23
24
31
32
33
34
35
37
38
61
62
63
a
b
c 5
4
13
11
12
14
15
17a
17b
VOLTAGE DETECTOR
66
35
24
23
37
38
18a
18
18b
a
b
c
a
b
c
22
POWER SUPPLY FOR TURNING ON LED
21
POWER SUPPLY FOR DETERMINING ATTACHMENT AND DETACHMENT
POWER SUPPLY FOR DRIVING LED

POWER SUPPLY FOR TURNING ON LED 22
POWER SUPPLY FOR DRIVING LED
POWER SUPPLY FOR DETERMINING ATTACHMENT AND DETACHMENT 21
VOLTAGE DETECTOR
71
38
37a
23
66
35
24
17a
17b
15
26
(17c)
14
2
5
4
13
11
12

5
4
13
11
14
15
17a
17b
POWER SUPPLY FOR TURNING ON LED 22
37
38
POWER SUPPLY FOR DRIVING LED
23
24
VOLTAGE DETECTOR
35
TO SYSTEM CONTROL SECTION 29

USER INTERFACE
107
101
SYSTEM CONTROL SECTION
129
LED DRIVING SECTION
123
124
125
IMAGE PROCESSING SECTION
128
106
POWER SUPPLY FOR DETERMINING ATTACHMENT AND DETACHMENT
POWER SUPPLY FOR TURNING ON LED
OPTICAL-ADAPTER-ATTACHMENT-AND-DETACHMENT DETERMINING SECTION
OPTICAL-ADAPTER-TYPE DETERMINING SECTION
127
CCD DRIVING SECTION
105
121
122
SWITCH CIRCUIT
118
102
126
116
CCD
110
104
113
RESISTOR
LED
117a
117b
103
115
114
112
111

RESISTOR
OPTICAL-ADAPTER-ATTACHMENT-AND-DETACHMENT DETERMINING SECTION
OPTICAL-ADAPTER-TYPE DETERMINING SECTION
POWER SUPPLY FOR TURNING ON LED
POWER SUPPLY FOR DETERMINING ATTACHMENT AND DETACHMENT
LED DRIVING SECTION
SYSTEM CONTROL SECTION
104
113
114
115
102
105
117a
117b
124
125
122
123
129
121
118
118a
118b
a
b
c

POWER SUPPLY FOR DETERMINING ATTACHMENT AND DETACHMENT
POWER SUPPLY FOR TURNING ON LED
LED DRIVING SECTION
OPTICAL-ADAPTER-ATTACHMENT-AND-DETACHMENT DETERMINING SECTION
OPTICAL-ADAPTER-TYPE DETERMINING SECTION
SYSTEM CONTROL SECTION
IMAGE PROCESSING SECTION
CCD DRIVING SECTION
USER INTERFACE
SWITCH CIRCUIT
CCD
RESISTOR
LED
101
102
103
104
105
106
107
110
111
112
113
114
115
116
117a
117b
118
121
122
123
124
125
126
127
128
129

ENDOSCOPE APPARATUS AND METHOD OF CONTROLLING ENDOSCOPE APPARATUS

BACKGROUND OF THE INVENTION

1. Field of the Invention

The present invention relates to an endoscope apparatus in which an optical adapter is detachably attached to a distal end portion of an endoscope insertion section and a method of controlling an endoscope apparatus in which an optical adapter is detachably attached to a distal end portion of an endoscope insertion section.

2. Description of the Related Art

In recent years, endoscope apparatuses which can optically perform inspections, observations, and the like by inserting endoscope insertion sections thereof into the inside of pipes and the like of chemical plants are widely used in the industrial fields and other fields. Among the endoscope apparatuses in the industrial field, there is an endoscope apparatus in which plural kinds of optical adapters are detachably attachable to a distal end portion of an endoscope insertion section to make it possible to appropriately use the endoscope apparatus for various applications.

For example, Japanese Patent Laid-Open No. 2004-313241 discloses an endoscope apparatus in which plural kinds of optical adapters are detachably attachable to a distal end portion of an endoscope insertion section. In the endoscope apparatus, a determining section for determining a type of an optical adapter is provided in the optical adapter and an optical-adapter-type determining section for determining a type of the optical adapter is provided in a control section of the endoscope apparatus.

Japanese Patent Laid-Open No. 2001-61777 discloses an endoscope apparatus in which an optical adapter mounted with a C-MOS sensor and an LED for illumination and having an image pickup function is detachably attachable to a distal end of an endoscope insertion portion, electric cables for the C-MOS sensor and the LED are inserted through the endoscope insertion section, and a video signal output circuit from the C-MOMS sensor and a current limiting circuit for limiting a current value supplied to the LED are provided.

SUMMARY OF THE INVENTION

In an optical adapter, an LED and a resistor for detecting optical adapter connection are connected in parallel to two electric contacts. On the other hand, to two signal lines connected to two electric contacts of an endoscope to which the optical adapter is connected, an attachment-and-detachment determining power supply is connected through a switching circuit and an optical-adapter-attachment-and-detachment determining section is connected. When the connection of the optical adapter is detected, a power supply connected to the two electric contacts is switched from the attachment-and-detachment determining power supply to an LED turn-on power supply by the switching circuit to turn on the LED.

BRIEF DESCRIPTION OF THE DRAWINGS

FIG. 2 is a block diagram showing a configuration of a main part in an endoscope apparatus including an optical-adapter-attachment-and-detachment determining section and the like;

FIG. 16 is a block diagram showing a configuration of a main part in an endoscope apparatus including an optical-adapter-attachment-and-detachment determining section, an optical-adapter-type determining section, and the like;

DETAILED DESCRIPTION OF THE PREFERRED EMBODIMENTS

Embodiments of the present invention will be hereinafter explained with reference to the drawings.

<First Embodiment>

Figure 1:
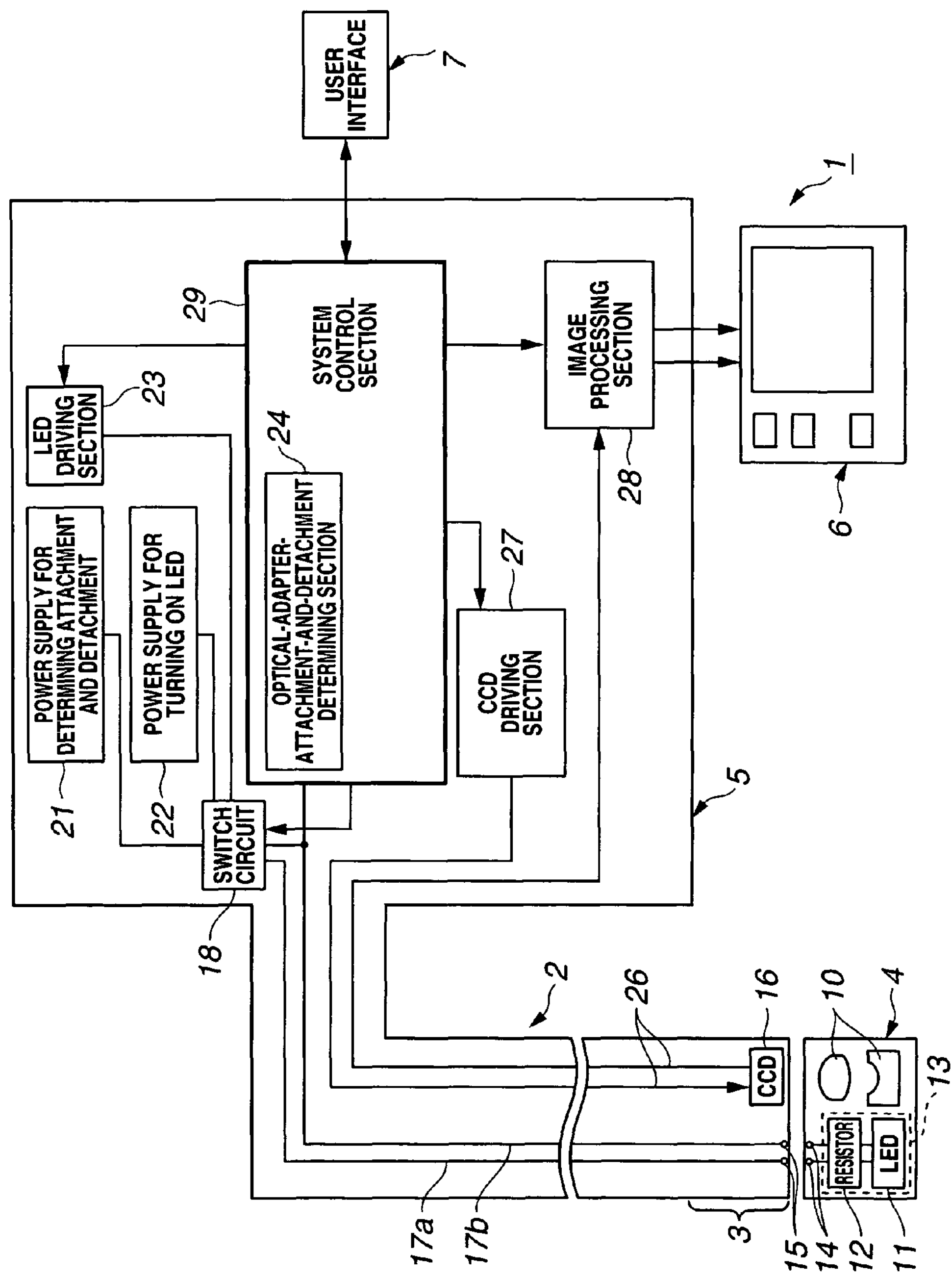
FIG. 1 is a block diagram showing an overall configuration of an endoscope apparatus according to a first embodiment of the present invention.
Figure 2:
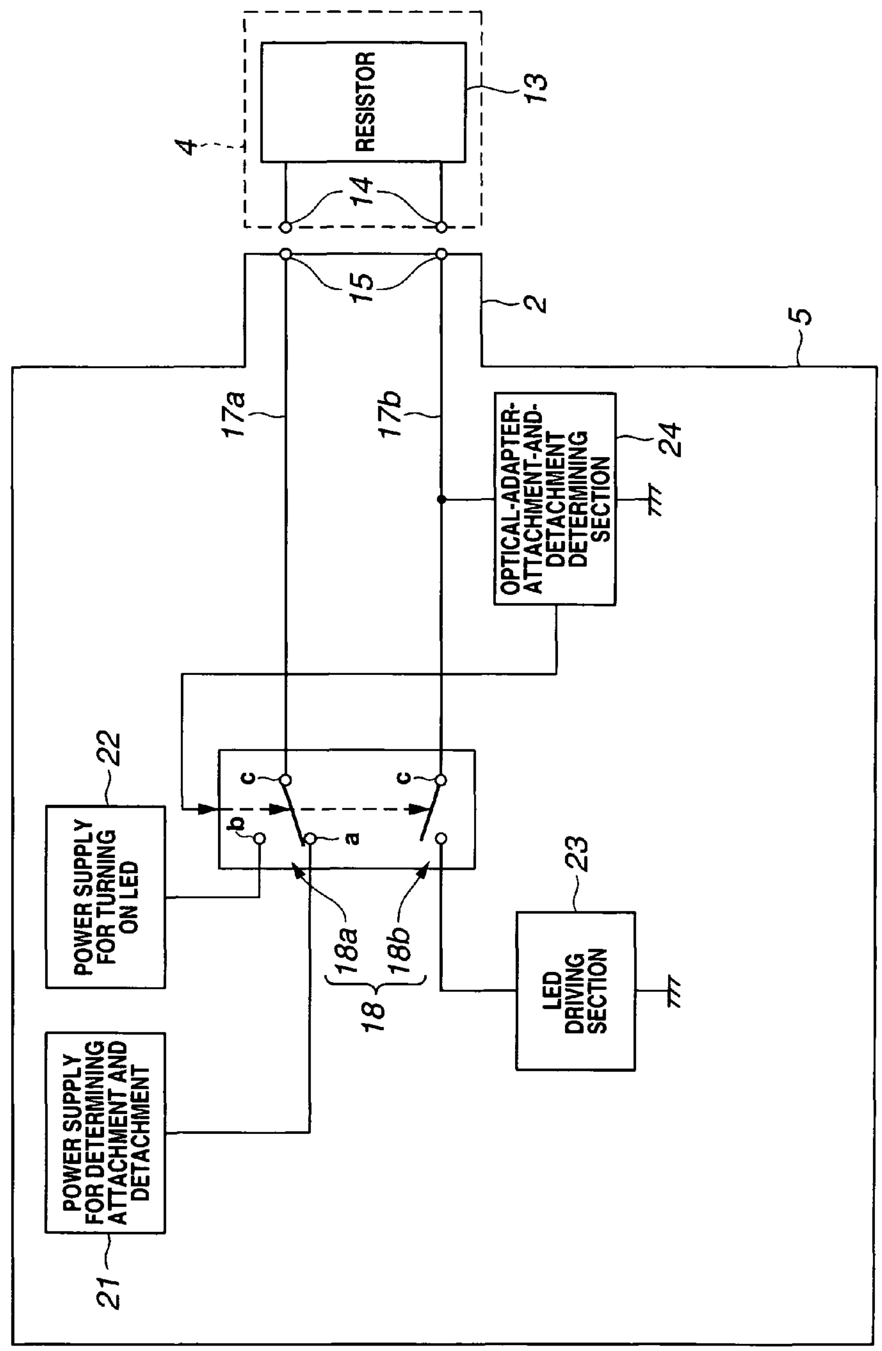
Figure 3:
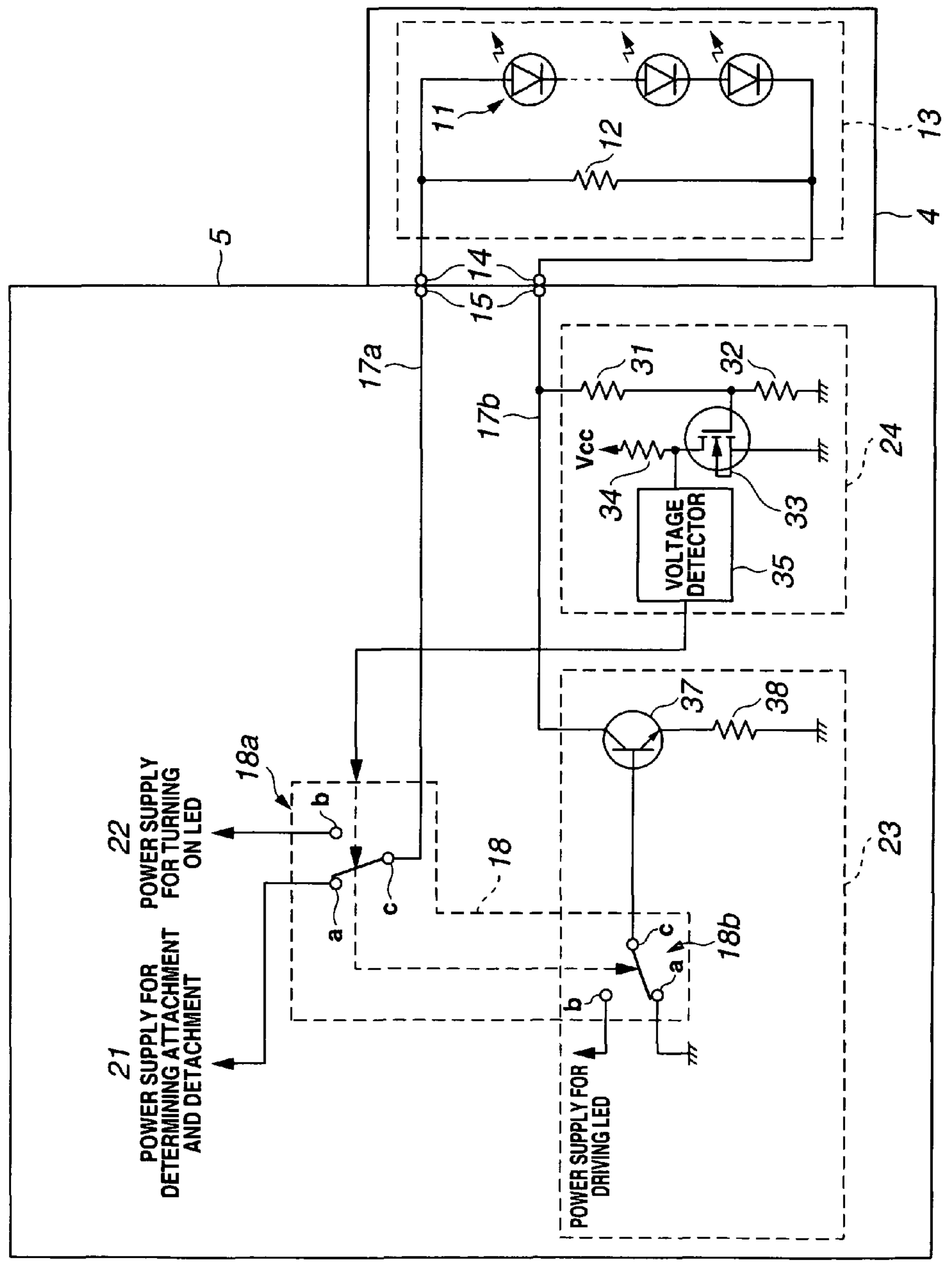
FIG. 3 is a circuit diagram showing a more specific circuit configuration of FIG. 2.
Figure 4:
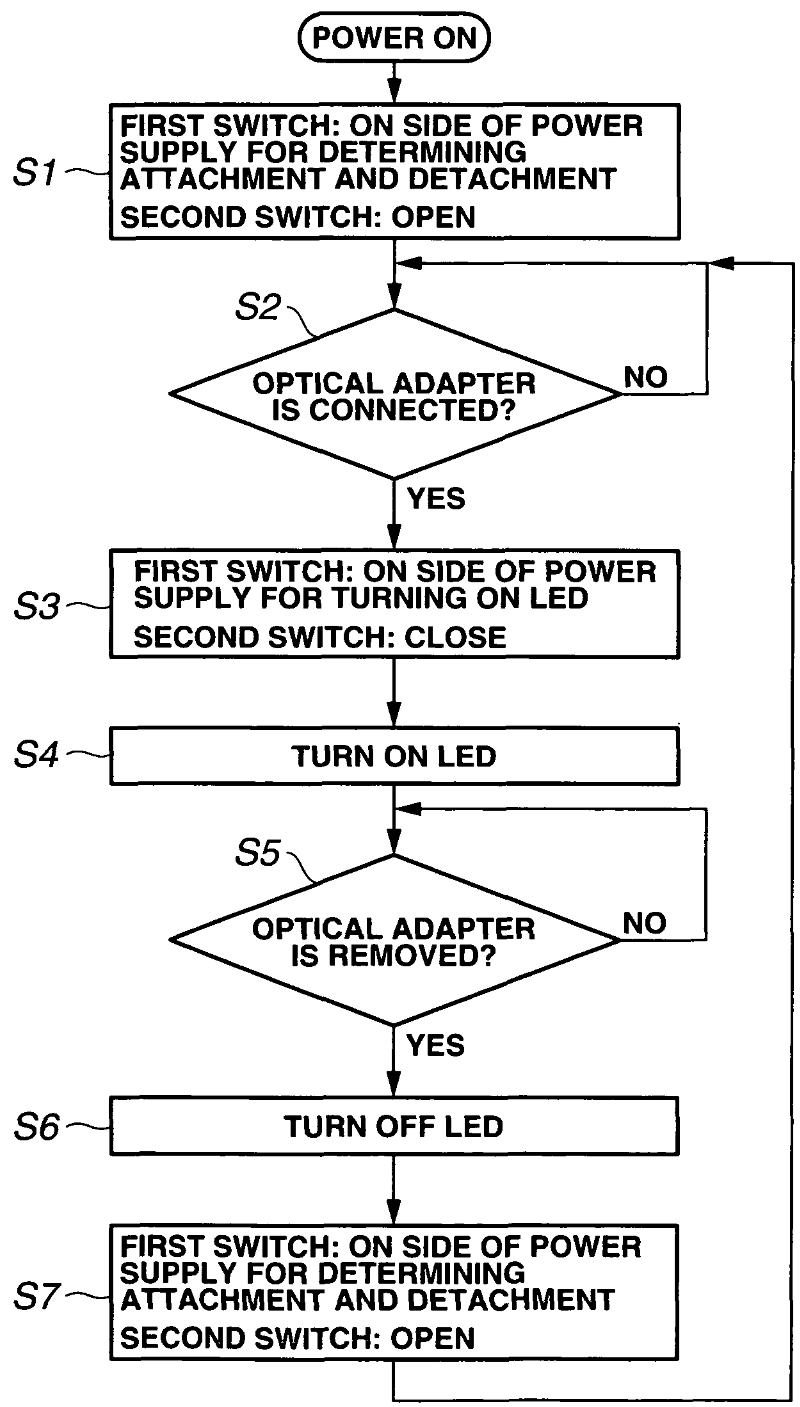
FIG. 4 is a flowchart showing operation contents according to the first embodiment of the present invention.

FIG. 1 to FIG. 4 relate to a first embodiment of the present invention. FIG. 1 shows an overall configuration of an endoscope apparatus according to the first embodiment of the present invention. FIG. 2 shows a configuration of a main part in an endoscope apparatus including an optical-adapter-attachment-and-detachment determining section and the like. FIG. 3 shows a more specific circuit configuration of FIG. 2. FIG. 4 shows operation contents according to the present embodiment.

As shown in FIG. 1, an industrial endoscope apparatus 1 according to the present embodiment includes an endoscope insertion section (hereinafter simply abbreviated as "insertion section") 2 mounted to the inside of inspection objects such as pipes of a chemical plant, an optical adapter 4 detachably connected to a distal end portion 3 of the insertion section 2, an endoscope apparatus main body 5 to which a rear end of the insertion section 2 is coupled and which incorporates an image processing section and the like, a display device 6 which is connected to the endoscope apparatus main body 5 and displays an endoscopic image and the like, and a user interface 7 through which a user performs various kinds of instruction operation and the like.

The endoscope apparatus 1 is small and light and can be driven by a not-shown battery. Therefore, the user on his own can easily carry the endoscope apparatus 1 and use the endoscope apparatus 1 in a desired place.

A not-shown mounting section by a screw section and the like is provided at the distal end portion 3 of the insertion section 2. An optical adapter 4 selected by the user out of plural optical adapters can be detachably mounted.

In the optical adapter 4, object lenses 10 and a light-emitting diode (abbreviated as "LED") 11, which is a luminous body, included in a lighting section arranged adjacent to the object lenses 10 are arranged. The LED 11 may be configured by connecting plural LED elements in series rather than being configured by one LED element. The LED 11 is connected in parallel to a resistor 12 and connected to two electric contacts 14, which are adapter side electric contacts. In the following explanation, it is described that a resistor element 13 is formed by the LED 11 and the resistor 12.

On the other hand, at the distal end portion 3 of the insertion section 2 to which the optical adapter 4 is detachably attachable, electric contacts 15, which are insertion section side electric contacts connectable to the electric contacts 14, are arranged and, for example, a charge coupled device (abbreviated as "CCD") 16 is arranged as an image pickup device in a position opposed to the object lenses 10. Therefore, an optical image is focused on an image pickup surface of the CCD 16 by the object lenses 10.

The electric contacts 15 are connected to a switching circuit 18 and the like, which are provided in the endoscope apparatus main body 5, through two signal lines **17*a* and 17*b* inserted through the insertion section 2. The signal line 17*a* is connected to, through the switching circuit 18, an attachment-and-detachment determining power supply 21, which is a power supply for electrically detecting attachment and detachment of the optical adapter 4, or an LED turn-on power supply 22, which is a luminous body turn-on power supply, for supplying an electric current for lighting to the LED 1. As described later, the attachment-and-detachment determining power supply 21 is a constant-voltage power supply subjected to constant voltage control and the LED turn-on power supply 22 is a constant-current power supply subjected to constant current control. For lighting of the LED 11, an LED driving power supply is also used together with the LED turn-on power supply 22. However, as described later, the LED driving power supply is an auxiliary power supply which an LED driving section 23** uses for driving control.

The signal line **17*b* is connected to, through the switching circuit 18, the LED driving section 23 which drives the LED 11 and connected to an optical-adapter-attachment-and-detachment determining section 24 which electrically determines attachment and detachment of the optical adapter 4**.

The CCD 16 is connected to, through a signal line 26 inserted through the insertion section 2, a CCD driving section 27 which is incorporated in the endoscope apparatus main body 5 and drives the CCD 16 and an image processing section 28 which performs image processing for a CCD output signal outputted from the CCD 16 by the application of a CCD driving signal.

The endoscope apparatus main body 5 includes a system control section 29 which configures the optical-adapter-attachment-and-detachment determining section 24 and performs control of the respective sections in the endoscope apparatus main body 5.

The system control section 29 controls operations of the CCD driving section 27 and the like on the basis of a result of determination on connection of the optical adapter 4 and the distal end portion 3 of the insertion section 2 by the optical-adapter-attachment-and-detachment determining section 24. Specifically, when the optical adapter 4 is connected, the system control section 29 controls the CCD driving section 27 and the like into an operation state and, when the optical adapter 4 is not connected, the system control section 29 controls the CCD driving section 27 and the like into a non-operation state. Therefore, the endoscope apparatus 1 reduces unnecessary power consumption and realize power saving.

When an instruction input such as a still image display instruction is performed from the user interface 7, the system control section 29 controls an image processing operation and the like of the image processing section 28 in response to the instruction input.

Moreover, the system control section 29 performs control for switching by the switching circuit 18 according to a result of determination on connection of the optical adapter 4 and the distal end portion 3 of the insertion section 2 by the optical-adapter-attachment-and-detachment determining section 24.

As described above, in the endoscope apparatus 1, as signal lines disposed in the insertion section 2, there are only two signal lines, i.e., the signal lines **17*a* and 17*b* connected to the optical adapter 4 excluding the signal line 26 connected to the CCD 16. In other words, there are two signal lines in total at the maximum for optical adapter attachment and detachment determination processing and for supplying an electric current for lighting of the luminous body 11, since these lines are shared for use. Therefore, the endoscope apparatus 1 realizes a reduction in diameter of the insertion section 2**, i.e., a reduction in insertion section diameter.

By configuring the optical adapter 4 side with the two electric contacts 14, a reduction in size and a reduction in diameter of the optical adapter 4 are realized. By providing the two electric contacts 14, the number of signal lines in the optical adapter 4 is reduced and a reduction in size of the optical adapter 4 is realized.

FIG. 2 is a block diagram showing a configuration of an electric system of a main part for performing, for example, determination on attachment and detachment of the optical adapter 4 in the present embodiment. In FIG. 2 and the like referred to below, for ease of explanation, the optical-adapter-attachment-and-detachment determining section 24 is shown as a component different from the system control section 29.

As shown in FIG. 2, the electric contacts 15 connected to the two electric contacts 14 of the optical adapter 4 are connected to a contact "c" of a first switch 18*a* and a contact "c" of a second switch 18*b* of the switching circuit 18 by the two signal lines 17*a* and 17*b*, respectively. The second switch 18*b* performs functional display in FIG. 2 and specifically has a configuration shown in FIG. 3. The contact "c" of the first switch 18*a* is selectively connected to any one of a contact "a" connected to the attachment-and-detachment determining power supply 21 and a contact "b" connected to the LED turn-on power supply 22. On the other hand, the second switch 18*b* performs switching of a (open) state in which an electric current does not flow to the LED driving section 23 and a (closed) state in which an electric current flows to the LED driving section 23. As explained with reference to FIG. 1, the optical-adapter-attachment-and-detachment determining section 24 which determines attachment and detachment of the optical adapter 4 to and from the distal end portion 3 is connected to the signal line 17*b*.

For example, when the endoscope apparatus 1 is driven by a battery, a voltage and an electric current from a battery as a power supply for the entire endoscope apparatus are converted by plural power supply circuits into voltages and electric currents corresponding to the respective circuits. It goes without saying that power supplies in the present invention do not mean batteries but means the respective power supply circuits.

The optical-adapter-attachment-and-detachment determining section 24 electrically determines, using the attachment-and-detachment determining power supply 21, presence or absence of attachment and detachment of the optical adapter 4 in a state of the switching circuit 18 shown in FIG. 2 or a state of the switching circuit 18 shown in FIG. 3. When the optical-adapter-attachment-and-detachment determining section 24 determines that the optical adapter 4 is connected to the distal end portion 3, the system control section 29 performs switching of the switching circuit 18.

In the optical adapter 4, the LED 11 to which plural LED elements are connected in series is connected to the two electric contacts 14, and the resistor 12 for determination of attachment and detachment of the optical adapter 4 is connected to the two electric contacts 14 in parallel to the LED 11.

In the present embodiment, by connecting the resistor 12 for attachment and detachment determination in parallel to the LED 11 provided in the optical adapter 4, the number of electric contacts provided in the optical adapter 4 is reduced to two to make it possible to reduce a size of the optical adapter 4 and, even if the number of electric contacts is two, the endoscope apparatus can perform determination on attachment and detachment of the optical adapter 4 as explained below.

On the other hand, the signal line 17*a* connected to the electric contact 15 is connected to the contact "c" of the first switch 18*a* of the switching circuit 18, the contact "a" in the first switch 18*a* is connected to the attachment-and-detachment determining power supply 21, and the contact "b" is connected to the LED turn-on power supply 22.

The contact "c" of the first switch 18*a* is set to be ON with the contact "a" in an initial state as shown in FIG. 3. When the electric contacts 15 and 14 are connected, an electric current is supplied from the attachment-and-detachment determining power supply 21 to the optical-adapter-attachment-and-detachment determining section 24 side through the resistor 12.*of* the optical adapter 4.

The signal line 17*b* connected to the electric contact 15 is connected to one end of a resistor 31 included in the optical-adapter-attachment-and-detachment determining section 24. The other end of the resistor 31 is connected to a ground (GND) terminal through a resistor 32 and connected to, for example, a gate terminal of an FET (field effect transistor) 33 of an N-channel type. A drain terminal of the FET 33 is connected to a power supply terminal Vcc through a resistor 34 and connected to a voltage detection terminal of a voltage detection circuit 35. The source the terminal of the FET 33 is connected to the GND.

When the electric contacts 14 and the electric contacts 15 are connected as shown in FIG. 3, a voltage at a connection point of the resistor 31 and the resistor 32 is applied to a gate terminal of the FET 33. Consequently, the FET 33 is turned on from an OFF state to an ON state. The voltage detection circuit 35 changes from a state of the power supply terminal Vcc larger than 0V to a state in which a voltage 0V is detected and determines that the optical adapter 4 is connected. The voltage detection circuit 35 outputs a connection determination signal from an output terminal to the system control section 29. The system control section 29 controls switching of the switching circuit 18.

The signal line 17*b* is connected to a collector terminal of a transistor 37 of an NPN type included in the LED driving section 23. A base terminal of the transistor 37 is connected to the contact "c" of the second switch 18*b*.

The contact "a" in the second switch 18*b* is connected to the GND and the contact "b" is connected to the LED driving power supply. In an initial state, as shown in FIG. 3, the contact "c" of the first switch 18*a* is set to be connected to the contact "a" and the transistor 37 is OFF. An emitter terminal of the transistor 37 is connected to the GND, i.e., an earth potential through a resistor 38.

Operations in the present embodiment having such a configuration are explained below.

When electric power is supplied to the endoscope apparatus main body 5, i.e., at initial time, according to an output signal of the voltage detection circuit 35 included in the optical-adapter-attachment-and-detachment determining section 24 of the system control section 29, a connection state of the switching circuit 18 is set in a state in which the respective contacts "c" are connected to the respective contacts "a" as shown in FIG. 3. In other words, the first switch 18*a* is in a state of connection to the attachment-and-detachment determining power supply 21 and the second switch 18*b* is in a state in which an electric current from the LED driving section 23 does not flow. The initial state described above is a case in which a voltage at an input terminal of the voltage detection circuit 35 is the power supply terminal Vcc. In other words, as explained below, when the voltage at the input terminal changes to 0V, the system control section 29 performs an operation for switching a contact of the switching circuit 18 according to an output signal of the voltage detection circuit 35.

When the optical adapter 4 is connected to the distal end portion 3, a closed circuit (referred to as "closed circuit A1") included in a current path of the attachment-and-detachment determining power supply 21→the switch 18*a* of the switching circuit 18→the resistor 12 of the resistor element 13 of the optical adapter 4→the optical-adapter-attachment-and-detachment determining section 24 (the resistor 31→the resistor 32) is formed. The optical-adapter-attachment-and-detachment determining section 24 determines that the optical adapter 4 is connected to the distal end portion 3.

When a voltage of the attachment-and-detachment determining power supply 21 is set to be lower than Vf (a forward drop voltage) of the LED 11 of the optical adapter 4, the closed circuit A1 is formed. For example, in the case of a white LED, since an LED with a Vf of about 3.5V is used as the LED 11, it is preferable to set a voltage of the attachment-and-detachment determining power supply 21 to a voltage smaller than the Vf, for example, a constant voltage of about 2 to 3V.

A voltage applied to the resistor 32 is applied to a gate terminal of the FET 33 of the optical-adapter-attachment-and detachment determining section 24 and the FET 33 is turned on. When the FET 33 is turned on, the voltage detection circuit 35 detects the voltage of 0V (GND) and outputs a connection determination signal. The connection determination signal of the optical-adapter-attachment-and-detachment determining section 24 changes to a control signal via the system control section 29. The switching circuit 18 receives the control signal and is switched such that an electric current flows to a contact side different from a contact side at the initial time.

In the present embodiment, switching of the switching circuit 18 is performed according to the control signal of the system control section 29. However, an output signal of the optical-adapter-attachment-and-detachment determining section 24 as a part of the system control section 29 may directly control contact switching for the switching circuit 18.

When the contact of the switching circuit 18 is switched, a closed circuit of "the LED turn-on power supply 22→the switching circuit 18→the LED 11 of the optical adapter 4→the transistor 37 of the LED driving section 23→the resistor 38" is formed. The LED 11 of the optical adapter 4 is turned on.

Moreover, a closed circuit (referred to as "closed circuit B1") of "the LED turn-on power supply 22→the switching circuit 18→the LED 11 of the optical adapter 4→the resistor 31 to the resistor 32 of the optical-adapter-attachment-and-detachment determining section 24" is also formed. The optical-adapter-attachment-and-detachment determining section 24 continues to determine that the optical adapter 4 and the distal end portion 3 are connected. Therefore, a state in which the switching circuit 18 turns on the contact side different from the contact side at the initial time is maintained.

A resistance value of the resistor 12 of the resistor element 13 of the optical adapter 4 is set to, for example, a value (e.g., several hundred kΩ) 1000 times as large compared with a resistance (e.g., equal to or lower than about 100Ω) of the LED 11 at the time of the LED 11 lighting equal to or higher than Vf. Therefore, in the present embodiment, an electric current flowing to the resistor 12 at the time of the LED 11 lighting can be neglected because the electric current is very small compared with an electric current flowing to the LED 11. Therefore, since the resistor 12 can be considered opened, the closed circuit B1 is formed.

The second switch 18*b* of the switching circuit 18 is, as shown in FIG. 3, a switch inserted between the base terminal of the transistor 37 and the LED driving power supply or the GND. When the optical-adapter-attachment-and-detachment determining section 24 determines that the optical adapter 4 is connected to the distal end portion 3 and a terminal on the LED driving power supply of the second switch 18*b* is connected by the voltage detection circuit 35, electric power from the LED driving power supply is supplied to the base terminal of the transistor 37, the transistor 37 is turned on, and the collector terminal and the emitter terminal become conductive. On the other hand, when the optical adapter 4 is removed, the second switch 18*b* is connected to the GND. In other words, the collector terminal and the emitter terminal of the transistor 37 come into an open state while the transistor 37 keeps the turn-off state. In other words, the transistor 37 performs a switch operation represented by the second switch 18*b* of the switching circuit 18 shown in FIG. 2.

When the optical adapter 4 is connected to the distal end portion 3 and then removed from the distal end portion 3 in a state in which the LED 11 is on, a voltage is not applied to the gate terminal of the FET 33 of the optical-adapter-attachment-and-detachment determining section 24, and the FET 33 is turned off.

When the FET 33 is turned off, a voltage at the power supply terminal Vcc is inputted to the input terminal for voltage detection of the voltage detection circuit 35 through a resistor for pull-up 34. When the voltage at the power supply terminal Vcc is inputted to the input terminal of the voltage detection circuit 35, the voltage detection circuit 35 detects the voltage. Therefore, the optical-adapter-attachment-and-detachment determining section 24 determines that the optical adapter 4 and the distal end portion 3 are not connected with each other. According to an output signal of the voltage detection circuit 35, the system control section 29 performs contact switching to switch the first switch 18*a* and the second switch 18*b* of the switching circuit 18 to the state at the initial time. The LED turn-on power supply 22, which has power more than that of the attachment-and-detachment determining power supply 21, i.e., consumes more power than the attachment-and-detachment determining power supply 21, is not connected to the electric contacts 15.

The resistor 38 in the LED driving section 23 configures a constant current circuit in combination with the transistor 37. When the optical adapter 4 is connected and the LED 11 is turned on, a voltage indicated by Va=VB−VBE is applied to the resistor 38. VB represents a base voltage of the transistor 37, i.e., a voltage of the LED driving power supply and VBE represents a voltage between the base terminal and the emitter terminal of the transistor 37. In other words, an electric current I indicated by I=Va/(resistance R of the resistor 38) flows to the resistor 38. The electric current I flows to the LED 11 as well because the transistor 37 is turned on. The LED driving section 23 configures a constant current circuit which drives the LED 11 with the electric current I. Therefore, if a resistance of the resistor 38 is set to an appropriate value, the LED 11 can be turned on with an appropriate electric current.

When the optical adapter 4 is removed from the distal end portion 3 in a state in which the LED 11 is on, the optical-adapter-attachment-and-detachment determining section 24 determines that the optical adapter 4 is removed from the distal end portion 3. The system control section 29 switches the first switch 18*a* of the switching circuit 18 to the attachment-and-detachment determining power supply 21 side and switches the second switch 18*b* thereof to an open state as shown in FIG. 2. The system control section 29 enters a waiting state for the optical adapter 4 to be connected to the distal end portion 3 again.

Next, operations of the system control section 29 according to the present embodiment are explained with reference to a flowchart of FIG. 4.

At the initial time when electric power is supplied to the endoscope apparatus main body 5, the switching circuit 18 is in the connection state at the initial time shown in FIG. 2 or FIG. 3 according to an output signal of the voltage detection circuit 35 included in the optical-adapter-attachment-and-detachment determining section 24. In other words, as shown in step S1 in FIG. 5, the attachment-and-detachment determining power supply 21 side is selected for the first switch 18*a*. The second switch is in the open state (see FIG. 2) in which an electric current does not flow to the LED driving section 23.

In step S2, the optical-adapter-attachment-and-detachment determining section 24 enters the waiting state for the optical adapter 4 to be connected to the distal end portion 3.

When the optical adapter 4 is connected to the distal end portion 3, the closed circuit A1 of "the attachment-and-detachment determining power supply 21→the first switch 18*a* of the switching circuit 18→the resistor 12 of the resistor element 13 of the optical adapter 4→the resistor 31 to the resistor 32 of the optical-adapter-attachment-and-detachment determining section 24" is formed. The optical-adapter-attachment-and-detachment determining section 24 determines that the optical adapter 4 is connected to the distal end portion 3. Since a voltage of the attachment-and-detachment determining power supply 21 is set to be equal to or lower than Vf (the forward drop voltage) of the LED 11 of the optical adapter 4, the closed circuit A1 is formed. Since a voltage applied to the resistor 32 is applied to the gate terminal of the FET 33 of the optical-adapter-attachment-and-detachment determining section 24, the FET 33 is turned on. When the FET 33 is turned on, a voltage at the input terminal of the voltage detection circuit 35 changes to 0 V (GND). The voltage detection circuit 35 detects the voltage 0 V at the input terminal of the voltage detection circuit 35 and outputs a connection determination signal from the output terminal thereof to the system control section 29.

In the next step S3, the system control section 29 performs control of the switching circuit 18. In the switching circuit 18, the first switch 18*a* is switched to the LED turn-on power supply 22 side, and the second switch 18*b* is switched to the closed state. In other words, the first switch 18*a* and the second switch 18*b* of the switching circuit 18 is subjected to switching processing such that the contact "b" side different from that in the state at the initial time is connected. Then, the transistor 37 is turned on, and a path through which an electric current by the LED turn-on power supply 22 flows to the LED driving section 23 side through the collector element and the emitter element of the transistor 37 is formed. As shown in step S4, an electric current flows to the LED 11 and the LED 11 is turned on. When the LED 11 is turned on, an operator can insert the insertion section 2 into the inside of an inspection object and inspect the inspection object.

When the LED 11 enters a lighting state, as shown in step S5, the optical-adapter-attachment-and-detachment determining section 24 always makes determination on whether the optical adapter 4 is removed from the distal end portion 3. When the optical adapter 4 is removed from the distal end portion 3, as shown in step S6, the LED 11 is turned off. When the optical adapter 4 is removed from the distal end portion 3, since the closed circuit B1 is not formed, the FET 33 of the optical-adapter-attachment-and-detachment determining section 24 is turned off. Therefore, the voltage detection circuit 35 determines that the optical adapter 4 is removed from the distal end portion 3.

In the next step S7, the system control section 29 performs control of switching processing for the switching circuit 18 according to an output signal of the optical-adapter-attachment-and-detachment determining section 24. In other words, the system control section 29 performs control for switching the first switch 18*a* to the attachment-and-detachment determining power supply 21 side and switching the first switch 18*b* to the open state and switches the switching circuit to the state at the initial time. The system control section 29 repeats the processing from step S2.

According to the present embodiment in which the operations are performed as described above, the number of electric contacts provided in the optical adapter 4 mounted with the resistor element 3 including the LED 11 as a luminous body is reduced to two, and the number of signal lines is also reduced to two. Therefore, it is possible to realize a reduction in size and a reduction in diameter of the optical adapter 4.

According to the present embodiment, the number of contacts necessary for the distal end portion 3 to which the optical adapter 4 is detachably attachable is also reduced to two to make it possible to set the number of signal lines necessary for the distal end portion 3 to two. Therefore, it is possible to realize a reduction in diameter of the insertion section 2 and realize a reduction in diameter and a reduction in size of the distal end portion.

During making a determination on attachment and detachment of the optical adapter 4, the low-power consumption attachment-and-detachment determining power supply 21 is subjected to constant voltage control by the switching circuit 18 in the endoscope apparatus main body 5 to make the determination on attachment and detachment. When the optical adapter 4 is connected, the attachment-and-detachment determining power supply 21 is switched to the LED turn-on power supply 22 for turning on the LED 11 and the LED turn-on power supply 22 is subjected to constant current control. Consequently, the endoscope apparatus 1 realizes power saving as well.

Attachment and detachment determination using the LED turn-on power supply 22 is also possible. However, by using the attachment-and-detachment determining power supply 21 which consumes less power than the LED turn-on power supply 22, it is possible to reduce power consumption when the optical adapter 4 is not connected.

The endoscope apparatus 1 according to the present embodiment has the attachment-and-detachment determining power supply 21 exclusively used for attachment and detachment determination and the LED turn-on power supply 22 exclusively used for LED lighting. Therefore, a circuit configuration of the endoscope apparatus is simple and control of the endoscope apparatus is easy. In other words, since the attachment-and-detachment determining power supply 21 is subjected to constant voltage control and the LED turn-on power supply 22 is subjected to constant current control, it is preferable to use dedicated power supplies as these power supplies, respectively.

Moreover, by setting a voltage of the attachment-and-detachment determining power supply 21 to a value smaller than the forward drop voltage of the LED 11, it is possible to realize power saving for the endoscope apparatus 1 and prevent an adverse effect due to a transient current during attachment and detachment of the optical adapter 4.

The optical-adapter-attachment-and-detachment determining section 24 or the voltage detection circuit 35 of the optical-adapter-attachment-and-detachment determining section 24 can be configured by a comparator, an FET, or the like but can also be configured by an integrated circuit component such as a CPU. It is also preferable to configure the system control section 29 including the optical-adapter-attachment-and-detachment determining section 24 with one CPU. The switching circuit 18 can be configured by a relay, a photo-coupler, a photo-MOS relay, an FET, a transistor, or the like.

<Second Embodiment>

Figure 5:
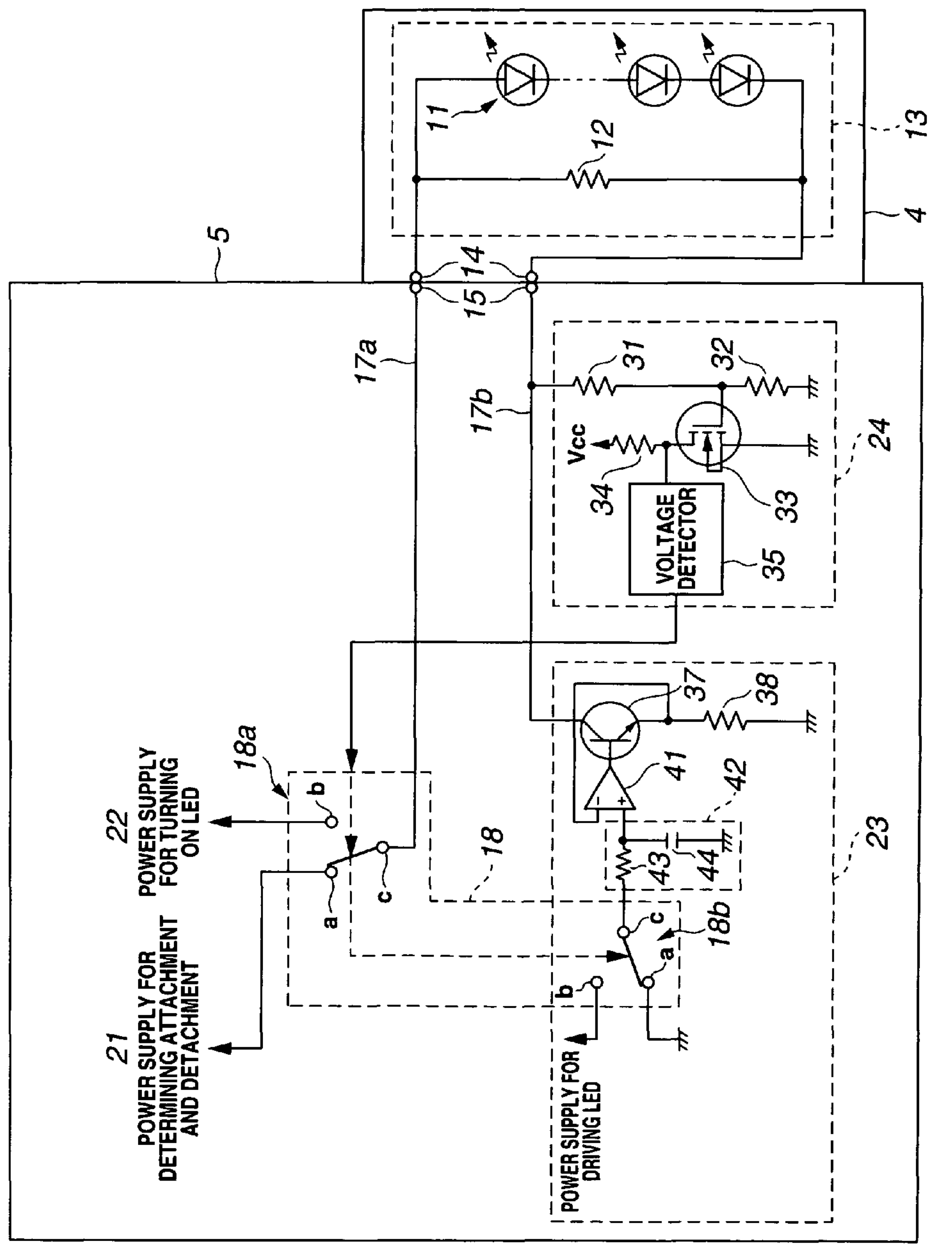
FIG. 5 is a circuit diagram showing a circuit configuration of a main part in an endoscope apparatus according to a second embodiment of the present invention.

Next, a second embodiment of the present invention is explained with reference to FIG. 5. FIG. 5 shows a circuit configuration of a main part in an endoscope apparatus according to the second embodiment.

A configuration of the endoscope apparatus according to the present embodiment shown in FIG. 5 is configured by adding an operational amplifier 41 and an integrating circuit 42 to the LED driving section 23 of a configuration shown in FIG. 3.

According to the addition of the operational amplifier 41, the endoscope apparatus according to the present embodiment can compensate for a change in VBE due to temperature fluctuation of the transistor 37 when the transistor 37 is turned on and the LED 11 is on. Therefore, it is possible to configure a more highly accurate constant current circuit.

The integrating circuit 42 is configured by a resistor 43 and a capacitor 44 and can delay a voltage applied to the base of the transistor 37. Therefore, the endoscope apparatus according to the present embodiment can gradually increase an electric current flowing to the LED 11, i.e., gradually increase a light amount of the LED.

Since components of the endoscope apparatus according to the second embodiment other than the above are the same as those of the endoscope apparatus according to the first embodiment, explanation of the components is omitted.

According to the present embodiment, other than the actions and effects according to the first embodiment, it is possible to compensate for a change in VBE due to temperature fluctuation of the transistor 37 and highly accurately turn on the LED 11 with an optimum electric current. According to the present embodiment, it is possible to prevent, using a delay section formed by the integrating circuit 42, an undesirable transient electric current from flowing when the LED 11 is turned on or turned off.

<Third Embodiment>

Figure 6:
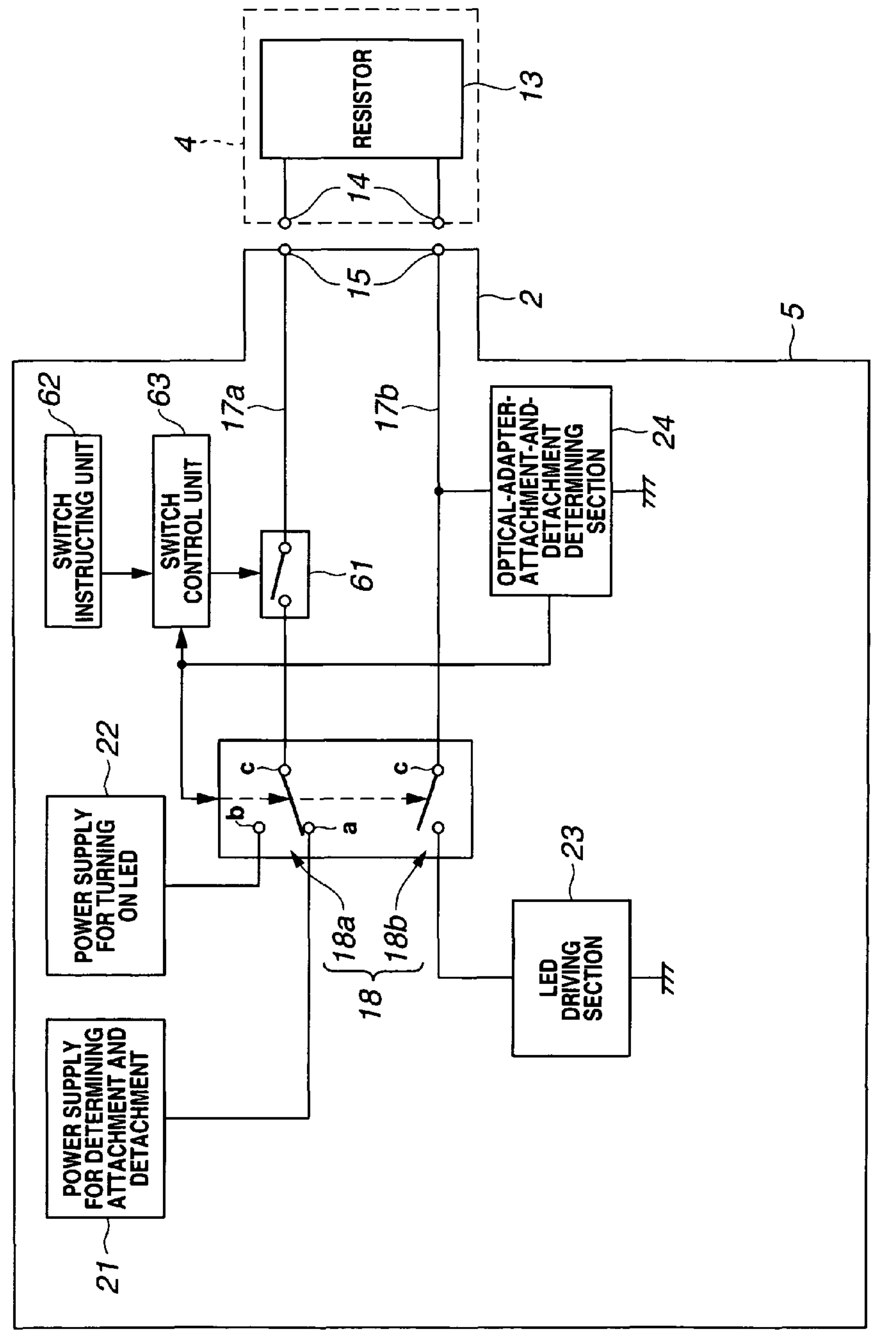
FIG. 6 is a block diagram showing a configuration of a main part in an endoscope apparatus according to a third embodiment of the present invention.
Figure 7:
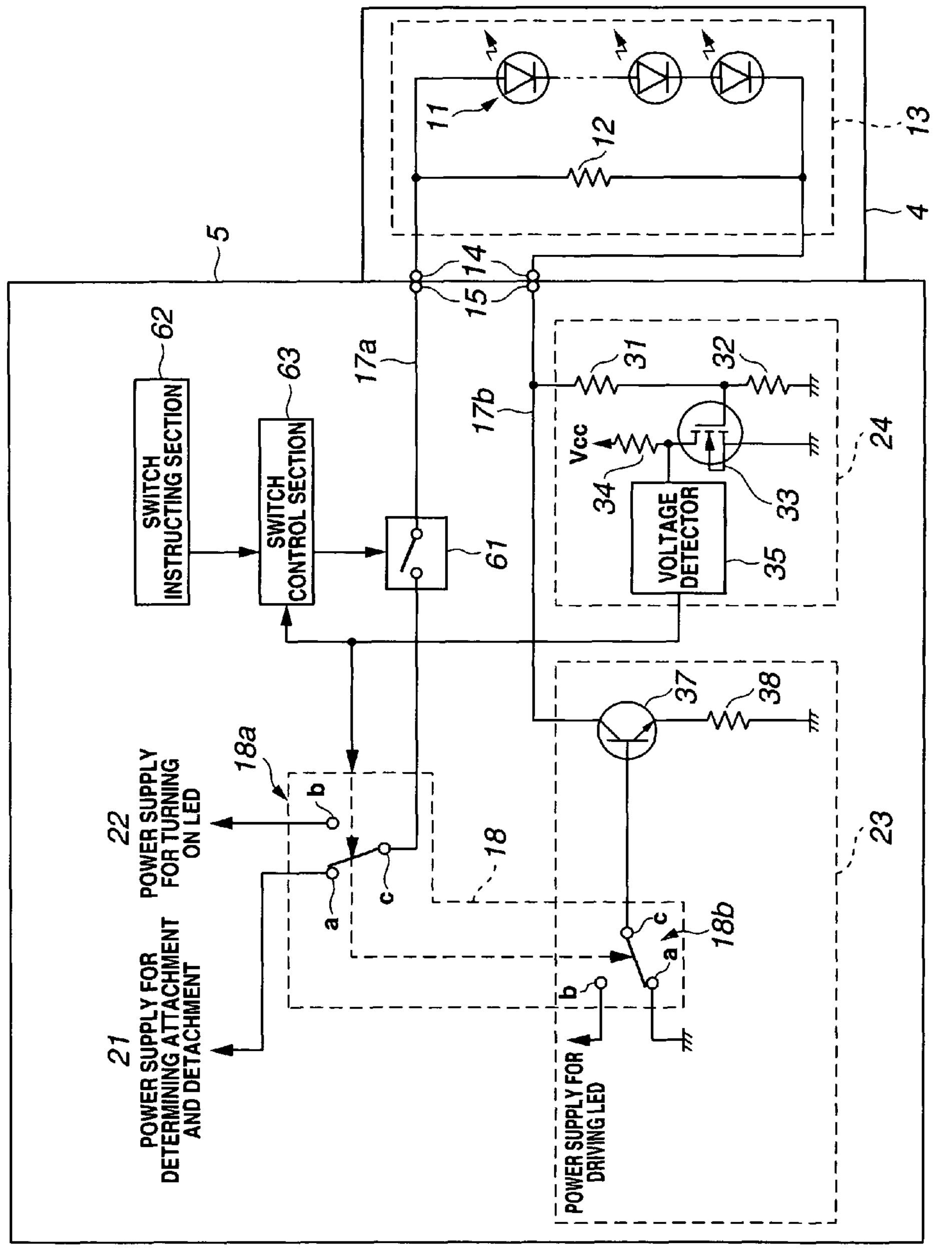
FIG. 7 is a circuit diagram showing a more specific circuit configuration of FIG. 6.
Figure 8:
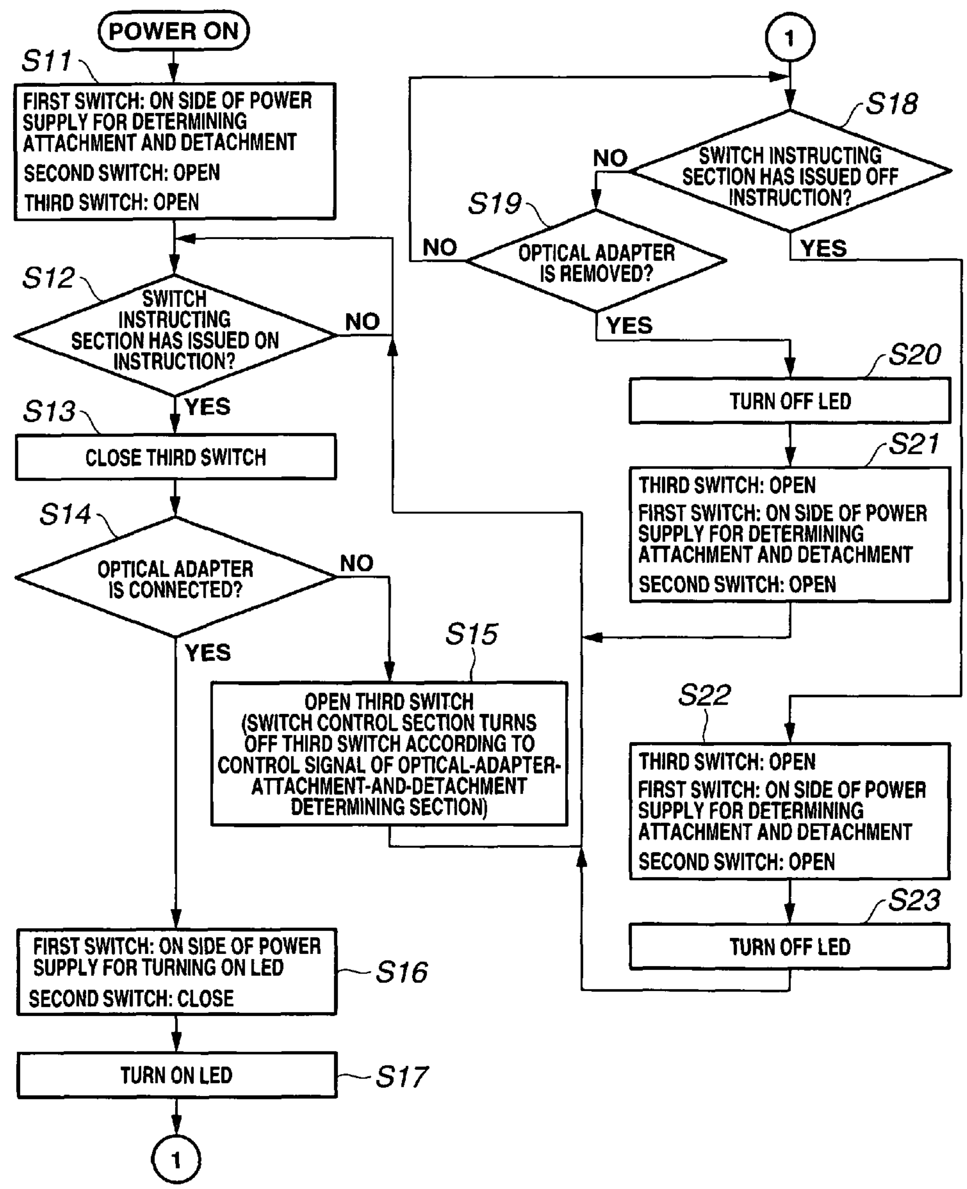
FIG. 8 is a flowchart showing operation contents according to the third embodiment of the present invention.

Next, a third embodiment of the present invention is explained with reference to FIG. 6 to FIG. 8. FIG. 6 shows a block configuration of a main part in an endoscope apparatus according to the third embodiment. FIG. 7 shows a more detailed configuration of FIG. 6.

The endoscope apparatus according to the present embodiment shown in FIG. 6 configured by adding, to the configuration of the endoscope apparatus according to the first embodiment, a third switch 61 provided along the signal line 17*a*, a switch instructing section 62 which performs ON/OFF instruction for the third switch 61, and a switch control section 63 which performs ON/OFF control for the third switch 61 according to an instruction of the switch instructing section 62.

The system control section 29 controls the switching circuit 18 as in the first embodiment and outputs a control signal to the switch control section 63 on the basis of a signal of the voltage detection circuit 35 of the optical-adapter-attachment-and-detachment determining section 24. The switch control section 63 controls ON/OFF (a closed state/an open state) of the third switch 61 according to the control signal from the system control section 29. Components of the endoscope apparatus according to the present embodiment other than the above are the same as those in the first embodiment.

Only differences from the first embodiment are explained below.

In the endoscope apparatus, for example, when an ON instruction for the third switch is inputted to the switch control section 63 by the switch instructing section 62 such as a momentary switch on the user interface 7 shown in FIG. 1 in a state in which the optical adapter 4 is not connected to the distal end portion 3, the switch control section 63 switches the third switch 61 to the closed state.

When the optical adapter 4 is not connected to the distal end portion 3, the system control section 29 does not send a control signal to the switching circuit 18. A connection state of the contacts of the switching circuit 18 is the same as that shown in FIG. 6 or FIG. 7, i.e., the contact "a" side is in the connection state. At the same time, the system control section 29 sends a control signal to the switch control section 63 and switches the third switch 61 to the open state. In other words, in a state in which the optical adapter 4 is connected to the distal end portion 3, unless a user does not perform an ON operation instruction from the switch instructing section 62, a voltage is not applied to the electric contacts 14 of the optical adapter 4 at all.

When an ON instruction is inputted to the switch control section 63 from the switch instructing section 62 in a state in which the optical adapter 4 is connected, the third switch 61 is switched to the closed state.

In the case of the state, a closed circuit of "the attachment-and-detachment determining power supply 21→the switching circuit 18→the third switch 61→the resistor 12 of the optical adapter 4→the optical-adapter-attachment-and-detachment determining section 24" is formed. The optical-adapter-attachment-and-detachment determining section 24 determines that the optical adapter 4 is connected.

The system control section 29 sends a control signal to the switching circuit 18 and switches the first switch 18*a* of the switching circuit 18 to the LED turn-on power supply 22 side and switches the second switch 18*b* to a close side, i.e., a side for driving the LED driving section 23.

Consequently, a closed circuit of "the LED turn-on power supply 22→the first switch 18*a* of the switching circuit 18→the third switch 61→the LED 11 of the optical adapter 4→the second switch 18*b* of the switching circuit 18→the LED driving section 23" is formed and the LED 11 of the optical adapter 4 is turned on.

Moreover, a closed circuit of "the LED turn-on power supply 22→the switching circuit 18→the LED 11 of the optical adapter 4→the optical-adapter-attachment-and-detachment determining section 24" is also formed. As long as the optical-adapter-attachment-and-detachment determining section 24 continues to determine that the optical adapter 4 is connected, the system control section 29 continues to connect the first switch 18*a* of the switching circuit 18 to the LED turn-on power supply 22 side and connect the second switch 18*b* to the LED driving section 23 side, i.e., a side on which the LED driving section 23 performs a driving operation.

When the optical adapter 4 is removed from the distal end portion 3 in a state in which the LED of the optical adapter 4 is on, the LED 11 of the optical adapter 4 is turned off and the optical-adapter-attachment-and-detachment determining section 24 determines that the optical adapter 4 is removed from the distal end portion 3. The system control section 29 sends a control signal to the switching circuit 18, switches the first switch 18*a* of the switching circuit 18 to the attachment-and-detachment determining power supply 21 side, and switches the second switch 18*b* to the open state. At the same time, the system control section 29 sends a control signal to the switch control section 63. The switch control section 63 turns off the third switch 61.

The voltage detection circuit 35 and the switch control section 63 can also be realized by being configured by a comparator, an FET, an AD converter, or the like but can also be realized by an integrated circuit such as a CPU. The switching circuit 18 can be realized by a relay, a photocoupler, a photo-MOS relay, an FET, a transistor, or the like.

Moreover, the circuit configuration shown in FIG. 7 can be changed to a circuit configuration in which the operational amplifier 41 and the integrating circuit 42 are added as in the second embodiment shown in FIG. 5.

Next, a flow of processing according to the present embodiment is explained with reference to a flowchart of FIG. 8.

When electric power is supplied to the endoscope apparatus, in step S11, as an initial state, the first switch 18*a* of the switching circuit 18 is controlled to the attachment-and-detachment determining power supply side and the second switch 18*b* is controlled to the open state. The third switch 61 is controlled into the open state.

In step S12, the switch control section 63 comes to a standby state in which the switch control section 63 waits for an ON instruction for the third switch to be outputted from the switch instructing section 62. When the ON instruction is outputted from the switch instructing section 62, in step S13, the switch control section 63 switches the third switch 61 to the closed state.

Then, in step S14, the optical-adapter-attachment-and-detachment determining section 24 performs determination on whether the optical adapter 4 is connected to the distal end portion 3.

When the optical-adapter-attachment-and-detachment determining section 24 determines that the optical adapter 4 is not connected to the distal end portion 3, as shown in step S15, the third switch 61 is controlled to the open state. In other words, after the third switch 61 is controlled to the open state via the switch control section 63 by the system control section 29 on the basis of a signal of the optical-adapter-attachment-and-detachment determining section 24, the processing returns to step S12.

On the other hand, when the optical-adapter-attachment-and-detachment determining section 24 determines that the optical adapter 4 is connected, the processing proceeds to step S16. The system control section 29 switches the first switch 18*a* of the switching circuit 18 to the LED turn-on power supply 22 side and closes the second switch 18*b* according to a control signal.

Consequently, as shown in step S17, an electric current flows to the LED 11 and the LED 11 is turned on. The user can insert the insertion section 2 into the inside of an inspection object and perform an endoscope inspection.

When the LED 11 enters a lighting state in the way, as shown in step S18, the switch control section 63 enters a standby state for waiting for a third switch OFF instruction to be outputted from the switch instructing section 62.

When the OFF instruction is not outputted from the switch instructing section 62, as shown in step S19, the optical-adapter-attachment-and-detachment determining section 24 determines whether the optical adapter 4 is not removed from the distal end portion 3. When the optical adapter 4 is not removed from the distal end portion 3, the processing returns to step S18.

Conversely, when the optical adapter 4 is removed from the distal end portion 3, as shown in step S20, the LED 11 is turned off.

As shown in step S21, the switch control section 63 switches the third switch 61 to the open state on the basis of a result of the determination of the optical-adapter-attachment-and-detachment determining section 24 that the optical adapter 4 is removed from the distal end portion 3. The system control section 29 switches the first switch 18*a* of the switching circuit 18 to the attachment-and-detachment determining power supply 21 side and switches the second switch 18*b* thereof to the open state. Then, the system control section 29 starts the processing in step S12.

On the other hand, when the OFF instruction is outputted from the switch instructing section 62 in step S18, processing same as that in step S21 is performed in step S22. As shown in step S23, the LED 11 is turned off. The system control section 29 starts the processing in step S12.

According to the present embodiment in which the operations described above are performed, the effects same as those in the first embodiment are realized. Moreover, supply of an electric current to the optical adapter 4 side and stop of the supply can be controlled according to an instruction of the user. Therefore, the endoscope apparatus according to the third embodiment is convenient and can realize further energy saving.

<Fourth Embodiment>

Figure 9:
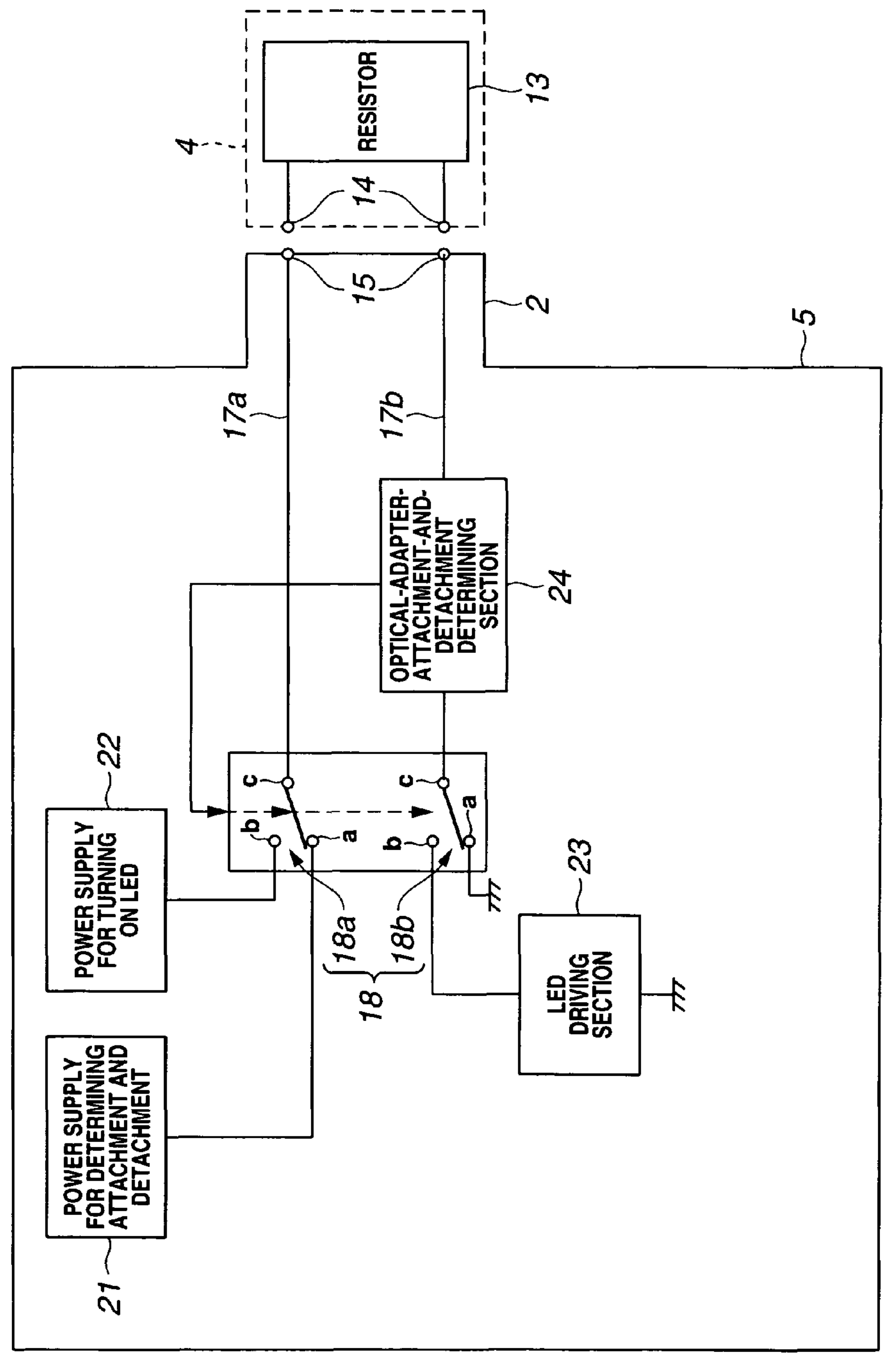
FIG. 9 is a block diagram showing a configuration of a main part in an endoscope apparatus according to a fourth embodiment of the present invention.
Figure 10:
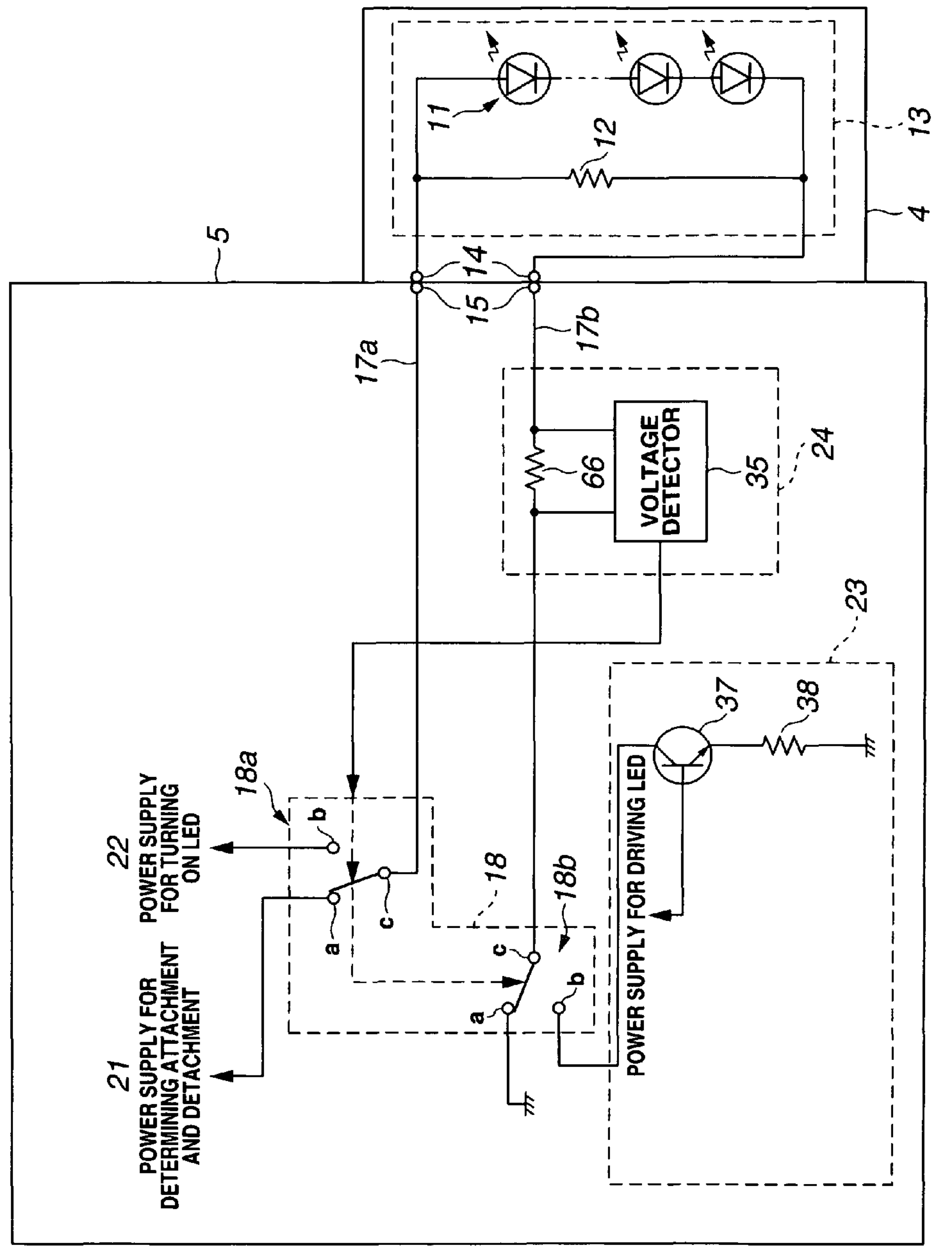
FIG. 10 is a circuit diagram showing a more specific circuit configuration of FIG. 9.

Next, a fourth embodiment of the present invention is explained with reference to FIG. 9 and FIG. 10. FIG. 9 shows a block configuration of a main part in an endoscope apparatus according to the present embodiment. The endoscope apparatus according to the present embodiment has the optical-adapter-attachment-and-detachment determining section 24 having a configuration different from that according to the first embodiment and the like. In other words, in the endoscope apparatus according to the present embodiment, the optical-adapter-attachment-and-detachment determining section 24 is provided in the signal line 17*b*. FIG. 10 more specifically shows the configuration shown in FIG. 9. As shown in FIG. 10, in the endoscope apparatus according to the present embodiment, the optical-adapter-attachment-and-detachment determining section 24 which performs attachment and detachment determination for the optical adapter 4 by detecting, in the voltage detection circuit 35, an electric current flowing at both ends of a resistor 66 for attachment and detachment determination is formed.

When the optical-adapter-attachment-and-detachment determining section 24 detects the electric current flowing at both the ends of the resistor 66, the system control section 29 controls the switching circuit 18 to turn on the LED 11 on the basis of an output signal of the voltage detection circuit 35.

The signal line 17*b* connected to the electric contact 15 at one end is connected to the contact "c" of the second switch 18*b* at the other end through the resistor 66. The contact "a" of the second switch 18*b* is connected to the GND and the contact "b" thereof is connected to the collector terminal of the transistor 37 included in the LED driving section 23. The base terminal of the transistor 37 is connected to the LED driving power supply, and the emitter terminal thereof is connected to the GND potential through the resistor 38. Other components of the endoscope apparatus according to the present embodiment are the same as those in the first embodiment.

The endoscope apparatus according to the present embodiment has actions and effects substantially the same as those in the first embodiment and the like.

The voltage detection circuit 35 can be realized by being configured by a comparator, an FET, an AD converter, or the like but can also be realized by a component such as a CPU.

In the present embodiment, it is also preferable to make the attachment-and-detachment determining power supply 21 as a negative power supply. By making the attachment-and-detachment determining power supply 21 as a negative power supply, a reverse bias is applied to the LED 11 in the optical adapter 4. Therefore, a range of preferable voltage values of the attachment-and-detachment determining power supply 21 is not limited by a value of the forward drop voltage of the LED 11.

Moreover, in the present embodiment, it is also possible to adopt a circuit configuration in which the operational amplifier 41 and the integrating circuit 42 are added as in the second embodiment, adopt a circuit configuration in which the third switch 61, the switch instructing section 62, and the switch control section 63 are added as in the third embodiment, and adopt a circuit configuration as a combination of the second embodiment and the third embodiment in which the operational amplifier 41, the integrating circuit 42, the third switch 61, the switch instructing section 62, and the switch control section 63 are added.

<Fifth Embodiment>

Figure 11:
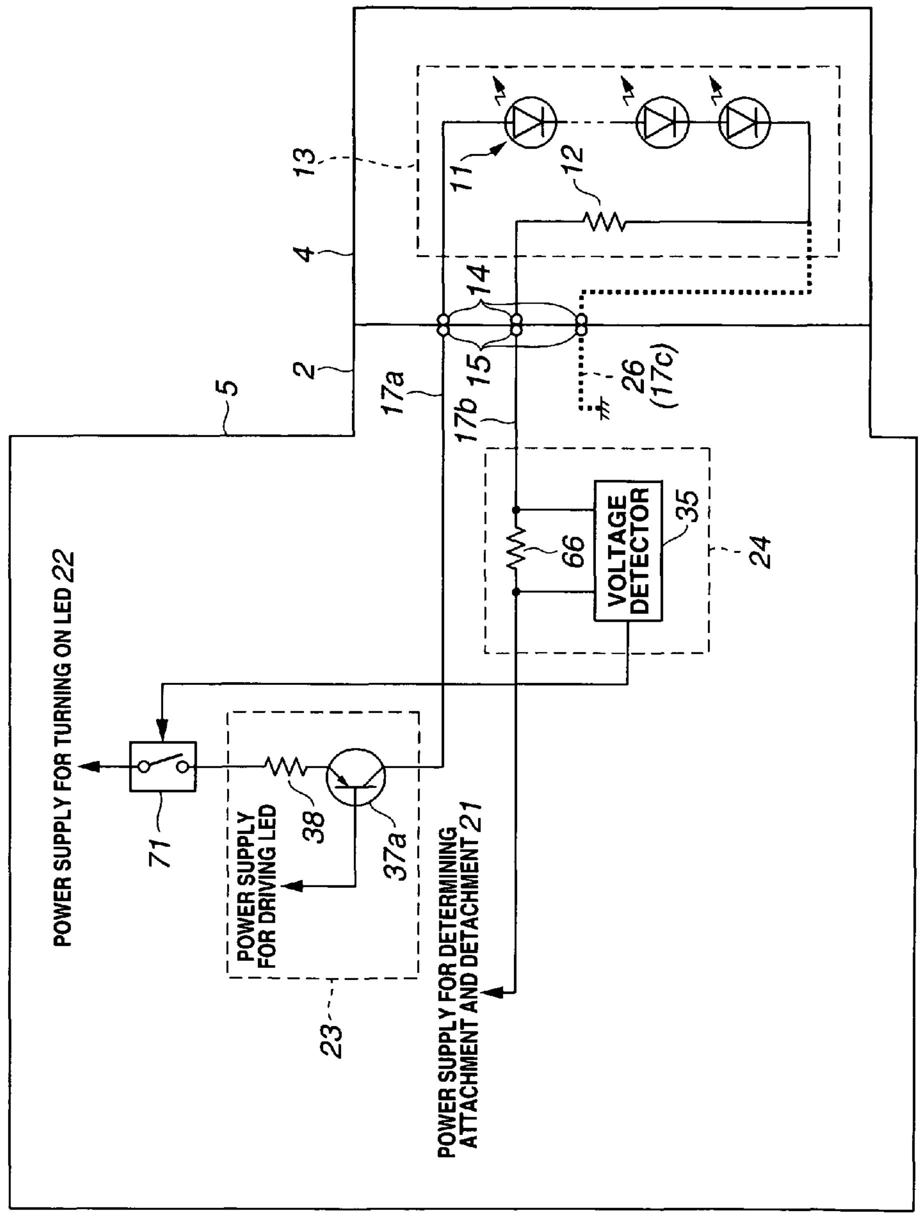
FIG. 11 is a circuit diagram showing a configuration of a main part in an endoscope apparatus according to a fifth embodiment of the present invention.

Next, a fifth embodiment of the present invention is explained with reference to FIG. 11. FIG. 11 shows a configuration of a main part in an endoscope apparatus according to the fifth embodiment. In the present embodiment, the number of electric contacts 14 of the optical adapter 4 is increased to three in appearance and the number of electric contacts 15 on the insertion section 3 side is also increased to three in appearance in association with the number of electric contacts 14.

A cathode of the LED 11 in the optical adapter 4 and one terminal of the resistor 12 of the resistor element 13 are connected to a common GND and connected to one electric contact 14 among the three electric contacts 14. An anode of the LED 11 and the other terminal of the resistor 12 are connected to the different electric contacts 14, respectively.

On the endoscope apparatus main body 5 side, the signal line 17*a* connected to the electric contact 15 connected to the electric contact 14 connected to the anode of the LED 11 is connected to the LED driving section 23. The LED driving section 23 configures a constant current circuit of a discharge type different from an intake type according to the first to fourth embodiments.

In other words, the signal line 17*a* is connected to a collector of a transistor 37*a* of a PNP type included in the LED driving section 23. One end of the resistor 38 is connected to an emitter of the transistor 37*a*. A base of the transistor 37*a* is connected to the LED driving power supply. The other end of the resistor 38 is connected to the LED turn-on power supply 22 via the switch 71.

As in the case of the fourth embodiment, the resistor 66 is connected to a part of the signal line 17*b*. The optical-adapter-attachment-and-detachment determining section 24 which performs attachment and detachment determination for the optical adapter 4 by detecting voltages at both the ends of the resistor 66 using the voltage detection circuit 35 is formed. The resistor 66 is connected to the attachment-and-detachment determining power supply 21. The electric contact 15 connected to the electric contact 14 for GND is connected to the GND through a signal line 17*c*.

Operations in the present embodiment with such a configuration are explained.

When the optical adapter 4 is connected to the distal end portion 3, the voltage detection circuit 35 of the optical-adapter-attachment-and-detachment determining section 24 detects that voltages are generated at both the ends of the resistor 66 to thereby determine that the optical adapter 4 is connected to the distal end portion 3.

The voltage detection circuit 35 switches a switch 71 from an open state to a closed state (an ON state). Then, an electric current flows from the LED turn-on power supply 22 to the switch 71, the LED driving section 23, the signal line 17*a*, the LED 11, and the GND, and the LED 11 is turned on.

When the LED 11 enters a lighting state in the way, the optical-adapter-attachment-and-detachment determining section 24 monitors removal of the optical adapter 4 from a state of connection to the distal end portion 3. When the optical adapter 4 is removed from the distal end portion 3, the LED 11 is turned off. The optical-adapter-attachment-and-detachment determining section 24 detects the removal of the optical adapter 4 from the distal end portion 3. The system control section 29 switches the switch 71 from the closed state to the open state according to an output signal of the optical-adapter-attachment-and-detachment determining section 24.

The processing returns to the initial state. The optical-adapter-attachment-and-detachment determining section 24 enters a waiting state for the optical adapter 4 to be connected to the distal end portion 3.

According to the present embodiment, the system control section 29 can always perform, without performing switching of the two power supplies using the switching circuit 18 according to the first embodiment and the like, determination on attachment and detachment of the optical adapter 4 to and from the distal end portion 3 using the attachment-and-detachment determining power supply 21, when the optical adapter 4 is connected to the distal end portion 3, supply electric power for turning on the LED from the LED turn-on power supply 22, and turn on the LED 11 with an appropriate electric current.

In the present embodiment, the number of electric contacts 14 of the optical adapter 4 and the number of electric contacts 15 on the distal end portion 3 side are three in appearance. However, the GND line in the signal line 26 connected to the CCD 16 is used as the signal line 17*c* used as the GND. Therefore, the number of signal lines used for attachment and detachment determination is two. The number of electric contacts 14 of the optical adapter 4 and the number of electric contacts 15 on the endoscope apparatus main body 5 side are practically two.

The switch instructing section 62 and the switch control section 63 may be provided in the endoscope apparatus according to the present embodiment as shown in the circuit diagram (see FIG. 7) of the third embodiment, and the third switch 61 may be inserted between the attachment-and-detachment determining power supply 21 and the resistor 66 to control the switch control section 63 according to a result of determination of the optical-adapter-attachment-and-detachment determining section 24.

The voltage detection circuit 35 of the optical-adapter-attachment-and-detachment determining section 24 can also be configured by a comparator, an A-D converter, or the like. The transistor 37*a* can also be configured by an FET, a relay, a photo-coupler, or a photo-MOS relay.

<Sixth Embodiment>

Figure 12:
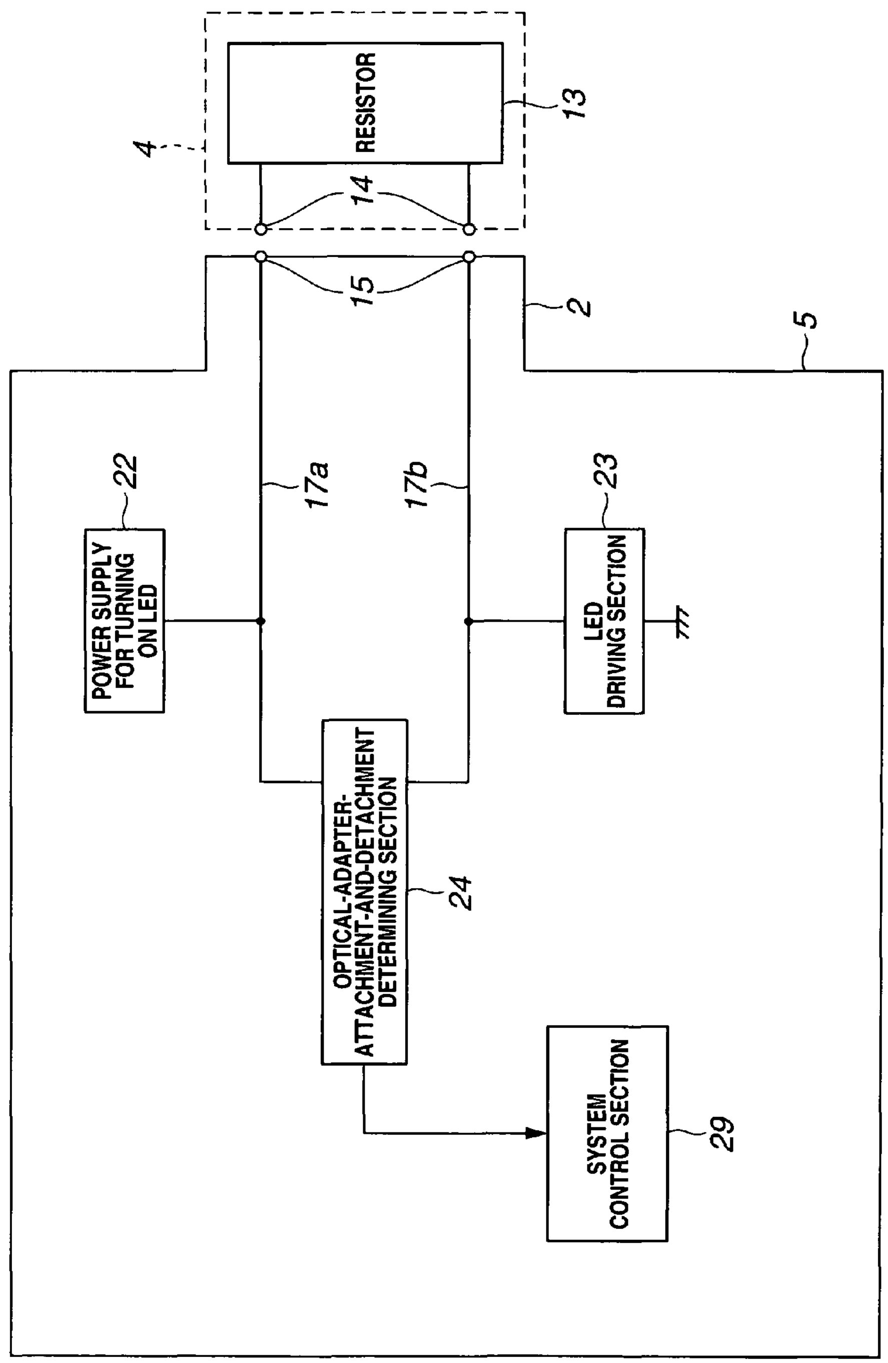
FIG. 12 is a block diagram showing a configuration of a main part in an endoscope apparatus according to a sixth embodiment of the present invention.

Next, a sixth embodiment of the present invention is explained with reference to FIGS. 12 and 13. FIG. 12 shows a block configuration of a main part in an endoscope apparatus according to the sixth embodiment.

In the first to fourth embodiments, the switching circuit 18 is provided because the two signal lines 17*a* and 17*b* are used. However, in the present embodiment, attachment and detachment of the optical adapter 4 is determined and the LED 11 is turned on by the two signal lines 17*a* and 17*b* without using the switching circuit 18. The endoscope apparatus main body 5 according to the present embodiment has a configuration in which the optical-adapter-attachment-and-detachment determining section 24 which determines attachment and detachment of the optical adapter 4 is provided between the signal lines 17*a* and 17*b* without providing the switching circuit 18 in the endoscope apparatus main body 5 shown in FIG. 2. In the present embodiment, the attachment-and-detachment determining power supply 21 shown in FIG. 2 is not provided. The LED turn-on power supply 22 is connected to the signal line 17*a* and the LED driving section 23 is connected to the other signal line 17*b*. In FIG. 12, an output signal of the optical-adapter-attachment-and-detachment determining section 24 is sent to the system control section 29.

Figure 13:
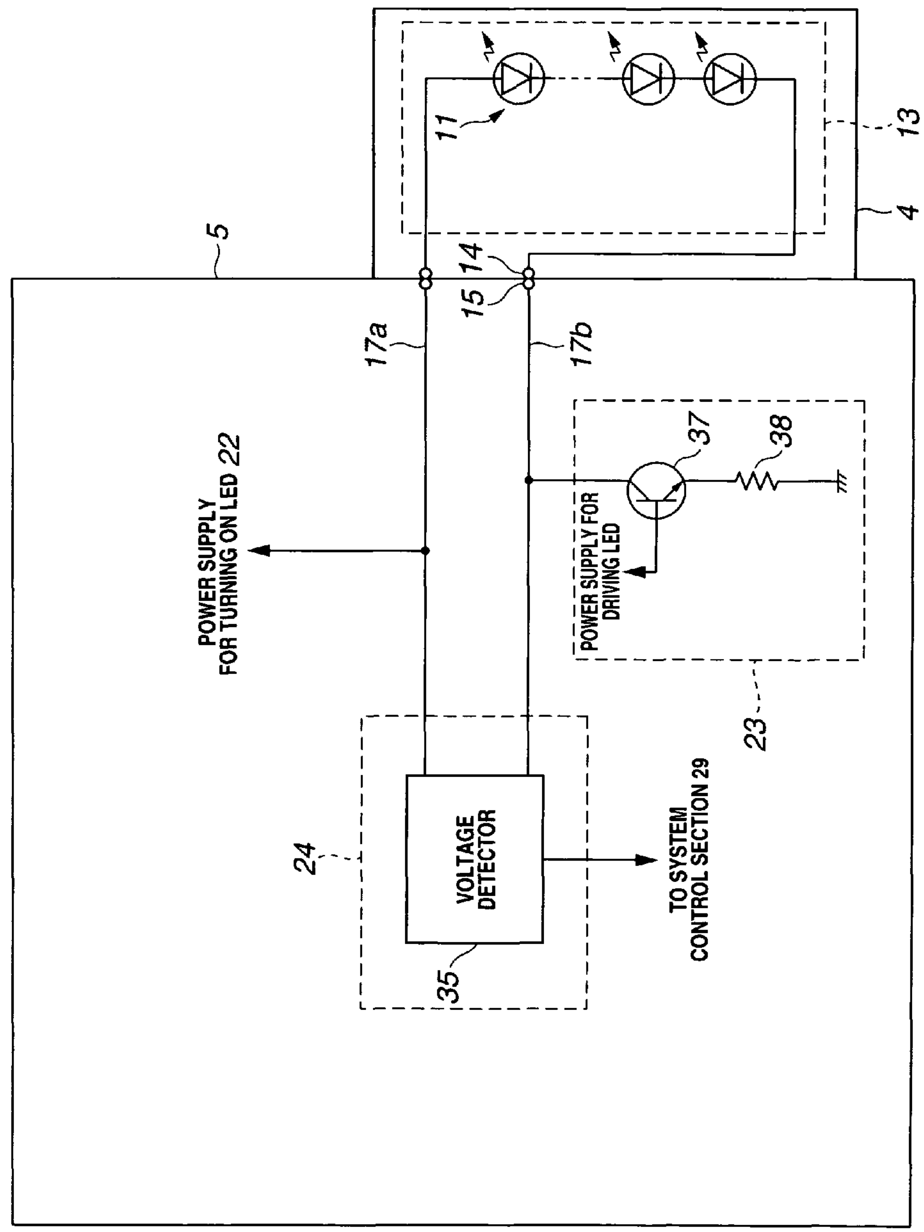
FIG. 13 is a circuit diagram showing a more specific circuit configuration of FIG. 12.

A more detailed configuration of the respective sections shown in FIG. 12 is shown in FIG. 13.

As shown in FIG. 13, in the optical adapter 4 according to the present embodiment, the resistor 12 shown in FIG. 3 is not provided. In other words, in the optical adapter 4 according to the present embodiment, the LED 11 is connected between the two electric contacts 14 (when there are plural LED elements, the LED elements are connected in series).

In the endoscope apparatus main body 5 according to the present embodiment, the optical-adapter-attachment-and-detachment determining section 24 to which the voltage detection circuit 35 is connected and which determines attachment and detachment of the optical adapter 4 is formed between the signal line 17*a* and the signal line 17*b* in the endoscope apparatus main body 5 shown in FIG. 3.

A configuration of the LED driving section 23 is the same as that of the LED driving section 23 shown in FIG. 3. A voltage of the LED driving power supply is always applied to the base terminal of the transistor 37 included in the LED driving section 23. When the electric contacts 14 of the optical adapter 4 are connected to the electric contacts 15 on the endoscope apparatus main body 5 side, the collector terminal and the emitter terminal of the transistor 37 of the LED driving section 23 become conductive, and an electric current for turning on the LED 11 flows.

Operations in the present embodiment are explained below.

Common to the first to fifth embodiments already explained, the LED driving section 23 according to the present embodiment adopts a circuit configuration for forming a constant current circuit. Therefore, in the case of an open circuit in which the optical adapter 4 is connected to the distal end portion 3, since a voltage source for leading in an electric current is not provided, the LED driving section 23 cannot be driven.

When the optical adapter 4 is connected to the distal end portion 3, the LED turn-on power supply 22 is connected and a closed circuit is formed through the LED 11 of the optical adapter 4. Therefore, the LED driving section 23 is driven and can drive the LED 11 with a constant current. When the optical adapter 4 is removed from the distal end portion 3, the optical adapter 4 enters a state in which an electric current does not flow to the LED 11 of the optical adapter 4 and the LED driving section 23 can also be brought into a state in which an electric current does not flow to the LED driving section 23.

According to the present embodiment, as in the first embodiment and the like, it is possible to realize a reduction in diameter of the insertion section 2, a reduction in diameter and a reduction in size of the optical adapter 4, and the like. With the simpler configuration, when the optical adapter 4 is connected to the distal end portion 3, the LED 11 can be automatically driven to be turned on. When the optical adapter 4 is not connected to the distal end portion 3, an electric current can be automatically prevented from flowing to the endoscope apparatus main body 5 side as well. In other words, it is possible to realize a reduction in size and the like of the endoscope apparatus. Moreover, it is possible to turn on or turn off the LED 11 with a reduced power according to attachment or detachment of the optical adapter 4 to or from the distal end portion 3.

In the present embodiment, the LED 11 can be automatically turned on or turned off with the reduced power according to attachment or detachment of the optical adapter 4 to and from the distal end portion 3 as described above. For attainment of the purposes descried above, the optical-adapter-attachment-and-detachment determining section 24 shown in FIG. 12 or FIG. 13 is unnecessary. However, in the present embodiment, a result of determination by the optical-adapter-attachment-and-detachment determining section 24 is used for the control of operations of the CCD driving section 27 and the control of operations of the image processing section 28 as explained in the first embodiment. Consequently, it is possible to realize, for example, a reduction in diameter of the insertion section 2 and the like of the endoscope apparatus and realize an endoscope apparatus further reduced in power.

Figure 14:
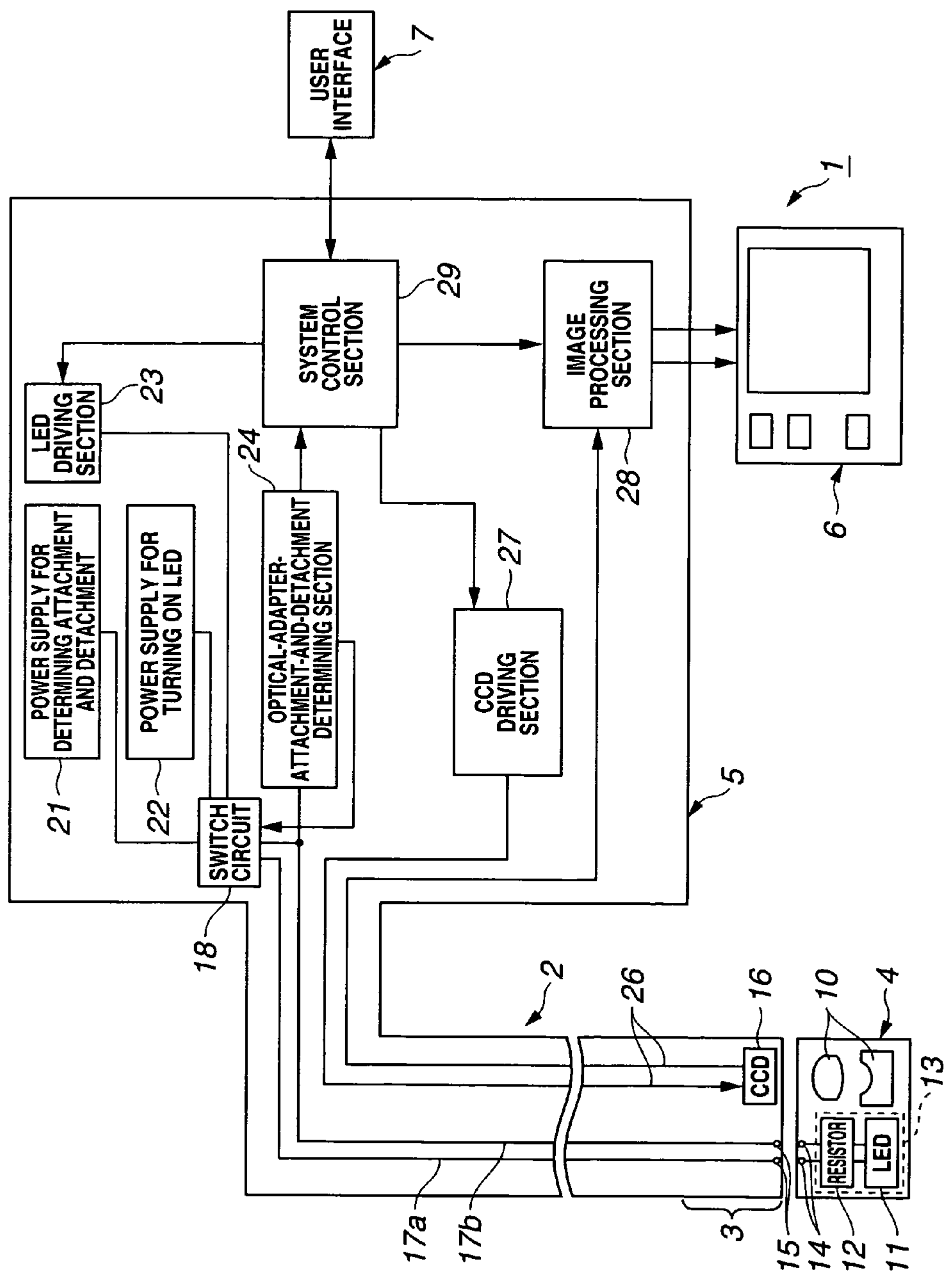
FIG. 14 is a block diagram showing an overall configuration of the endoscope apparatus according to the first embodiment of the present invention.

FIG. 14 is a block diagram of an overall configuration of the endoscope apparatus 1 according to the first embodiment. However, unlike FIG. 1, the optical-adapter-attachment-and-detachment determining section 24 is shown as a component different from the system control section 29. In the present invention, the optical-adapter-attachment-and-detachment determining section 24 is configured by the system control section 29. For ease of explanation of the operations, the explanation based on the configuration shown in FIG. 14 is also made as described above. It goes without saying that it is possible to realize the effect of the invention even if the optical-adapter-attachment-and-detachment determining section 24 is a component different from the system control section 29 as shown in FIG. 14.

<Seventh Embodiment>

Next, seventh to eleventh embodiments of the present invention are explained. Endoscope apparatuses according to the seventh to eleventh embodiments are similar to those according to the first to sixth embodiments but are different in that, for example, the endoscope apparatuses have respective optical-adapter-type determining sections.

Figure 15:
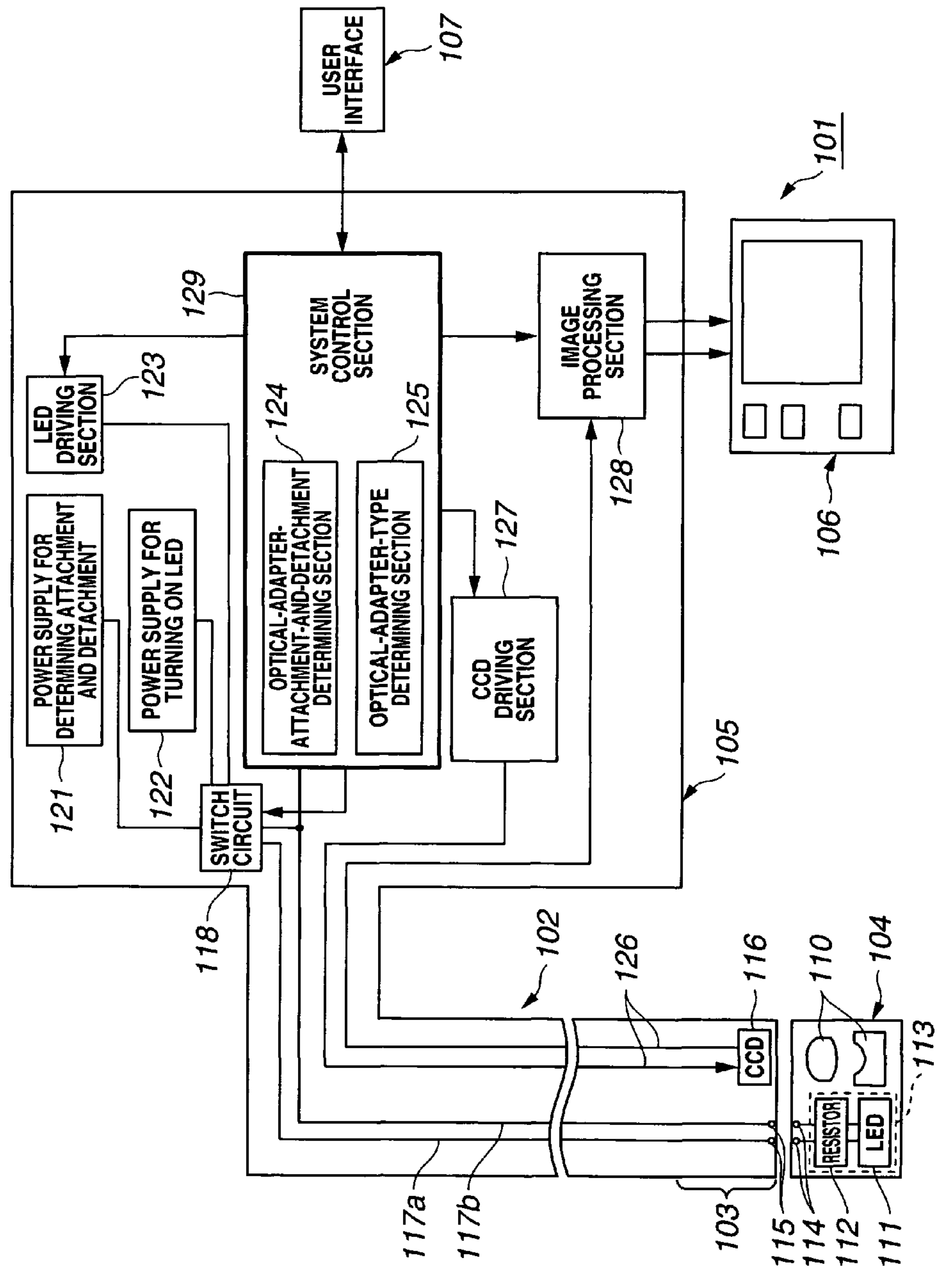
FIG. 15 is a block diagram showing an overall configuration of an endoscope apparatus according to a seventh embodiment of the present invention.
Figure 16:
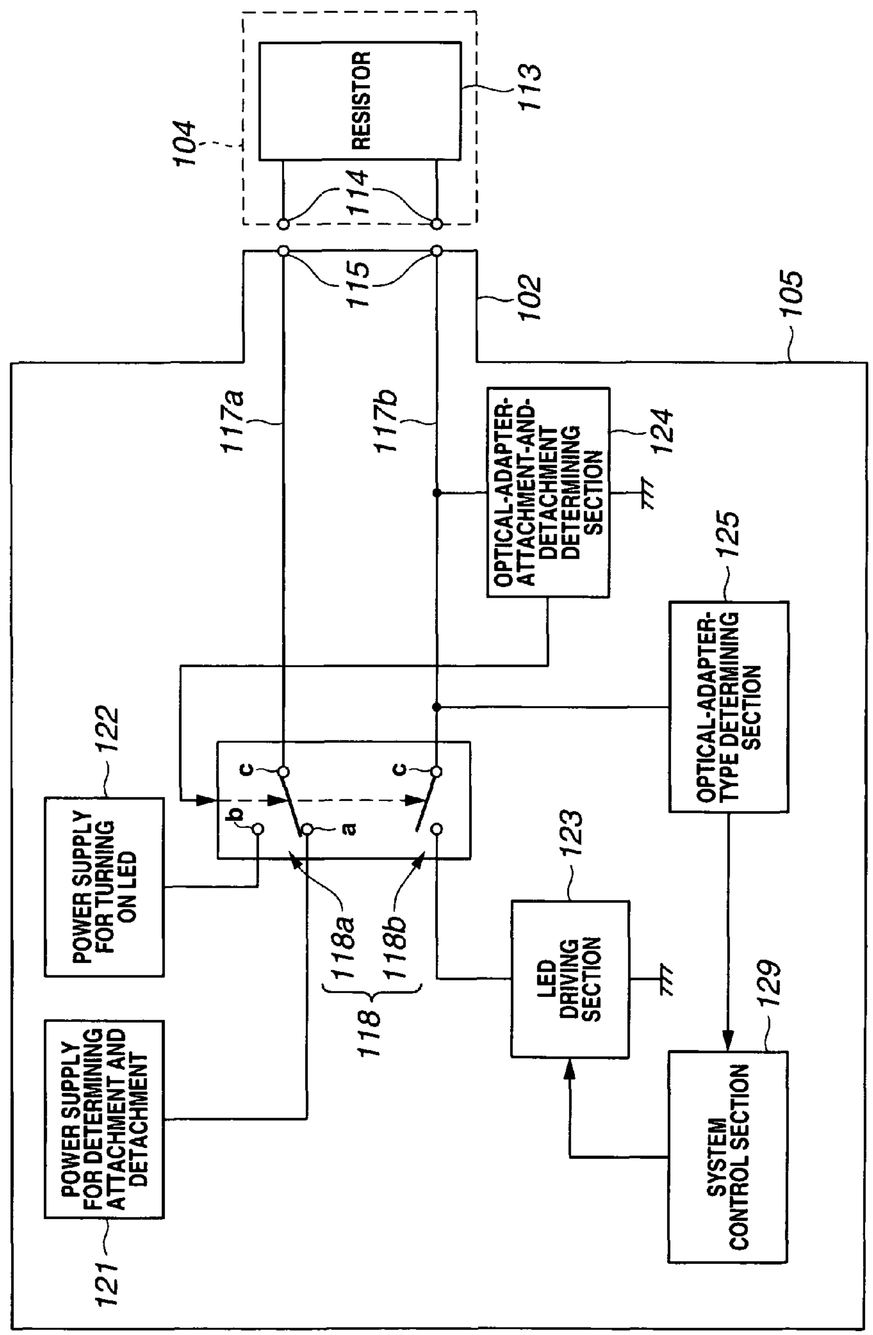
Figure 17:
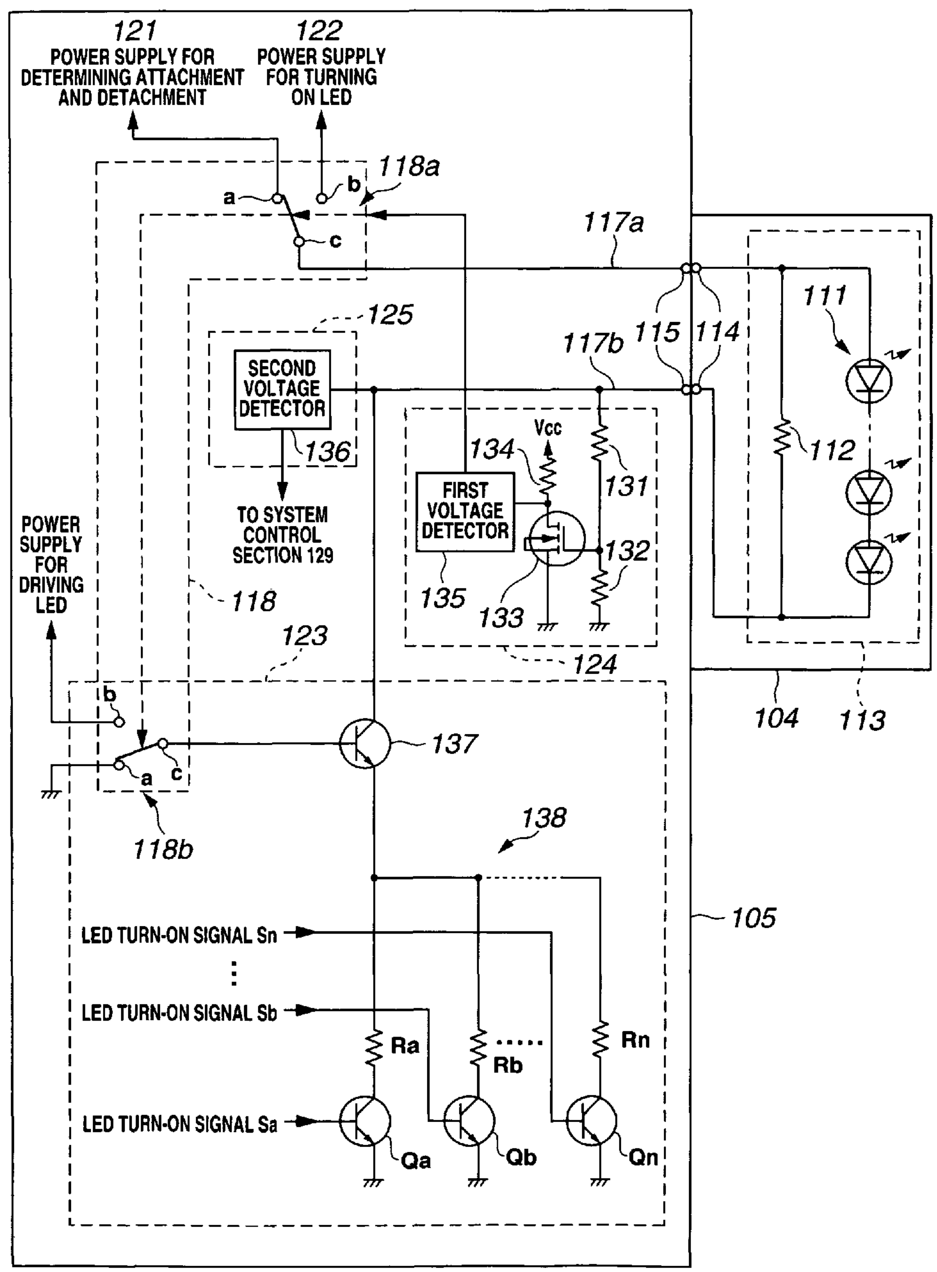
FIG. 17 is a circuit diagram showing a more specific circuit configuration of FIG. 16.
Figure 18:
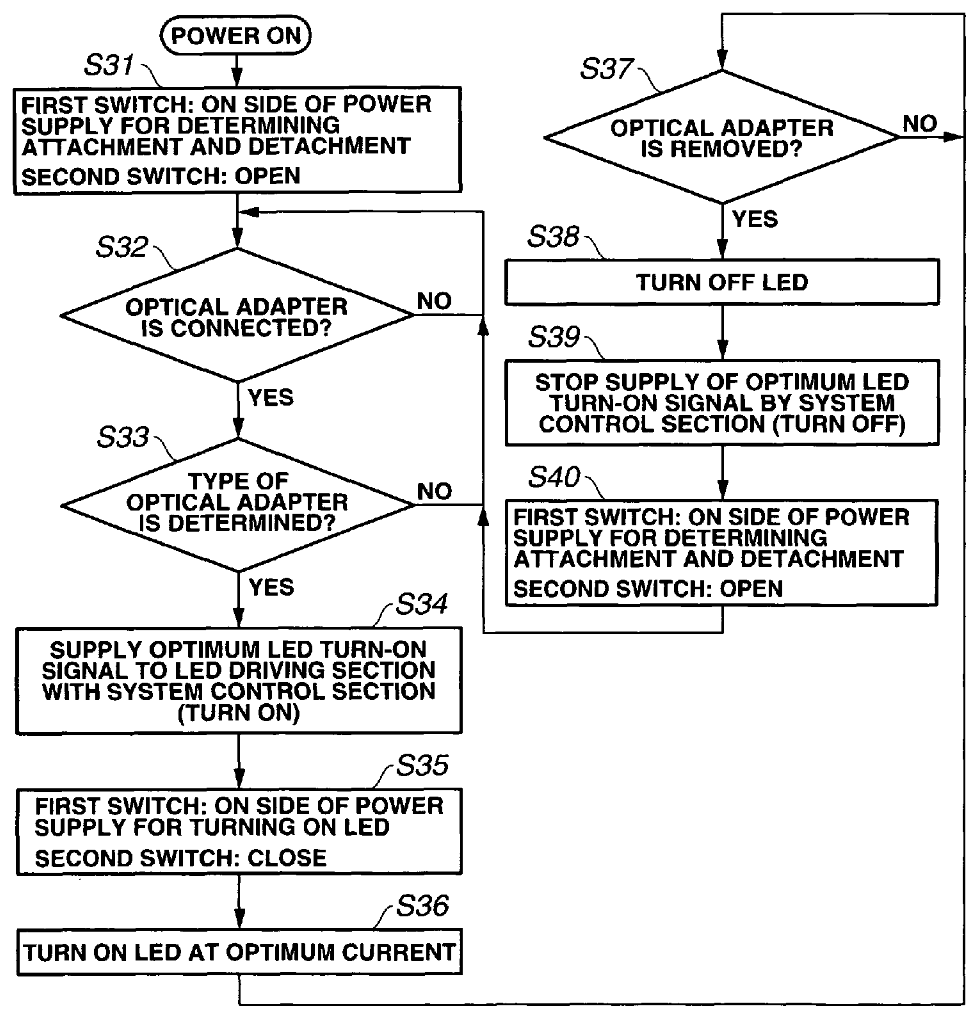
FIG. 18 is a flowchart showing operation contents according to the seventh embodiment of the present invention.

FIG. 15 to FIG. 18 relate to the ninth embodiment of the present invention. FIG. 15 shows an overall configuration of the endoscope apparatus according to the seventh embodiment of the present invention. FIG. 16 shows a configuration of a main part in the endoscope apparatus including an optical-adapter-attachment-and-detachment determining section and an optical-adapter-type determining section. FIG. 17 shows a more specific circuit configuration of FIG. 16 and FIG. 18 shows operation contents in the present embodiment.

In FIG. 16 and the like referred to below, for ease of explanation, an optical-adapter-attachment-and-detachment determining section 124 and an optical-adapter-type determining section 125 are shown as components different from a system control section 129.

As shown in FIG. 15, an industrial endoscope apparatus 101 according to a seventh embodiment of the present invention includes an endoscope insertion section (hereinafter abbreviated as "insertion section") 102 mounted to the inside of a pipe of a chemical plant, an optical adapter 104 detachably connected to a distal end portion 103 of the insertion section 102, an endoscope apparatus main body 105 to which a rear end of the insertion section 102 is coupled and which incorporates an image processing section and the like, a display device 106 which is connected to the endoscope apparatus main body 105 and displays an endoscopic image and the like, and a user interface 107 with which a user performs various kinds of instruction operations and the like.

A not-shown mounting section by a screw section is provided at the distal end portion 103 of the insertion section 102. The optical adapter 104 can be detachably connected to the distal end portion 103. In the optical adapter 104, object lenses 110 and a light emitting diode (hereinafter abbreviated as "LED") 111 as a luminous body serving as a lighting section arranged adjacent to the object lenses 110 are arranged. The LED 11 is connected to two electric contacts 14 for connection, which are adapter side electric contacts, together with a resistor 112. A resistor element 113 included in the LED 111 and the resistor 112.

On the other hand, at the distal end portion 103 to which the optical adapter 104 is detachably attachable, electric contacts 115, which are insertion section side electric contacts connected to the electric contacts 114, are arranged and, for example, a charge coupled device (abbreviated as "CCD") 116 is arranged as an image pickup device in a position opposed to the object lenses 110. An optical image is formed on an image pickup surface of the CCD 116 by the object lenses 110.

The electric contacts 115 are connected to a switching circuit 118 and the like, which are provided in the endoscope apparatus main body 105, through two signal lines 117*a* and 117*b* inserted through the insertion section 102. The signal line 117*a* is connected to, through the switching circuit 118, an attachment-and-detachment determining power supply 121 for electrically detecting attachment and detachment of the optical adapter 104 to and from the distal end portion 103 or an LED turn-on power supply 122, which is a luminous body turn-on power supply, for supplying a current for lighting to the LED 111.

The signal line 117*b* is connected to, through the switching circuit 118, an LED driving section 123 which drives the LED 111 and connected to an optical-adapter-attachment-and-detachment determining section 124 which electrically determines attachment and detachment of the optical adapter 104 to and from the distal end portion 103 and an optical-adapter-type determining section 125 which electrically performs type determination for the optical adapter 104.

In the endoscope apparatus main body 105, a system control section 129 which configures the optical-adapter-attachment-and-detachment determining section 124, the optical-adapter-type determining section 125, and the like and performs control of the respective sections in the endoscope apparatus main body 105 is provided.

The system control section 129 is inputted with a signal for type determination for the optical adapter 104 by the optical-adapter-type determining section 125 and controls the LED driving section 123 according to a result of the type determination. The LED driving section 123 sets a driving current (hereinafter simply referred to as "electric current") to the LED 111 to be an optimum value according to the control by the system control section 129.

The system control section 129 controls, according to a result of determination by the optical-adapter-attachment-and-detachment determining section 124 that the optical adapter 104 is connected to the distal end portion 103 of the insertion section 102, whether the CCD driving section 127 and the like should be actuated. Specifically, when the optical adapter 104 is connected to the distal end portion 103, the system control section 129 performs control for bringing the CCD driving section 127 and the like into an operation state. When the optical adapter 104 is not connected to the distal end portion 103, the system control section 129 controls the CCD driving section 127 and the like to a non-operation state, reduces wasteful power consumption of the endoscope apparatus, and realizes power saving.

Moreover, the system control section 129 performs, according to a result of determination by the optical-adapter-attachment-and-detachment determining section 124 that the optical adapter 104 is connected to the distal end portion 103 of the insertion section 102, control for switching of the switching circuit 118.

As described above, in the endoscope apparatus 101 according to the present embodiment, as signal lines disposed in the insertion section 102, there are only two signal lines, i.e., the signal lines 117*a* and 117*b* connected to the optical adapter 104 excluding the signal line 126 connected to the CCD 116. Therefore, it is possible to realize a reduction in diameter of the insertion section 102.

In the endoscope apparatus 101, a reduction in size and a reduction in diameter of the optical adapter 104 are realized by providing only the two electric contacts 114 in the optical adapter 104 as well. The number of signal lines in the optical adapter 104 is reduced to realize a reduction in size of the optical adapter 104 by providing only the two electric contacts 114.

FIG. 16 is a block diagram showing a configuration of an electric system of a main part which performs attachment and detachment determination and type determination for the optical adapter 104 in the present embodiment.

The electric contacts 115 on the insertion section 102 side connected to the two electric contacts 114 of the optical adapter 104 are connected to a contact "c" of a first switch 118*a* and a contact "c" of a second switch 118*b* in the switching circuit 118 by the two signal lines 117*a* and 117*b*, respectively. FIG. 17 shows a detailed circuit configuration of the main part in FIG. 16.

The contact "c" of the first switch 118*a* is selectively brought into a closed state with, i.e., connected to any one of a contact "a" connected to the attachment-and-detachment determining power supply 121 and a contact "b" connected to the LED turn-on power supply 122.

On the other hand, the second switch 118*b* in FIG. 12 performs processing for switching a (open) state in which an electric current flows to the LED driving section 123 and a (closed) state in which an electric current flows to the LED driving section 123. As explained with reference to FIG. 15, the optical-adapter-attachment-and-detachment determining section 124 which determines attachment and detachment of the optical adapter 104 to and from the distal end portion 103 and the optical-adapter-type determining section 125 which performs type determination for the optical adapter 104 are connected to the signal line 117*b*.

In a state of the switching circuit 118 shown in FIG. 16 or a state of the switching circuit 118 shown in FIG. 17, the optical-adapter-attachment-and-detachment determining section 124 electrically determines attachment and detachment of the optical adapter 104 to and from the distal end portion 103 using the attachment-and-detachment determining power supply 121. When the optical adapter 104 is connected to the distal end portion 103, the system control section 129 performs switching control for the switching circuit 118.

In the optical adapter 104, the LED 111 in which plural LED elements are connected in series and the resistor 112 for type determination for the optical adapter 104 are connected in parallel between the two electric contacts 114. A resistance of the resistor 112 is set to different values according to types of the optical adapter 104. For example, a resistance of the resistor 112 is set according to the number of LED elements of the LED 111 mounted on the optical adapter 104, a light emission characteristic of the LED 111, and the like. The system control section 129 controls a current value flowing to the LED driving section 123 according to a type of the optical adapter determined by the optical-adapter-type determining section 125 to thereby turn on the LED 111 of the optical adapter 104, which is connected to the distal end portion 103, in an optimum state.

In the present embodiment, as described above, when there are the plural LED elements provided in the optical adapter 104, the resistor 112 for type determination is connected in parallel to the LED 111 in which the LED elements are connected in series to reduce the number of contacts provided in the optical adapter 104 to two and make it possible to reduce a size of the optical adapter 104. Although there are only two contacts, type determination for the optical adapter 104 can be performed in addition to determination on attachment and detachment of the optical adapter 104 to and from the distal end portion 103.

On the other hand, the signal line 117*a* connected to the electric contact 115 is connected to the contact “c” of the first switch 118*a* of the switching circuit 118. The contact “a” of the first switch 118*a* is connected to the attachment-and-detachment determining power supply 21. The contact “b” of the first switch 118*a* is connected to the LED turn-on power supply 122.

In an initial state, the contact “c” of the first switch 118*a* is set to be connected to the contact “a” as shown in FIG. 17. When the electric contacts 115 and 114 are connected as shown in FIG. 17, an electric current is supplied from the attachment-and-detachment determining power supply 121 to the optical-adapter-attachment-and-detachment determining section 124 and optical-adapter-type determining section 125 side through the resistor 112 of the optical adapter 104.

The signal line 117*b* connected to the electric contact 115 is connected to one end of a resistor 131 included in the optical-adapter-attachment-and-detachment determining section 124. The other end of the resistor 131 is connected to the GND through a resistor 132 and connected to, for example, a gate terminal of an FET 133 of an N-channel type. A drain terminal of the FET 133 is connected to a power supply terminal Vcc through a resistor 134 and connected to a voltage detection terminal of a first voltage detection circuit 135. A source terminal of the FET 133 is connected to the GND.

As shown in FIG. 17, when the electric contacts 114 and 115 are connected, a voltage at a contact point of the resistors 131 and 132 is applied to the gate terminal of the FET 133, whereby the FET 133 is turned on from OFF to ON. The first voltage detection circuit 135 changes from a state of the power supply terminal Vcc larger than 0 V to a state for detecting a voltage 0 V. The optical-adapter-attachment-and-detachment determining section 124 determines that the optical adapter 104 is connected to the distal end portion 103. The first voltage detection circuit 135 controls switching of the switching circuit 118 from an output end thereof via the system control section 129 according to a determination result signal of the optical-adapter-attachment-and-detachment determining section 124.

The signal line 117*b* is inputted to a second voltage detection circuit 136 included in the optical-adapter-type determining section 125. The second voltage detection circuit 136 detects a voltage of the signal line 117*b* to thereby determine a type of the optical adapter 104. The optical-adapter-type determining section 125 outputs a type determination signal to the system control section 129. The system control section 129 controls a driving current by the LED driving section 123 to cause the LED 111 to appropriately emit light depending on a type of the optical adapter 104 connected thereto.

In the present embodiment and the like, it is explained that a control signal for type determination by the optical-adapter-type determining section 125 is sent to the system control section 129 and the system control section 129 controls a driving current by the LED driving section 123 to appropriately turn on the LED 111. However, a driving current by the LED driving section 123 may be controlled according to a control signal for type determination by the optical-adapter-type determining section 125.

The signal line 117*b* is connected to a collector terminal of a transistor 137 included in the LED driving section 123. A base terminal of the transistor 137 is connected to the contact “c” of the second switch 118*b*. The contact “a” of the second switch 118*b* is connected to the GND and the contact “b” thereof is connected to the LED driving power supply. In the initial state, as shown in FIG. 17, the contact “c” of the first switch 118*a* is set to be connected to the contact “a” and the transistor 137 is set in an OFF state.

An emitter terminal of the transistor 137 is connected to plural resistors Ra, Rb, . . . , and Rn included in an LED-driving-current setting section 138. These resistors Ra, Rb, . . . , and Rn are connected to collector terminals of transistors Qa, Qb, . . . , Qn having a function of a switching circuit, respectively. Emitter terminals of the transistors Qa, Qb, . . . , and Qn are connected to the GND. LED turn-on signals Sa, Sb, . . . , and Sn are supplied to base terminals of the transistors Qa, Qb, . . . , Qn from the system control section 129. Resistances of these resistors Ra, Rb, . . . , and Rn (in the following explanation, for simplification, signs same as those of the resistors are used for the resistances) are set in a relation Ra>Rb> . . . >Rn. An electric current flowing between the collector terminal and the emitter terminal of the transistor 137 can be set by selectively setting an LED turn-on signal to be actually applied among these LED turn-on signals Sa, Sb, . . . , Sn.

Operations in the present embodiment with such a configuration are explained.

When an electric power is supplied to the endoscope apparatus main body 105, as shown in FIG. 16 or FIG. 17, according to an output signal of the first detection circuit 135 included in the optical-adapter-attachment-and-detachment determining section 124, a connection state at the initial time of the switching circuit 118 is a state in which the respective contacts “c” are connected to the respective contacts “a”. The connection state of the switching circuit 118 is a case in which a voltage at an input terminal of the first voltage detection circuit 135 is the power supply terminal Vcc. As explained below, when the voltage at the input terminal changes to 0V, the system control section 129 performs control for switching the contacts of the switching circuit 118 according to an output signal of the first voltage detection circuit 135.

When the optical adapter 104 is connected to the distal end portion 103, a closed circuit (hereinafter referred to as “closed circuit A2”) which is a current path of “the attachment-and-detachment determining power supply 121→the first switch 118*a* of the switching circuit 118→the resistor 112 of the resistor element 113 of the optical adapter 104→a resistor 131 to the resistor 132 of the optical-adapter-attachment-and-detachment determining section 124” is formed. The optical-adapter-attachment-and-detachment determining section 124 determines that the optical adapter 104 is connected to the distal end portion 103.

If a voltage of the attachment-and-detachment determining power supply 121 is set to be equal to or lower than Vf (a forward drop voltage) of the LED 111 of the optical adapter 104, the closed circuit A2 is formed. For example, in the case of a white LED, since an LED with a Vf of about 3.5V is used as the LED 111, it is preferable to set a voltage of the attachment-and-detachment determining power supply 121 to a voltage smaller than the Vf, for example, a constant voltage of about 2 to 3V.

When a voltage applied to the resistor 132 is applied to a gate terminal of the FET 114 of the optical-adapter-attachment-and-detachment determining section 124, the FET 114 is turned on. When the FET 14 is turned on, the first voltage detection circuit 135 detects the voltage of 0V (GND) and outputs a connection determination signal. According to the connection determination signal, the switching circuit 118 is switched by the system control section 129 to be connected to a contact side different from that in the connection state shown in FIG. 16 or FIG. 17.

In the present embodiment, the system control section 129 controls contact switching for the switching circuit 118. However, an output signal of the optical-adapter-attachment-and-detachment determining section 124 may directly perform contact switching for the switching circuit 118.

When the switching circuit 118 is switched to the contact side different from that in the connection state at the initial time, a closed circuit of "the LED turn-on power supply 122→the switching circuit 118→the LED 111 of the optical adapter 104→the transistor 137 of the LED driving section 123→any one of the resistors Ra to Rn" is formed. The LED 111 of the optical adapter 104 is turned on.

Moreover, a closed circuit (hereinafter referred to as "closed circuit B2") of "the LED turn-on power supply 122→the switching circuit 118→the LED 111 of the optical adapter 104→the resistor 131 to the resistor 132 of the optical-adapter-attachment-and-detachment determining section 124" is also formed. The optical-adapter-attachment-and-detachment determining section 124 continues to determine that the optical adapter 104 is connected and maintains a switch of the switching circuit 118 in a state in which the contact "b" side is connected different from the contact state at the initial time. In the state, the system control section 129 performs control not to read a control signal of a type determination result from the optical-adapter-type determining section 125. Power consumption of the LED turn-on power supply 122 is large compared with the attachment-and-detachment determining power supply 121.

A resistance of the resistor 112 of the optical adapter 104 is set to, for example, a value larger than (e.g., several hundred kΩ) 1000 times compared with a resistance (specifically, equal to or lower than about 100Ω) between the anode and the cathode of the LED 111 at the time of the LED 111 lighting (equal to or higher than Vf). Therefore, an electric current flowing to the resistor 112 at the time of the LED 111 lighting can be neglected because the electric current is very small compared with an electric current flowing to the LED 111. Therefore, since the resistor 112 can be considered opened, the closed circuit B2 is formed.

The second switch 118*b* on a lower side of the switching circuit 118 shown in FIG. 16 is configured by a switch inserted between the base terminal of the transistor 137 and the LED driving power supply or the GND in FIG. 17.

When the optical-adapter-attachment-and-detachment determining section 124 determines that the optical adapter 104 is connected to the distal end portion 103 and the second switch 118*b* is brought into a connection state on the LED driving power supply side by the first voltage detection circuit 135 of the optical-adapter-attachment-and-detachment determining section 124, the LED driving power supply is supplied to the base terminal of the transistor 137, the transistor 137 is turned on, and the collector terminal and the emitter terminal of the transistor 137 become conductive.

On the other hand, when the optical adapter 104 is removed from the distal end portion 103, the second switch 118*b* is connected to the GND. In other word, the collector terminal and the emitter terminal of the transistor 137 come into an open state while the transistor 137 remains turned off. In other words, the transistor 137 performs an operation of a switching circuit and can be represented like the second switch 118*b* of the switching circuit 118 shown in FIG. 16.

When the optical adapter 104 is connected to the distal end portion 103 and then removed from the distal end portion 103 in a state in which the LED 111 is on, a voltage is not applied to the gate terminal of the FET 133 of the optical-adapter-attachment-and-detachment determining section 124 and the FET 133 is turned off. When the FET 133 is turned off, a voltage at the power supply terminal Vcc is applied to the input terminal for voltage detection of the first voltage detection circuit 135 through the resistor for pull-up 134. When the voltage at the power supply terminal Vcc is applied to the input terminal of the first voltage detection circuit 135, the first voltage detection circuit 135 determines, according to a voltage detection by the first voltage detection circuit 135, that the optical adapter 104 and the distal end portion 103 are not connected. According to an output signal of the first voltage detection circuit 135, the system control section 129 performs contact switching such that the first switch 118*a* and the second switch 118*b* of the switching circuit 118 are connected on the contact side shown in FIG. 16 or FIG. 17. Consequently, the LED turn-on power supply 122, which consumes more power than the attachment-and-detachment determining power supply 121, is not connected to the electric contacts 115.

A constant current circuit is configured by a combination of the resistors Ra to Rn in the LED driving section 123 and the transistor 137. In other words, when the optical adapter 104 is connected and the LED 111 is turned on, a voltage of Va=VB−VBE is applied to the resistors Ra to Rn. VB represents a voltage at the base terminal of the transistor 137, i.e., a voltage of the LED driving power supply, and VBE represents a voltage between the base terminal and the emitter terminal of the transistor 137. In other words, an electric current In indicated by In =Va/(resistances Ra to Rn of the resistors Ra to Rn) flows to the resistors Ra to Rn. The electric current In flows to the LED 111 as well because the transistor 137 is turned on. The LED driving section 123 configures a constant current circuit for driving the LED 111 with the electric current In. A current value of the constant current circuit In can be set by setting values of the resistances Ra to Rn of the resistors Ra to Rn.

When the optical adapter 104 is removed from the distal end portion 103, the optical-adapter-attachment-and-detachment determining section 124 determines that the optical adapter 104 is removed from the distal end portion 103. The system control section 129 switches the first switch 118*a* of the switching circuit 118 to the attachment-and-detachment determining power supply 121 side and switches the second switch 118*b* thereof to the open state. Moreover, when the optical adapter 104 is removed from the distal end portion 103, a voltage is not applied to the optical-adapter-type determining section 125 either. Therefore, the system control section 129 turns off LED turn-on signals Sa to Sn of the LED driving section 123.

Next, a flow of processing according to the present embodiment is explained with reference to a flowchart of FIG. 18.

When electric power is supplied to the endoscope apparatus main body 5, the switching circuit 18 is set in the connection state at the initial time according to an output signal of the first voltage detection circuit 135 included in the optical-adapter-attachment-and-detachment determining section 124. In other words, as shown in step S31, the first switch 118*a* is connected on the attachment-and-detachment determining power supply 121 side, and the second switch is in the open state (see FIG. 16) in which an electric current does not flow to the LED driving section 123.

In step S32, the optical-adapter-attachment-and-detachment determining section 124 enters a waiting state for the optical adapter 104 to be connected to the distal end portion 103.

When the optical adapter 104 is connected to the distal end portion 103, a closed circuit A2 of "the attachment-and-detachment determining power supply 121 the first switch 118*a* of the switching circuit 118→the resistor 112 of the resistor element 113 of the optical adapter 104→the resistor 131→the resistor 132 of the optical-adapter-attachment-and-detachment determining section 124" is formed. The optical-adapter-attachment-and-detachment determining section 124 determines that the optical adapter 104 is connected to the distal end portion 103.

A voltage of the attachment-and-detachment determining power supply 121 is set to be equal to or lower than Vf (the forward drop voltage) of the LED 111 of the optical adapter 104 and the closed circuit A2 is formed. Therefore, a voltage applied to the resistor 132 is applied to the gate terminal of the FET 133 of the optical-adapter-attachment-and-detachment determining section 124 and the FET 133 is turned on.

When the FET 133 is turned on, a voltage at the input terminal of the first voltage detection circuit 135 changes to 0V (GND). The first voltage detection circuit 135 detects the voltage 0V and outputs a connection determination signal from the output terminal thereof.

Simultaneously with the processing in step S32, as shown in step S33, the optical-adapter-type determining section 125 performs determination of a type of the optical adapter 104. As shown in FIG. 16 or FIG. 17, a closed circuit of "the attachment-and-detachment determining power supply 121→the first switch 118*a* of the switching circuit 118→the resistor 112 of the resistor element 113 of the optical adapter 104→the optical-adapter-type determining section 125" is formed. The second voltage detection circuit 136 included in the optical-adapter-type determining section 125 performs type determination for determining, from a voltage value of the signal line 117*b*, the optical adapter 104 of which type is connected. The optical-adapter-type determining section 125 outputs a signal of type determination to the system control section 129. When the optical-adapter-type determining section 125 cannot determine a type of the optical adapter 104, the processing in step S32 is performed.

In step S34, the system control section 129 having received the signal of type determination supplies an optimum LED turn-on signal S1 (i=a to n) adapted to the type of the optical adapter 104, for example, the number of LED elements, side vision, direct vision, stereo direct vision, and stereo side vision to the LED driving section 123. A transistor Qi to which the optimum LED turn-on signal Si is supplied enters a state in which the transistor Qi can be turned on. However, in the state, since the second switch 118*b* is in the open state for making the transistor 137 nonconductive, the transistor Qi is actually turned on after processing in the next step S35.

In step S35, in the switching circuit 118, the first switch 118*a* is switched to the LED turn-on power supply 122 side and the second switch 118*b* is switched to the close state by the control by the system control section 129 on the basis of the connection determination signal outputted from the first voltage detection circuit 135 of the optical-adapter-attachment-and-detachment determining section 124.

In other words, the first switch 118*a* and the second switch 118*b* of the switching circuit 118 performs contact switching such that the contact "b" side different from the state at the initial time is connected. Then, the transistor 137 is turned on and a path through which an electric current by the LED turn-on power supply 122 flows to the LED driving section 123 side is formed through the collector terminal and the emitter terminal of the transistor 137. The transistor Qi to which the optimum LED turn-on signal Si is supplied is also turned on. As shown in step S36, the LED 111 is turned on with an optimum electric current.

After the LED 111 is turned on with the optimum electric current in the way, as shown in step S37, the optical-adapter-attachment-and-detachment determining section 124 always performs determination on whether the optical adapter 104 is not removed from the distal end portion 103.

When the optical adapter 104 is removed from the distal end portion 103, as shown in step S38, the LED 111 is turned off. The optical-adapter-attachment-and-detachment determining section 124 outputs a signal indicating that the optical adapter 104 is removed from the distal end portion 103, to the system control section 129.

Then, as shown in step S39, the system control section 129 stops supplying the optimum LED turn-on signal Si to the LED driving section 123, i.e., turns off the LED driving section 123.

In step S40, the system control section 129 switches the first switch 118*a* of the switching circuit 118 to the attachment-and-detachment determining power supply 121 side and switches the first switch 118*b* thereof to the open state. In other words, the system control section 129 switches the switching circuit 118 to the state at the initial time. The processing by the system control section 129 returns to step S32 and the processing is repeated.

According to the present embodiment in which the operations are performed as described above, the number of electric contacts of the optical adapter 104 mounted with the resistor element 113 including the LED 111 as a luminous body can be reduced to two, and the number of signal lines can also be reduced to two. Therefore, it is possible to realize a reduction in size and a reduction in diameter of the optical adapter 104.

The number of contacts necessary for the distal end portion 103 to which the optical adapter 104 is detachably attachable is also two and the number of signal lines connected to the contacts is also two. Therefore, the endoscope apparatus according to the present embodiment can realize a reduction in diameter of the insertion section 102 and realize a reduction in diameter, and a reduction in size of the distal end portion.

At the time of attachment and detachment determination for the optical adapter 104, attachment and detachment determination is performed on the basis of a voltage supplied through the resistor 112 provided on the optical adapter 104 side by using the low-power consumption attachment-and-detachment determining power supply 121 and, when the optical adapter 104 is connected to the distal end portion 103, the attachment-and-detachment determining power supply 121 is switched to the LED turn-on power supply 122 for turning on the LED 111 by the switching circuit 118 in the endoscope apparatus main body 105. Consequently, the endoscope apparatus according to the present embodiment realizes power saving and the like as well as a reduction in the number of signal lines.

In other words, since the endoscope apparatus according to the present embodiment has the attachment-and-detachment determining power supply 121 exclusively used for attachment and detachment determination and the LED turn-on power supply 122 exclusively used for LED lighting, a circuit configuration is simple and can be easily controlled. Moreover, by using the attachment-and-detachment determining power supply 121 which consumes less power than the LED turn-on power supply 122, it is possible to reduce power consumption when the optical adapter 104 is not connected to the distal end portion 103.

The endoscope apparatus according to the present embodiment can perform type determination for the optical adapter 104 by changing, according to a type of the optical adapter 104, a resistance of the resistor 112 connected between the electric contacts of the optical adapter 104. In the endoscope apparatus according to the present embodiment, the system control section 129 has the optical-adapter-type determining section 125 which performs type determination of the optical adapter 104 using the attachment-and-detachment determining power supply 121. The system control section 129 performs control of a current value of the LED turn-on power supply 122, which is a luminous body turn-on power supply, on the basis of the determination of the optical-adapter-type determining section 125.

In particular, by setting a voltage of the attachment-and-detachment determining power supply 121 to a value lower than Vf (the forward drop voltage) of the LED 111, it is possible to accurately perform type determination without being affected by, for example, a characteristic of the LED 111 connected in parallel to the resistor 112 for type determination. In other word, the endoscope apparatus according to the present embodiment can perform type determination for a larger number of optical adapters 104 by changing a resistance of the resistor 112 of the optical adapter 104 for each type of the optical adapter 104.

When a resistance of the resistor 112 of the optical adapter 104 is changed for each type of the optical adapter 104, besides the number of LED elements mounted on the optical adapter 104, it is possible to set a type such as a direct vision type or a side vision type of the object lenses 10 to make it possible to identify the type. A resistance of the resistor 112 may be set according to an optical characteristic and the like of the object lens 10 to allow the optical-adapter-type determining section 125 to determine a type of the optical adapter 104. According to a result of type determination of the optical-adapter-type determining section 125, it is also possible to change image processing by the image processing section 128 according to an optical characteristic and the like of the object lenses 10.

The first voltage detection circuit 135 of the optical-adapter-attachment-and-detachment determining section 124 can be configured by a comparator, an FET, or the like but can also be configured by an integrated circuit such as a CPU. The switching circuit 118 can be configured by a relay, a photo-coupler, a photo-MOS relay, an FET, a transistor, or the like.

<Eighth Embodiment>

Figure 19:
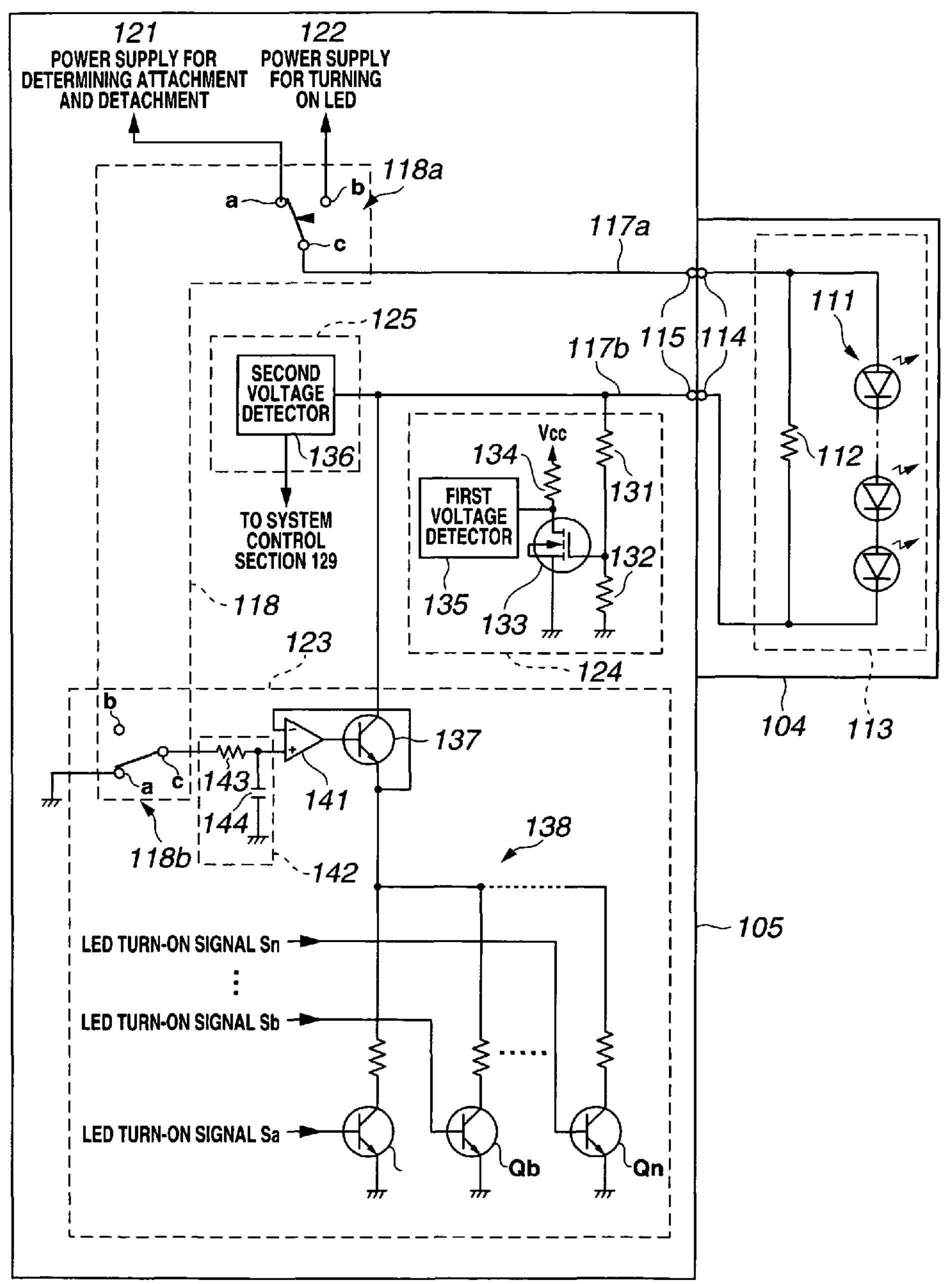
FIG. 19 is a circuit diagram showing a circuit configuration of a main part in an endoscope apparatus according to an eighth embodiment of the present invention.

An eighth embodiment of the present invention is explained with reference to FIG. 19. FIG. 19 shows a circuit configuration of a main part in an endoscope apparatus according to the eighth embodiment. The configuration in the eighth embodiment shown in FIG. 19 is configured by adding an operational amplifier 141 and an integrating circuit 142 to the LED driving section 123 according to the fifth embodiment shown in FIG. 17.

The endoscope apparatus according to the present embodiment added with the operational amplifier 141 can compensate for a change in VBE due to temperature fluctuation of the transistor 137 when the transistor 137 is turned on and the LED 111 is on. Therefore, it is possible to configure a more highly accurate constant current circuit.

The integrating circuit 142 of the endoscope apparatus according to the present embodiment is configured by a resistor 143 and a capacitor 144 and can delay a voltage applied to the base of the transistor 137. Therefore, the endoscope apparatus according to the present embodiment can gradually increase an electric current flowing to the LED 111, i.e., gradually increase a light amount of the LED. Since components of the endoscope apparatus according to the present embodiment other than the above are the same as those of the endoscope apparatus according to the seventh embodiment, explanation of the components is omitted.

With the endoscope apparatus according to the present embodiment, besides the actions and effects in the seventh embodiment, it is possible to more highly accurately turn on the LED 111 with an optimum electric current. With the endoscope apparatus according to the present embodiment, it is possible to prevent, using a delay section formed by the integrating circuit 142, an undesirable transient electric current from flowing when the LED 111 is turned on or turned off.

<Ninth Embodiment>

Figure 20:
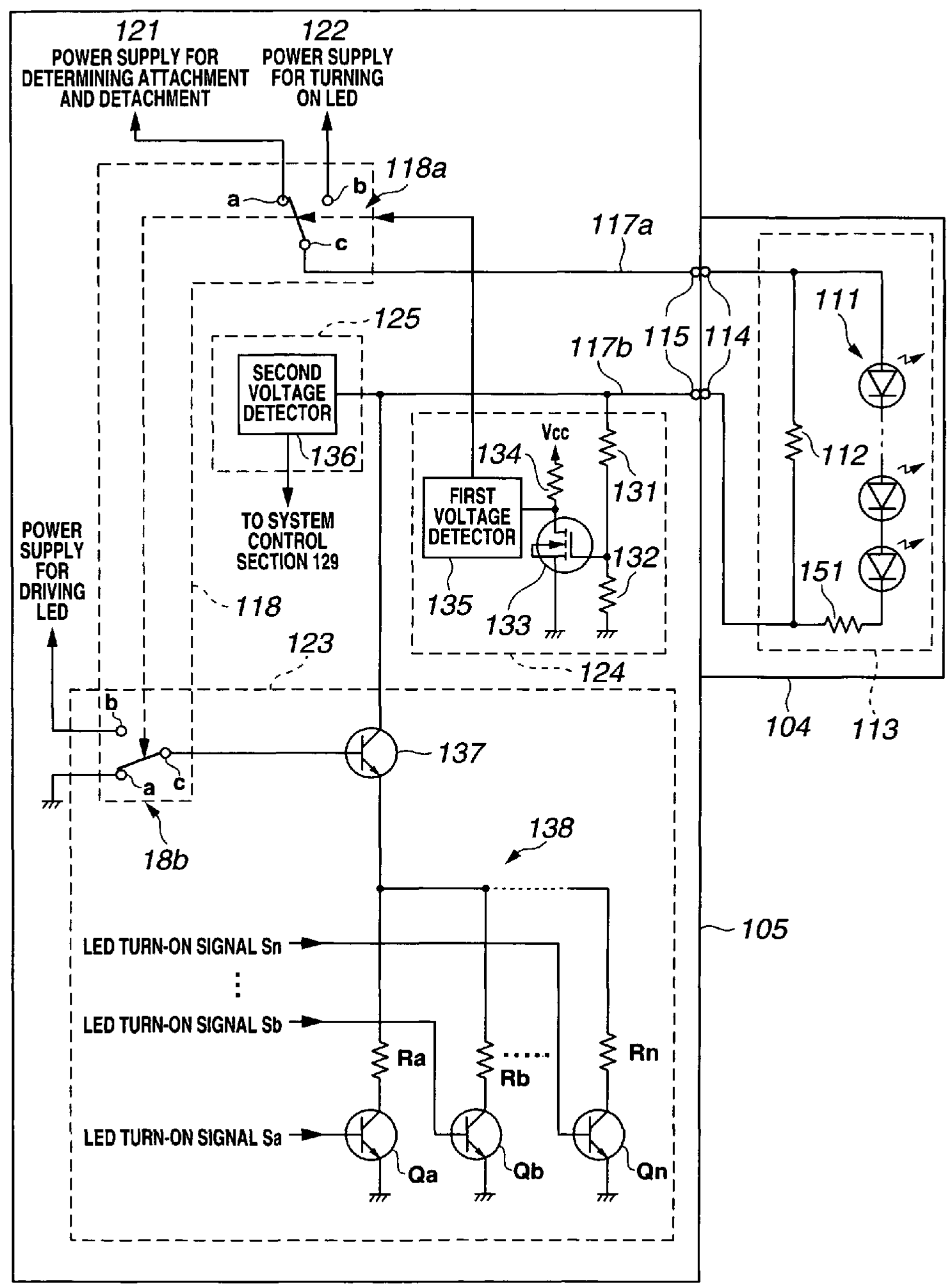
FIG. 20 is a circuit diagram showing a circuit configuration of a main part in an endoscope apparatus according to a ninth embodiment of the present invention.

Next, a ninth embodiment of the present invention is explained with reference to FIG. 20. FIG. 20 shows a configuration of a main part in an endoscope apparatus according to the ninth embodiment. A configuration of the endoscope apparatus according to the ninth embodiment shown in FIG. 20 is configured by adding a resistor 151 to the resistor element 113 of the optical adapter 104 in the configuration of the endoscope apparatus according to the seventh embodiment shown in FIG. 17.

In the endoscope apparatus according to the present embodiment, the resistor 151 is used for type determination for the optical adapter 104 and the resistor 121 is used for attachment and detachment determination. Therefore, a resistance of the resistor 151 is set to a different value for each optical adapter 104. Since other components of the endoscope apparatus according to the present embodiment are the same as those of the endoscope apparatus according to the seventh embodiment, explanation of the components is omitted.

In the endoscope apparatus according to the present embodiment, when connection of the optical adapter 104 to the distal end portion 103 is detected by the optical-adapter-attachment-and-detachment determining section 124, the switching circuit 118 is switched to a connection state shown in FIG. 20 to the other connection state.

In the case, first, the system control section 129 turns on the transistor Qa with the LED turn-on signal Sa with a lowest current amount. When the LED 111 is turned on, the optical-adapter-type determining section 125 detects a voltage addition generated by the resistor 151. The system control section 129 subjects the LED 111 to constant current control with the LED turn-on signal Si optimum for the respective optical adapters 104. Since the resistor 112 is used for only attachment and detachment determination, a resistance of the resistor 112 may be the same value even if types of the optical adapters 104 are different. However, the resistance of the resistor 112 is set to be sufficiently large, for example, to a resistance 1000 times or more as large as a resistance between the anode terminal and the cathode terminal at the time when the LED 111 is turned on with a voltage equal to or higher than Vf With the configuration according to the present embodiment, it is also possible to realize a reduction in size and the like of the optical adapter 104 as in the fifth embodiment.

<Tenth Embodiment>

Figure 21:
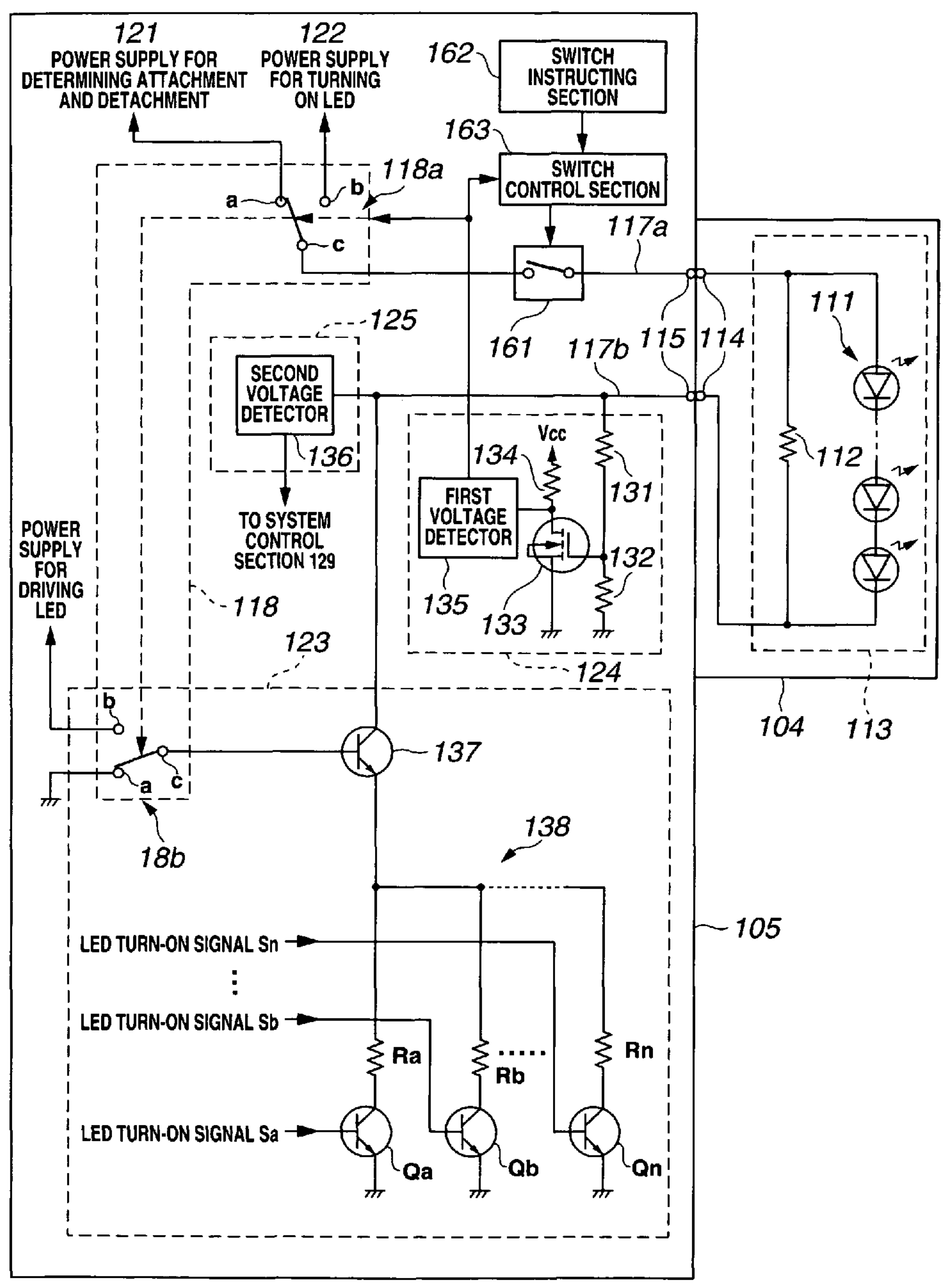
FIG. 21 is a circuit diagram showing a circuit configuration of a main part in an endoscope apparatus according to a tenth embodiment of the present invention.
Figure 22:
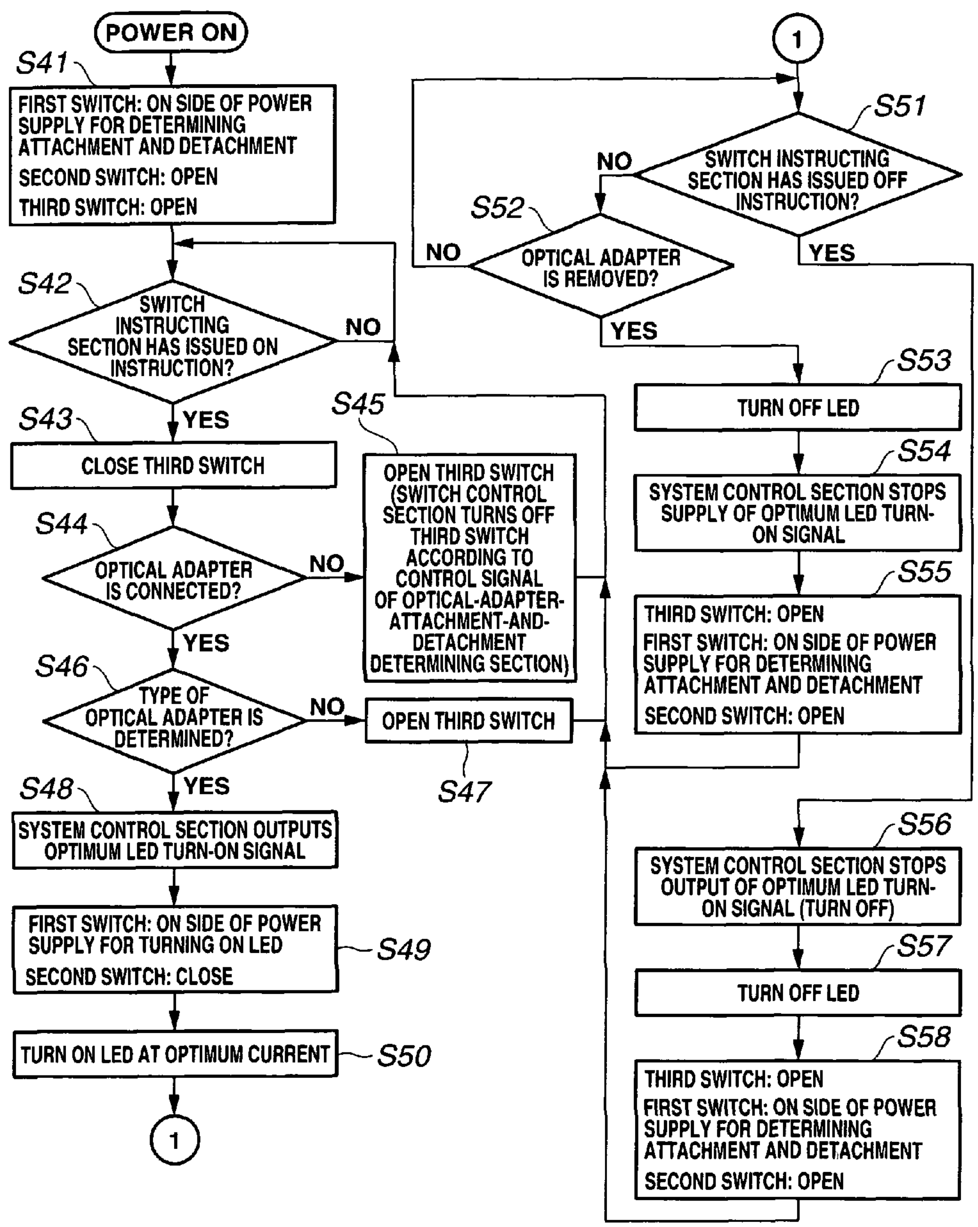
FIG. 22 is a flowchart showing operation contents according to the tenth embodiment of the present invention.

Next, a tenth embodiment of the present invention is explained with reference to FIG. 21 and FIG. 22. FIG. 21 shows a configuration of a main part in an endoscope apparatus according to the tenth embodiment. A configuration of the endoscope apparatus according to the present embodiment shown in FIG. 21 is configured by adding, in the configuration of the endoscope apparatus according to the seventh embodiment, a third switch 161 provided in the signal line 117*a*, a switch instructing section 162 which performs ON/OFF instruction for the third switch 161, and a switch control section 163 which performs ON/OFF control for the third switch 161 according to an instruction of the switch instructing section 162.

In the endoscope apparatus according to the present embodiment, the first voltage detection circuit 135 of the optical-adapter-attachment-and-detachment determining section 124 outputs a signal for controlling the switching circuit 118 as in the seventh embodiment and outputs a control signal for attachment and detachment determination to the switch control section 163 as well. The switch control section 163 controls ON/OFF (close/open) of the third switch 161 according to the control signal from the first voltage detection circuit 135. Other components in the endoscope apparatus according to the present embodiment are the same as those in the seventh embodiment. Only differences of the endoscope apparatus according to the present embodiment from the seventh embodiment are explained below.

In the endoscope apparatus according to the present embodiment, when a switch ON instruction is inputted to the switch control section 163 from the switch instructing section 162 such as a momentary switch (see FIG. 15) on the user interface 7 in a state in which the optical adapter 104 is not connected to the distal end portion 103, the switch control section 163 switches the third switch 161 to a connection state.

When the optical adapter 104 is not connected to the distal end portion 103, the optical-adapter-attachment-and-detachment determining section 124 does not send a signal to the switching circuit 118. Therefore, a connection state of the contacts of the switching circuit 118 is the same as that shown in FIG. 17 or FIG. 20, i.e., the contact "a" side is in a connection state. At the same time, the optical-adapter-attachment-and-detachment determining section 124 sends a control signal to the switch control section 163 and switches the third switch 161 to an open state.

In other words, in the endoscope apparatus according to the present embodiment, even in a state in which the optical adapter 104 is connected to the distal end portion 103, unless a user does not perform an ON operation instruction from the switch instructing section 162, a voltage is not applied to the electric contacts 114 of the optical adapter 104. When a switch ON instruction is inputted to the switch control section 163 from the switch instructing section 162 in a state in which the optical adapter 104 is connected to the distal end portion 103, the third switch 161 is switched to the connection state.

When the optical adapter 104 is removed from the distal end portion 103 in a state in which the LED 111 of the optical adapter 104 is on, the LED 111 of the optical adapter 104 is turned off. The optical-adapter-attachment-and-detachment determining section 124 determines that the optical adapter 104 is removed and outputs a signal to the switching circuit 118. Then, the first switch 118*a* of the switching circuit 118 is controlled to the attachment-and-detachment determining power supply 121 side and the second switch 118*b* thereof is controlled to the open state. At the same time, the optical-adapter-attachment-and-detachment determining section 124 outputs a signal to the switch control section 163 and the third switch 161 is switched to the open state.

The first voltage detection circuit 135 or the switch control section 163 can be configured by a comparator, an FET, an AD converter, or the like but can also be realized by an integrated circuit such as a CPU. The switching circuit 118 can be configured by a relay, a photo-coupler, a photo-MOS relay, an FET, a transistor, or the like.

It is also possible to change the configuration of the endoscope apparatus according to the present embodiment shown in FIG. 21 to a configuration added with the operational amplifier 141 and the integrating circuit 142 as in the configuration according to the eighth embodiment.

Next, a flow of processing in the present embodiment is explained with reference to a flowchart of FIG. 22.

When electric power is supplied to the endoscope apparatus, in step S41, the first switch 118*a* of the switching circuit 118 is switched to the attachment-and-detachment determining power supply side and the second switch 118*b* is switched to the open state. The third switch 161 is also in the open state.

In step S42, the switch control section 163 enters a standby waiting state for a third switch ON instruction to be outputted from the switch instructing section 162. When the third switch ON instruction is outputted from the switch instructing section 162, in step S43, the switch control section 163 switches the third switch 161 to a close state, which is an ON state. In the next step S44, the optical-adapter-attachment-and-detachment determining section 124 performs determination on whether the optical adapter 104 is connected to the distal end portion 103.

When the optical-adapter-attachment-and-detachment determining section 124 determines that the optical adapter 104 is not connected, as shown in step S45, the third switch 161 is switched to the open state. In other words, after the third switch 161 is switched to the open state via the switch control section 163 according to a signal of the optical-adapter-attachment-and-detachment determining section 124, processing in step S42 is started.

On the other hand, when the optical-adapter-attachment-and-detachment determining section 124 determines that the optical adapter 104 is connected to the distal end portion 103, processing in step S46 is performed and the optical-adapter-type determining section 125 performs processing for determining a type of the optical adapter 104. However, when the optical-adapter-type determining section 125 cannot determine a type of the optical adapter 104, in step S47, as in the case of the processing in step S45, after the third switch 161 is switched to the open state, the processing in step S42 is started.

When determination on a type of the optical adapter 104 is performed by the optical-adapter-type determining section 125, a signal of the type determination is sent to the system control section 129. In step S48, the system control section 129 having received the signal of the type determination supplies the LED turn-on signal Si of an optimum current value to the LED driving section 123.

In the next step S49, the system control section 129 switches the first switch 118*a* of the switching circuit 118 to the LED turn-on power supply 122 side and switches the second switch 118*b* thereof to the closed state according to a connection determination signal.

Consequently, as shown in step S50, an electric current of an optimum current value flows to the LED 111 and the LED 111 is turned on. When the LED 111 enters a lighting state in the way, as shown in step S51, the switch control section 163 enters a standby state until a third switch OFF instruction is outputted from the switch instructing section 162.

When the OFF instruction is not outputted from the switch instructing section 162, as shown in step S52, the optical-adapter-attachment-and-detachment determining section 124 continues an operation for determining whether the optical adapter 104 is not removed from the distal end portion 103. When the optical-adapter-attachment-and-detachment determining section 124 determines that the optical adapter 104 is not removed, processing in step S51 is started.

Conversely, when the optical adapter 104 is removed from the distal end portion 103, as shown in step S53, the LED 111 is turned off. As shown in the next step S54, the system control section 129 stops the supply of the optimum LED turn-on signal Si and turns off the LED driving section 123. As shown in step S55, the switch control section 163 switches the third switch 161 to the open state. The optical-adapter-attachment-and-detachment determining section 124 switches the first switch 118*a* of the switching circuit 118 to the attachment-and-detachment determining power supply 121 side and switches the second switch 118*b* thereof to the open state. Then processing in step S52 is started.

On the other hand, when the OFF instruction is outputted from the switch instructing section 162 in step S51, as shown in step S56, the system control section 129 stops the output of the optimum LED turn-on signal Si to the LED driving section 123, the LED driving section 123 is turned off, and the LED 111 is turned off as shown in step S57.

In the next step S58, processing same as that in step S55 is performed. Then, the processing in step S42 is started.

According to the present embodiment in which the operations are performed as described above, the effects same as those in the seventh embodiment are realized. Moreover, supply of an electric current to the optical adapter 104 side and stop of the supply can be controlled according to an instruction of the user. Therefore, workability is high.

<Eleventh Embodiment>

Figure 23:
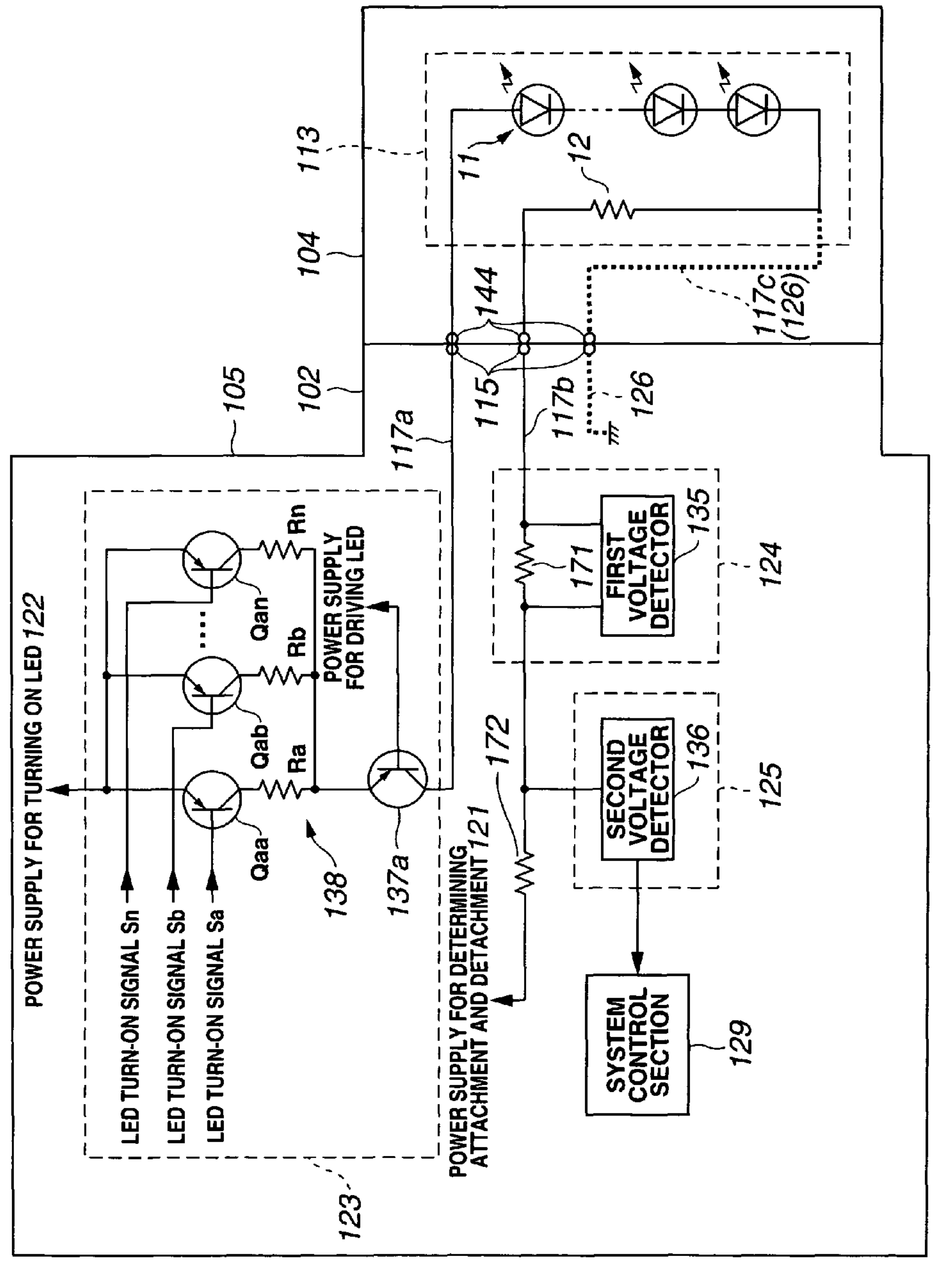
FIG. 23 is a circuit diagram showing a circuit configuration of a main part in an endoscope apparatus according to an eleventh embodiment of the present invention.

Next, an eleventh embodiment of the present invention is explained with reference to FIG. 23. FIG. 23 shows a circuit configuration of a main part in an endoscope apparatus according to the eleventh embodiment. The endoscope apparatus according to the present embodiment has a configuration in which the number of electric contacts 114 on the adapter side of the optical adapter 104 is increased to three in appearance and the number of electric contacts 115 on the insertion section side of the endoscope apparatus main body 105 is also increased to three in appearance in association with the number of electric contacts 114.

The cathode terminal of the LED 111 in the optical adapter 104 of the endoscope according to the present embodiment and one terminal of the resistor 112 are connected to a common electric contact 114 and the anode terminal of the LED 111 and the other terminal of the resistor 112 are connected to different electric contacts 114, respectively. On the endoscope apparatus main body 105 side, the electric contact 114 connected to the anode terminal of the LED 111 is connected to the electric contact 115, the electric contact 115 is connected to the signal line 117*a*, and the signal line 117*a* is connected to the LED driving section 123.

The LED driving section 123 configures a constant current circuit of a discharge type different from an intake type according to the seventh to tenth embodiments. In other words, the signal line 117*a* is connected to a collector terminal of a transistor 137*a* of a PNP type included in the LED driving section 123. The resistors Ra, Rb, . . . , and Rn included in the LED-driving-current setting section 138 are connected to an emitter terminal of the transistor 137*a*. Collector terminals of transistors Qaa, Qba, . . . , and Qna of a PNP type are connected to these resistors Ra, Rb, . . . , and Rn, respectively. Respective emitters are connected to the LED turn-on power supply 122. A base terminal of the transistor 137*a* is connected to the LED driving power supply.

As in the case of the seventh embodiment and the like, the LED turn-on signals Sa, Sb, . . . , and Sn can be applied to base terminals of the transistors Qaa, Qba, . . . , and Qna.

A resistor 171 is connected in series to the signal line 117*b* connected to the resistor 112. The optical-adapter-attachment-and-detachment determining section 124 which performs attachment and detachment determination for the optical adapter 104 by detecting, using the first voltage detection circuit 135, voltages at both ends of the resistor 171 is formed.

The resistor 171 is connected to the attachment-and-detachment determining power supply 121 through another resistor 172 further connected in series. The optical-adapter-type determining section 125 which determines a type of the optical adapter 104 by detecting, using the second voltage detection circuit 136, a voltage between the resistor 171 and the resistor 172 is formed.

The optical-adapter-type determining section 125 determines a type of the optical adapter 104 according to a ratio of resistances of the resistor 172 and the resistor 112 and outputs a result of the determination to the system control section 129. The influence of the resistor 171 can be neglected because a resistor having an extremely low resistance compared with those of the resistor 172 and the resistor 112 is used as the resistor 171.

The system control section 129 controls, on the basis of the determination result of the optical-adapter-type determining section 125, the LED driving section 123 to apply one signal out of the LED turn-on signals Sa to Sn according to a type of the optical adapter 104. Other components of the endoscope apparatus according to the present embodiment are the same as those in the seventh embodiment.

Operations in the present embodiment with such a configuration are explained.

When the optical adapter 104 is connected to the distal end portion 103, the optical-adapter-attachment-and-detachment determining section 124 detects generation of voltages at both the ends of the resistor 171 to thereby determine that the optical adapter 104 is connected to the distal end portion 103. The optical-adapter-attachment-and-detachment determining section 124 outputs an indication that the optical adapter 104 is connected to the distal end portion 103 to the system control section 129. Moreover, the second voltage detection circuit 136 of the optical-adapter-type determining section 125 measures a voltage value at a connection point of the resistor 172 and the resistor 171, thereby determining a type of the connected optical adapter 104 and outputs a determination signal to the system control section 129.

The system control section 129 having received the determination signal from the optical-adapter-type determining section 125 applies the LED turn-on signal Si corresponding to the type of the optical adapter to a base terminal of a transistor Qia of the LED driving section 123. The system control section 129 brings the transistor Qia into a conduction state and feeds an optimum electric current to the LED 111 through a resistor Ri connected to a collector terminal thereof. Therefore, the LED 111 is turned on.

In the state, the optical-adapter-attachment-and-detachment determining section 124 stays on standby until the optical adapter 104 enters a state in which the optical adapter 104 is removed from the distal end portion 103. When the optical adapter 104 is removed from the distal end portion 103, the optical-adapter-attachment-and-detachment determining section 124 outputs an indication that the optical adapter 104 is removed from the distal end portion 103 to the system control section 129. The system control section 129 receives a signal from the optical-adapter-attachment-and-detachment determining section 124, stops the output of the LED turn-on signal Si, and turns off the transistor 137*a*.

The system control section 129 and the like return to the initial state and the optical-adapter-attachment-and-detachment determining section 124 enters a waiting state for the optical adapter 104 to be connected to the distal end portion 103.

According to the present embodiment, the endoscope apparatus has a switching circuit in terms of a function. Therefore, the endoscope apparatus performs the attachment and detachment determination and type determination for the optical adapter 104 using the attachment-and-detachment determining power supply 121 and, when the optical adapter 104 is connected to the distal end portion 103, supplies an electric current for turning on the LED 111 from the LED turn-on power supply 122 and turns on the LED 111 with an appropriate electric current.

In the present embodiment, the optical-adapter-attachment-and-detachment determining section 124 and the optical-adapter-type determining section 125 are clearly shown separately. However, both the optical-adapter-attachment-and-detachment determining section 124 and the optical-adapter-type determining section 125 have a function of detecting a voltage, both the determining sections may be used as a determining section to collectively perform the functions of the two determining sections. For example, both attachment and detachment determination and type determination for an optical adapter may be performed by the optical-adapter-type determining section 125. In other words, the optical-adapter-type determining section 125 may be used as an optical-adapter attachment-and-detachment and type determining section. As described above, both the optical-adapter-attachment-and-detachment determining section 124 and the optical-adapter-type determining section 125 are configured by the system control section 129. Therefore, both the determining sections may be physically integral.

In the explanation of the present embodiment, for ease of explanation, the number of the electric contacts 114 on the adapter side and the electric contacts 115 on the insertion section side is three in appearance. However, a signal line connected to the GND of the signal line 126 connected to the CCD 116 can be used as the signal line 117*c* used as a signal line connected to the GND, i.e., an earth potential line. Therefore, the number of signal lines used for attachment and detachment determination and type determination is two and the number of electric contacts 114 of the optical adapter 104, and the number of electric contacts 115 on the endoscope apparatus main body 105 side are practically two. Therefore, the endoscope apparatus according to the present embodiment realizes actions and effects same as those of the endoscope apparatus according to the seventh embodiment.

In the endoscope apparatus according to the present embodiment, as in the endoscope according to the tenth embodiment, it is also possible that the switch instructing section 162 and the switch control section 163 are provided, the third switch 161 is inserted between the attachment-and-detachment determining power supply 121 and the resistor 172, and the switch control section 163 is controlled according to a determination result of the optical-adapter-attachment-and-detachment determining section 124. The voltage detection circuit of the optical-adapter-attachment-and-detachment determining section 124 can also be configured by a comparator, an A-D converter, or the like. The transistors Qaa to Qna can also be configured by an FET, a relay, a photo-coupler, a photo-MOS relay, or the like.

<Twelfth Embodiment>

Figure 24:
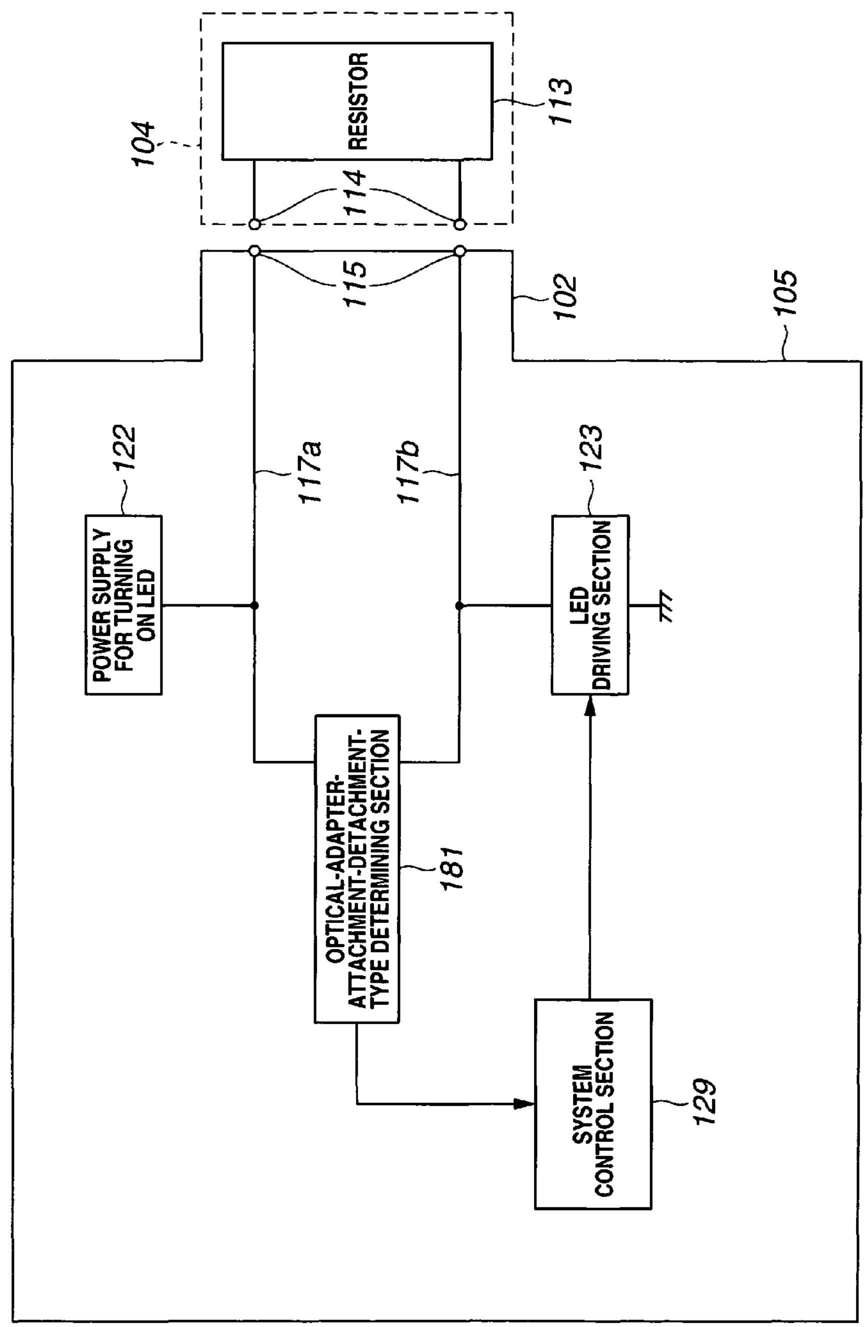
FIG. 24 is a block diagram showing a configuration of a main part in an endoscope apparatus according to a twelfth embodiment of the present invention.

Next, a twelfth embodiment of the present invention is explained with reference to FIGS. 24 to 26. FIG. 24 shows a configuration of a main part in the twelfth embodiment as a block diagram. In the seventh to tenth embodiments, the switching circuit 118 is provided to use the two signal lines 117*a* and 117*b*. However, in the present embodiment, it is possible to determine attachment and detachment and a type of the optical adapter 104 using the two signal lines 117*a* and 117*b* without using the switching circuit 118.

Therefore, the endoscope apparatus main body 105 according to the present embodiment configured by providing, without providing the switching circuit 118, an optical-adapter attachment-and-detachment and type determining section 181 which performs attachment and detachment determination and type determination for the optical adapter 104 between the signal lines 117*a* and 117*b* and removing the optical-adapter-attachment-and-detachment determining section 124 and the optical-adapter-type determining section 125 in the endoscope apparatus main body 105 shown in FIG. 16.

In the endoscope apparatus according to the present embodiment, the attachment-and-detachment determining power supply 121 shown in FIG. 16 is not provided. In the endoscope apparatus according to the present embodiment, the LED turn-on power supply 122 is connected to the signal line 117*a*, the LED driving section 123 is connected to the other signal line 117*b*, and the LED driving section 123 is controlled to be driven by the system control section 129. A more detailed configuration of the respective sections shown in FIG. 24 is shown in FIG. 25.

Figure 25:
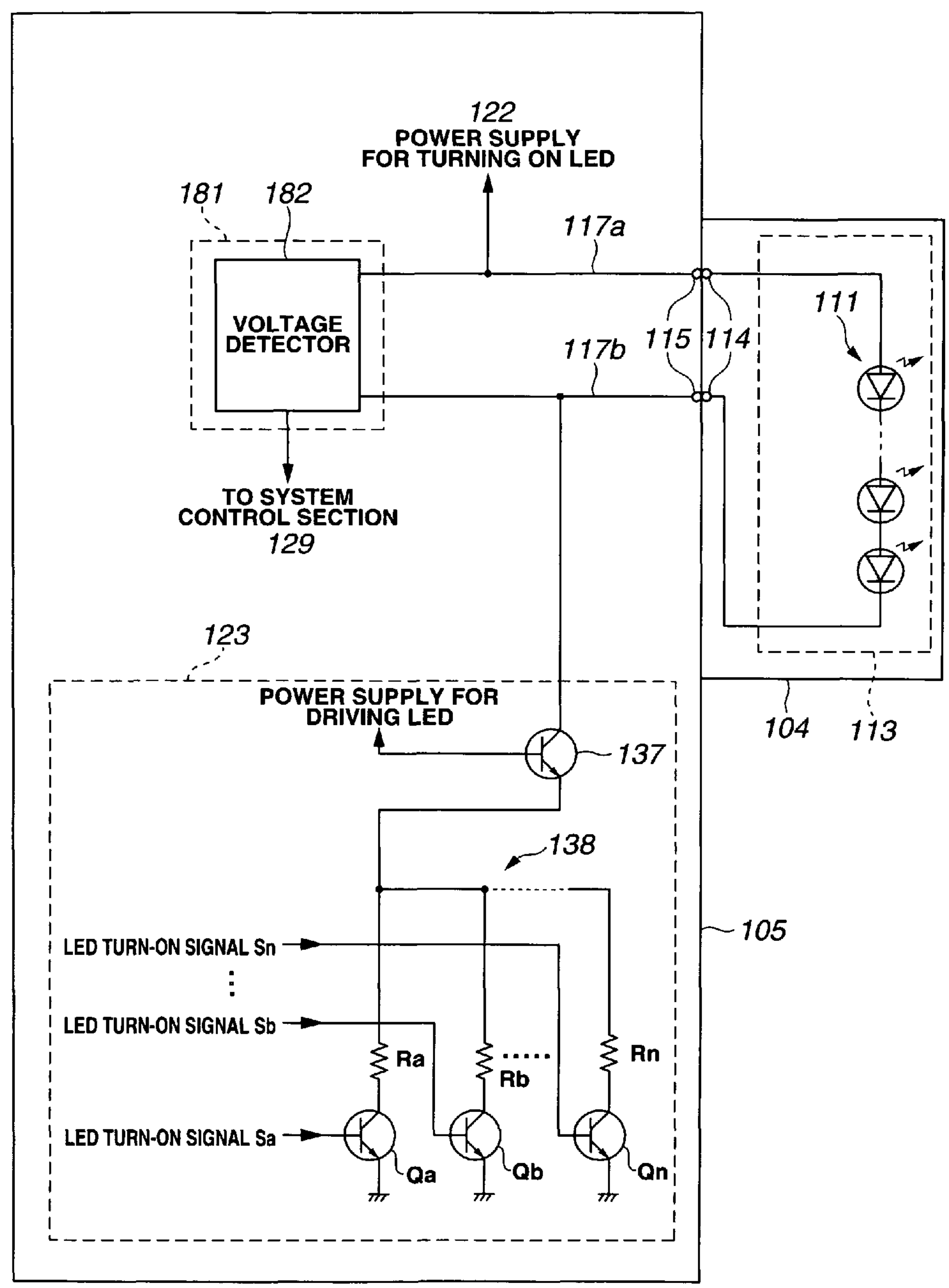
FIG. 25 is a circuit diagram showing a more specific circuit configuration of FIG. 24.
Figure 26:
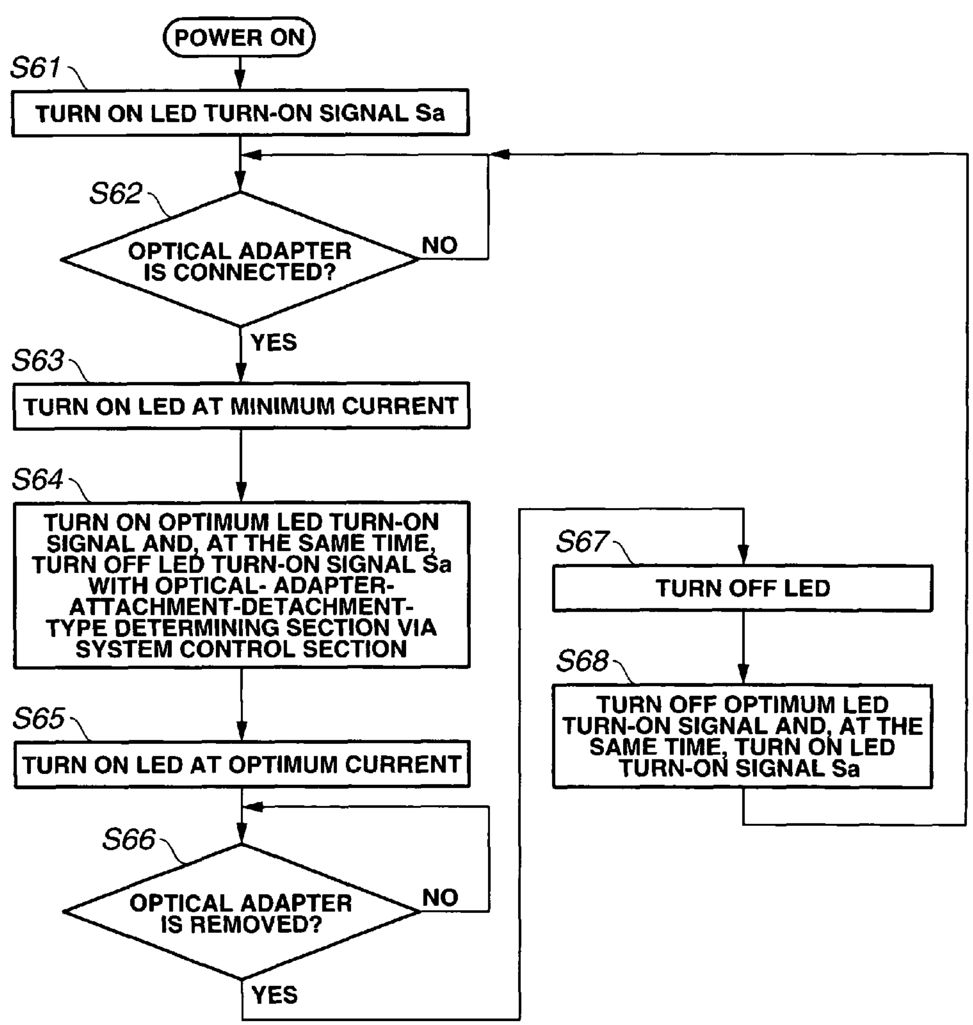
FIG. 26 is a flowchart showing operation contents according to the twelfth embodiment of the present invention.

As shown in FIG. 25, in the optical adapter 104 in the endoscope apparatus according to the present embodiment, the resistor 112 is not provided in the resistor element 113 shown in FIG. 17. In the optical adapter 104 in the present embodiment, when the number of LEDs 111 is different, a type of the optical adapter 104 is also different. In the endoscope apparatus according to the present embodiment, a type of the optical adapter 104 can be determined according to the number of LEDs 111.

In the endoscope apparatus main body 105 according to the present embodiment, a voltage detection circuit 182 is connected between the signal line 117*a* and the signal line 117*b* and the optical-adapter attachment-and-detachment and type determining section 181 which determines attachment and detachment and a type of the optical adapter 104 is formed in the endoscope apparatus main body 105 shown in FIG. 17. A configuration of the LED driving section 123 is a configuration same as that of the LED driving section 123 shown in FIG. 17. The base terminal of the transistor 137 included in the LED driving section 123 is always in a state in which the base terminal is connected to the LED driving power supply.

Operations in the present embodiment with such a configuration are explained.

When electric power is supplied to the endoscope apparatus main body 105, the system control section 129 turns on, for example, only the LED turn-on signal Sa with a smallest current amount, i.e., a largest resistance Ra.

When the optical adapter 104 is not connected to the distal end portion 103 in the state, the voltage detection circuit 182 of the optical-adapter attachment-and-detachment and type determining section 181 determines that the optical adapter 104 is not connected to the distal end portion 103 and sends a control signal of the determination to the system control section 129.

The system control section 129 receives the control signal, outputs only the LED turn-on signal Sa to the LED driving section 123, and instructs the transistor Qa, to a base terminal of which the LED turn-on signal Sa is applied, to stay on standby in a turn-on state.

The voltage detection circuit 182 is configured by an AD converter or the like.

The system control section 129 can be configured by a comparator, a CPU, or the like.

When the optical adapter 104 is connected to the distal end portion 103, the voltage detection circuit 182 of the optical-adapter attachment-and-detachment and type determining section 181 determines that the optical adapter 104 is connected to the distal end portion 103, determines the number of LED elements of the LED 111 of the optical adapter 4, i.e., a type of the optical adapter 104, and transfers the control signal to the system control section 129.

The system control section 129 receives the control signal and controls to turn on any one of the LED turn-on signals Sa to Sn in order to send the signal with a current value optimum for the LED 111 of the optical adapter 104 to the LED driving section 123.

As a reference, an example of detected voltages with respect to an optical adapter having LEDS 111 with different number of LED elements connected in series is shown below.

| Number of LED elements | Detected voltage (V) |
|---|---|
| 1 | 3.5 |
| 2 | 7.0 |
| 3 | 10.5 |
| 4 | 14.0 |
| 5 | 17.5 |
| 6 | 21.0 |

In this way, the optical-adapter-type determining section 125 can determine not only attachment and detachment of the optical adapter 104 but also a type of the optical adapter 104 by using the optical adapter 104 having a different detected voltage value corresponding to the number of mounted LED elements.

Next, a flow of processing according to the present embodiment is explained with reference to a flowchart of FIG. 26.

When electric power is supplied to the endoscope apparatus, in the first step S61, the system control section 129 turns on only the LED turn-on signal Sa with a smallest current amount.

In the state, as shown in step S62, the optical-adapter attachment-and-detachment and type determining section 181 determines whether the optical adapter 104 is connected to the distal end portion 103 and waits for the optical adapter 104 to be connected to the distal end portion 103.

When the optical adapter 104 is connected to the distal end portion 103, as shown in step S63, the LED 111 is turned on with a minimum electric current. The system control section 129 to which a control signal having information indicating that the optical adapter 104 is connected to the distal end portion 103 and information on the number of elements of the LED 111 is sent by the optical-adapter attachment-and-detachment and type determining section 181 turns on the optimum LED turn-on signal Si and, at the same time, turns off the LED turn-on signal Sa with the smallest current amount.

The LED 111 is turned on with an optimum electric current according to such a control by the system control section 129. When the LED 111 enters a state in which the LED 111 is turned on with the optimum electric current, as shown in step S66, the voltage detection circuit 182 of the optical-adapter attachment-and-detachment and type determining section 181 monitors whether or not the optical adapter 104 is removed from the distal end portion 103 according to voltage detection.

When the voltage detection circuit 182 detects that the optical adapter 104 is removed from the distal end portion 103, as shown in step S67, the LED 111 is turned off.

The system control section 129 to which a signal having information indicating that the optical adapter 104 is removed from the distal end portion 103 is sent from the voltage detection circuit 182 of the optical-adapter attachment-and-detachment and type determining section 181 turns off, as shown in step 568, the optimum LED turn-on signal Si and, at the same time, turns on only the LED turn-on signal Sa with the smallest current amount. The processing of the system control section 129 returns to the processing starting from the step S62.

With the endoscope apparatus according to the present embodiment, it is possible to perform, with the simple configuration not requiring the attachment-and-detachment determining power supply, attachment and detachment determination and type determination for the optical adapter 104 and turn on the LED 11 with an appropriate electric current corresponding to the number of LED elements mounted in the connected optical adapter 104.

Figure 27:
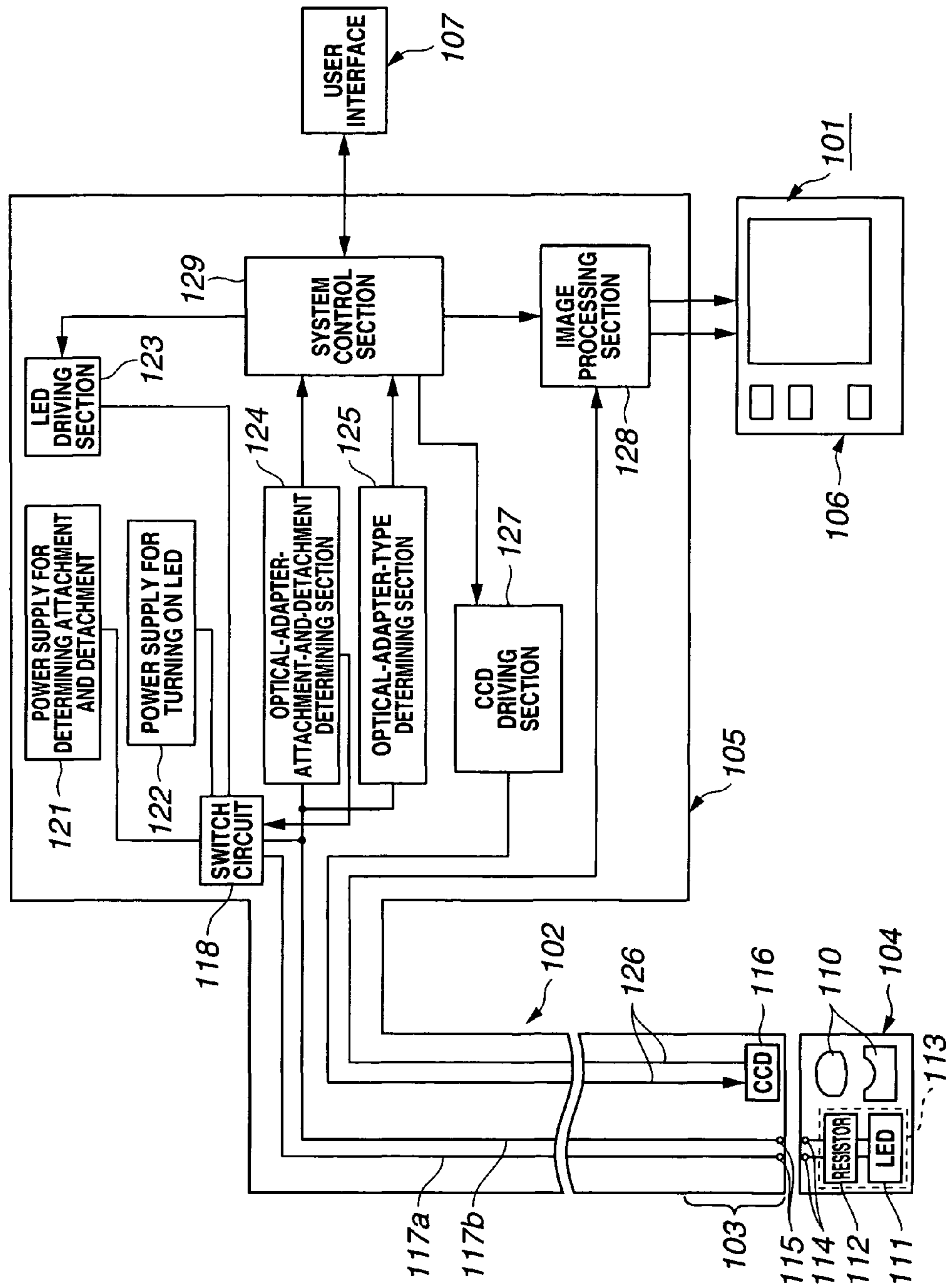
FIG. 27 is a block diagram showing an overall configuration of an endoscope apparatus according to a thirteenth embodiment of the present invention.

FIG. 27 is a block diagram showing an overall configuration of the endoscope apparatus 101 according to the seventh embodiment. However, unlike FIG. 15, the optical-adapter-attachment-and-detachment determining section 124 and the optical-adapter-type determining section 125 are shown as components different from the system control section 129. In the present invention, the optical-adapter-attachment-and-detachment determining section 124 and the optical-adapter-type determining section 125 are configured by the system control section 129. However, for ease of explanation of operations, the above explanation is also based on the configuration shown in FIG. 27. It goes without saying that, as shown in FIG. 27, the effects of the present invention can be realized even if the optical-adapter-attachment-and-detachment determining section 124 and the optical-adapter-type determining section 125 are components different from the system control section 129.

In the respective embodiments described above, it is preferable that the system control section 29 displays a determination result of at least any one of the optical-adapter-attachment-and-detachment determining section 124 and the optical-adapter-type determining section 125 on a display section such as the display device 6. Since the user can confirm that the optical adapter 4 is connected to the endoscope or confirm a type of the optical adapter 4, workability is improved.

What is displayed on the display section is, as a determination result of the optical-adapter-attachment-and-detachment determining section 124, a warning indication in cases (a) to (d) described below. In other words, (a) when a power supply is turned on in a state in which the optical adapter 104 is not connected, (b) when the power supply is turned on in a state in which the optical adapter 104 is connected or, even if the optical adapter 104 is connected after the power supply is turned on, it is recognized by the optical-adapter-attachment-and-detachment determining section 124 that the optical adapter 104 is not connected, (c) when the power supply is turned on in a state in which the optical adapter 104 is connected or, even if the optical adapter 104 is connected after the power is turned on, type determination cannot be performed in the optical-adapter-type determining section 125, (d) when the optical adapter 104 is removed in a state of power on, any one of the following warning indications may be displayed.

"It is likely that the optical adapter has a trouble"

"It is likely that an attachment of the optical adapter is loosened"

"The optical adapter is not normally attached"

Instead of displaying the indication on the display section, a notification or the like by sound with a display may be performed.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:

an optical adapter including: (i) at least one light emitting diode, and (ii) a resistor having a resistance set in accordance with a type of the optical adapter, the at least one light emitting diode and the resistor being connected in parallel between a first adapter side electric contact and a second adapter side electric contact;

an insertion section including: (i) a distal end portion to which the optical adapter is detachably attachable, (ii) first and second insertion section side electric contacts connectable to the adapter side electric contacts of the optical adapter, and (iii) first and second signal lines connected to the first and second insertion section electric contacts, respectively;

a luminous body turn-on power supply for turning on the at least one light emitting diode;

an attachment-and-detachment determining power supply which determines attachment and detachment of the optical adapter to and from the insertion section, the attachment-and-detachment determining power supply being a lower-voltage power supply than the luminous body turn-on power supply, and having a voltage set to be lower than a value of a forward drop voltage of the at least one light emitting diode;

a first switch for switching between a connection of the first signal line to one of (i) the attachment-and-detachment determining power supply and (ii) the luminous body turn-on power supply;

a driving section which sets a driving current to be supplied to the at least one light emitting diode from the luminous body turn-on power supply; and a system control section which controls the first switch to switch the connection of the first signal line to the luminous body turn-on power supply when the optical adapter is attached to the insertion section, and controls the first switch to switch the connection of the first signal line to the attachment-and-detachment determining power supply when the optical adapter is detached from the insertion section.

2. The endoscope apparatus according to claim 1, wherein the resistance of the resistor is larger than a resistance of the at least one light emitting diode.

3. The endoscope apparatus according to claim 1, wherein the attachment-and-detachment determining power supply is a constant-voltage power supply and the luminous body turn-on power supply is a constant-current power supply.

4. The endoscope apparatus according to claim 1, wherein the resistor included in the optical adapter is set to have a different resistance in accordance with at least one of a number of the light emitting diodes and light emission characteristics of the light emitting diodes.

5. The endoscope apparatus according to claim 1, wherein the endoscope apparatus is operable with a plurality of optical adapters, each comprising a resistor with a different resistance that is set in accordance with at least one of a number of the light emitting diodes and light emission characteristics of the light emitting diodes of the optical adapter.

6. The endoscope apparatus according to claim 1, further comprising:

an optical-adapter-attachment-and-detachment determining section which: (i) when the attachment-and-detachment determining power supply is connected to the first signal line and the second signal line by the first switch, determines attachment and detachment of the optical adapter to and from the insertion section, and (ii) when the luminous body turn-on power supply is connected to the first signal line and the second signal line by the first switch, continues to determine the attachment and detachment of the optical adapter to and from the insertion section to determine whether or not the optical adapter is detached from the insertion section; and an optical-adapter-type determining section which, when the attachment-and-detachment determining power supply is connected to the first signal line and the second signal line by the first switch, determines a type of the optical adapter based on the resistance of the resistor of the optical adapter;

wherein the driving section sets the driving current to be supplied to the at least one light emitting diode from the luminous body turn-on power supply to a value according to the type of the optical adapter determined by the optical-adapter-type determining section; and wherein the system control section: (i) when the optical-adapter-attachment-and-detachment determining section determines that the optical adapter is attached and the optical-adapter-type determining section determines the type of the optical adapter, controls the first switch to switch the connection of the first signal line to the luminous body turn-on power supply, controls the driving section to set the driving current to be supplied to the at least one light emitting diode from the luminous body turn-on power supply to the value according to the type of the optical adapter determined by the optical-adapter-type determining section, and performs control not to read a control signal from the optical-adapter-type determining section, and (ii) when the optical-adapter-attachment-and-detachment determining section determines that the optical adapter is detached from the insertion section, performs control to stop the driving of the driving section, and then controls the first switch to switch the connection of the first signal line to the attachment-and-detachment determining power supply.

7. The endoscope apparatus according to claim 1, further comprising:

a second switch which performs connection by switching between a state in which a current flows in the driving section and a state in which a current does not flow in the driving section;

wherein the system control section controls the second switch to (i) perform connection by switching to the state in which the current flows in the driving section when the optical adapter is attached to the insertion section, and (ii) perform connection by switching to the state in which the current does not flow in the driving section when the optical adapter is detached from the insertion section.

8. The endoscope apparatus according to claim 6, further comprising a display section which displays a result of the determination of at least one of the optical-adapter-attachment-and-detachment determining section and the optical-adapter-type determining section, wherein the system control section performs control to display the result of the determination on the display section.

9. The endoscope apparatus according to claim 6, wherein the system control section performs control of an image pickup device driving section for driving an image pickup device provided at the distal end portion of the insertion section, in accordance with a result of a determination by the optical-adapter-attachment-and-detachment determining section that the optical adapter is connected to the distal end portion of the insertion section.

10. The endoscope apparatus according to claim 9, wherein the system control section performs control to operate the image pickup device driving section when the optical-adapter-attachment-and-detachment determining section determines that the optical adapter is attached to the insertion section, and sets the image pickup device driving section to a non-operation state when the optical-adapter-attachment-and-detachment determining section determines that the optical adapter not attached to the insertion section.

11. The endoscope apparatus according to claim 1, wherein:

the first switch is configured to switch between a connection of both of the first signal line and the second signal line to one of (i) the attachment-and-detachment determining power supply and (ii) the luminous body turn-on power supply; and the system control section controls the first switch to switch the connection of both of the first signal line and the second signal line to the luminous body turn-on power supply when the optical adapter is attached to the insertion section, and controls the first switch to switch the connection of both of the first signal line and the second signal line to the attachment-and-detachment determining power supply when the optical adapter is detached from the insertion section.

* * * * *